United States Patent
Liang et al.

(10) Patent No.: US 10,625,244 B2
(45) Date of Patent: Apr. 21, 2020

(54) SILVER PROMOTED CATALYSTS FOR OXIDATIVE COUPLING OF METHANE

(71) Applicant: Sabic Global Technologies, B.V., Bergen Op Zoom (NL)

(72) Inventors: Wugeng Liang, Richmond, TX (US); Vidya Sagar Reddy Sarsani, Pearland, TX (US); David West, Bellaire, TX (US); Hector Perez, Angleton, TX (US); Aghaddin Mamedov, Sugar Land, TX (US); Istvan Lengyel, Lake Jackson, TX (US); James Lowrey, Pearland, TX (US)

(73) Assignee: Sabic Global Technologies, B.V., Bergen Op Zoom (NL)

( * ) Notice: Subject to any disclaimer, the term of this patent is extended or adjusted under 35 U.S.C. 154(b) by 0 days.

(21) Appl. No.: 15/208,862

(22) Filed: Jul. 13, 2016

(65) Prior Publication Data

US 2017/0014807 A1     Jan. 19, 2017

Related U.S. Application Data

(60) Provisional application No. 62/192,761, filed on Jul. 15, 2015, provisional application No. 62/246,711, (Continued)

(51) Int. Cl.
    *B01J 23/63*        (2006.01)
    *B01J 23/68*        (2006.01)
    (Continued)

(52) U.S. Cl.
    CPC .......... *B01J 23/688* (2013.01); *B01J 23/002* (2013.01); *B01J 23/66* (2013.01); *B01J 35/006* (2013.01);
    (Continued)

(58) Field of Classification Search
    CPC ........ B01J 23/688; B01J 23/66; B01J 35/023; B01J 35/0013; B01J 35/006; B01J 23/002;
    (Continued)

(56) References Cited

U.S. PATENT DOCUMENTS 4,876,409 A    10/1989   Leyshon et al.
6,087,545 A    7/2000   Choudhary et al.
(Continued)

FOREIGN PATENT DOCUMENTS

CA          1276946       11/1990
CA          2856310 A1    6/2013
(Continued)

OTHER PUBLICATIONS

Foreign Communication from a related counterpart application— Invitation to Pay Additional Fees of International Application No. PCT/US2016/041990 dated Nov. 2, 2016, 10 pages.
(Continued)

*Primary Examiner* — James A Fiorito
(74) *Attorney, Agent, or Firm* — Conley Rose, P.C.; Rodney B. Carroll

(57) ABSTRACT

An oxidative coupling of methane (OCM) catalyst composition comprising one or more oxides doped with Ag; wherein one or more oxides comprises a single metal oxide, mixtures of single metal oxides, a mixed metal oxide, mixtures of mixed metal oxides, or combinations thereof; and wherein one or more oxides is not $La_2O_3$ alone. A method of making an OCM catalyst composition comprising calcining one or more oxides and/or oxide precursors to form one or more calcined oxides, wherein the one or more oxides comprises a single metal oxide, mixtures of single metal oxides, a mixed metal oxide, mixtures of mixed metal oxides, or combinations thereof, wherein the one or more
(Continued)

oxides is not $La_2O_3$ alone, and wherein the oxide precursors comprise oxides, nitrates, carbonates, hydroxides, or combinations thereof; doping the one or more calcined oxides with Ag to form the OCM catalyst composition; and thermally treating the OCM catalyst composition.

21 Claims, 6 Drawing Sheets

Related U.S. Application Data filed on Oct. 27, 2015, provisional application No. 62/247,021, filed on Oct. 27, 2015, provisional application No. 62/317,760, filed on Apr. 4, 2016.

(51) Int. Cl.

| | |
|---|---|
| *B01J 23/66* | (2006.01) |
| *C07C 2/84* | (2006.01) |
| *B01J 35/00* | (2006.01) |
| *B01J 37/02* | (2006.01) |
| *B01J 23/00* | (2006.01) |
| *B01J 37/08* | (2006.01) |
| *B01J 35/02* | (2006.01) |

(52) U.S. Cl.
CPC ......... *B01J 35/0013* (2013.01); *B01J 35/023* (2013.01); *B01J 37/0205* (2013.01); *B01J 37/0211* (2013.01); *B01J 37/0236* (2013.01); *B01J 37/088* (2013.01); *C07C 2/84* (2013.01); *B01J 2523/00* (2013.01); *C07C 2521/08* (2013.01); *C07C 2523/04* (2013.01); *C07C 2523/10* (2013.01); *C07C 2523/30* (2013.01); *C07C 2523/34* (2013.01); *C07C 2523/66* (2013.01); *C07C 2523/68* (2013.01); *Y02P 20/582* (2015.11)

(58) Field of Classification Search
CPC ................ B01J 37/0205; B01J 37/0211; B01J 37/0236; B01J 37/088; C07C 2/84; C07C 2523/20; C07C 2521/08; C07C 2523/66; C07C 2523/68; C07C 2523/34; C07C 2523/30; C07C 2523/04

See application file for complete search history.

(56) References Cited

U.S. PATENT DOCUMENTS

| | | | |
|---|---|---|---|
| 8,815,080 B2 | 8/2014 | Sundaram | |
| 8,912,381 B2 | 12/2014 | Chinta et al. | |
| 8,921,256 B2 | 12/2014 | Cizeron et al. | |
| 8,962,517 B2 | 2/2015 | Zurcher et al. | |
| 2007/0093559 A1 | 4/2007 | Norskov et al. | |
| 2007/0249879 A1 | 10/2007 | Iaccino et al. | |
| 2012/0041246 A1 | 2/2012 | Scher et al. | |
| 2012/0065412 A1* | 3/2012 | Abdallah | C07C 2/64 549/518 |
| 2013/0165728 A1 | 6/2013 | Zurcher et al. | |
| 2014/0080699 A1 | 3/2014 | Ghose et al. | |
| 2014/0107385 A1 | 4/2014 | Schammel et al. | |
| 2014/0121433 A1 | 5/2014 | Cizeron et al. | |
| 2014/0128484 A1 | 5/2014 | Hassan et al. | |
| 2014/0171707 A1 | 6/2014 | Nyce et al. | |
| 2015/0152025 A1 | 6/2015 | Cizeron et al. | |
| 2015/0307415 A1 | 10/2015 | Rafique et al. | |
| 2015/0321974 A1 | 11/2015 | Schammel et al. | |

FOREIGN PATENT DOCUMENTS

| | | |
|---|---|---|
| CN | 103350002 A | 10/2013 |
| EP | 0256857 A1 | 2/1988 |
| EP | 0418974 A1 | 3/1991 |
| EP | 2119491 A1 | 11/2009 |
| EP | 2576046 B1 | 11/2014 |
| WO | 2007126811 A2 | 11/2007 |
| WO | 2008138785 A1 | 11/2008 |
| WO | 2010117696 A1 | 10/2010 |
| WO | 2014089479 A1 | 6/2014 |
| WO | 2014181241 A1 | 11/2014 |
| WO | 2014191874 A1 | 12/2014 |
| WO | 2016200504 A1 | 12/2016 |

OTHER PUBLICATIONS

Noon, Daniel, et al., "Oxidative coupling of methane with La2O3—CeO2 nanofiber fabrics: A reaction engineering study," Journal of Natural Gas Science and Engineering, 2014, pp. 406-411, vol. 18, Elsevier B.V.

Foreign Communication from a related counterpart application—International Search Report and Written Opinion of International Application No. PCT/US2016/041990 dated Feb. 20, 2017, 24 pages.

Chou, Lingjun, et al., "Influence of SNO2-doped W—Mn/SiO2 for oxidative conversion of methane to high hydrocarbons at elevated pressure," Applied Catalysis A: General, 2003, pp. 185-191, vol. 238, Elsevier Science, B.V.

Gaffney, Anne M., "Oxidative Coupling of Methane over Sodium Promoted Praseodymium Oxide," Journal of Catalysis, 1988, pp. 422-432, vol. 114, Academic Press, Inc.

Kundakovic, L.J., et al., "Cu- and Ag-Modified Cerium Oxide Catalysts for Methane Oxidation," Journal of Catalysis, 1998, pp. 203-221, vol. 179, No. CA 982213, Academic Press.

Nagy, Anton J., et al., "The Role of Subsurface Oxygen in the Silver-Catalyzed, Oxidative Coupling of Methane," Journal of Catalysis, 1999, pp. 58-68, vol. 188, Academic Press.

Salehoun, V., et al., "Dynamics of Mn/Na2WO4/SiO2 catalyst in oxidative coupling of methane," Chemical Engineering Science, 2008, pp. 4910-4916, vol. 63, Elsevier Ltd.

Shahri, Seyed Menu Kamali, et al., "Ce-promoted Mn/Na2WO4/SiO2 catalyst for oxidative coupling of methane at atmospheric pressure," Journal of Natural Gas Chemistry, 2010, pp. 47-53, vol. 19, No. 1, Dalian Institute of Chemical Physics, Chinese Academy of Sciences.

Arndt, S., et al., "Mn—Na2WO4/SiO2 as catalyst for the oxidative coupling of methane. What is really known?," Applied Catalysis A: General, 2012, pp. 53-61, vol. 425-426, Elsevier B.V.

Choudhary, V.R., et al., "Beneficial Effect of Oxygen Distribution on Methane Conversion and C2-Selectivity in Oxidative Coupling of Methane to C2-Hydrocarbons over Lanthanum-promoted Magnesium Oxide," J. Chem. Soc., Chem. Commun., 1989, pp. 1526-1527.

Dedov, A.G., et al., "Oxidative coupling of methane catalyzed by rare earth oxides Unexpected synergistic effect of the oxide mixtures," Applied Catalysis A: General, 2003, pp. 209-220, vol. 245, Elsevier Science, B.V.

Farsi, Ali, et al., "A simple kinetic model for oxidative coupling of methane over La0.6Sr0.4Co0.8Fe0.2O3-δ nanocatalyst," Journal of Natural Gas Chemistry, 2011, pp. 325-333, vol. 20, Dalian Institute of Chemical Physics, Chinese Academy of Sciences.

Farsi, Ali, et al., "Influence of nanocatalyst on oxidative coupling, steam and dry reforming of methane: A short review," Arabian Journal of Chemistry, 2012, King Saud University, Elsevier B.V.

Farsi, Ali, et al., "Oxidative Coupling of Methane over Li/MgO: Catalyst and Nanocatalyst Performance," Chinese Journal of Chemical Physics, Feb. 27, 2011, pp. 70-76, vol. 24, No. 1, Chinese Physical Society.

Ferreira, Victor Jose Ferreira, "Development of nanostructured catalysts for the oxidative coupling of methane, Appendix A. Electro-catalytic experiments with natural gas over 5wt%Mn-5wt%Ce-5wt%Na2WO4/SiO2," Dissertation presented for the Ph.D. Degree in Chemical and Biological Engineering at the Faculty of Engineering, University of Porto, 2013, pp. 227-236, plus 1 page of publishing information, Portugal.

(56) References Cited

OTHER PUBLICATIONS

Filing Receipt and Specification of International Application No. PCT/US2016/041990 filed Aug. 25, 2016, entitled, "Silver Promoted Catalysts for Oxidative Coupling of Methane," 85 pages.
Filing Receipt and Specification of U.S. Appl. No. 62/192,761, filed Jul. 15, 2015, entitled, "Methane Oxidative Coupling with Silver Promoted Mn—Na2WO4/SiO2 Catalyst," 34 pages.
Filing Receipt and Specification of U.S. Appl. No. 62/246,711, filed Oct. 27, 2015, entitled, "Ag—La—Ce Catalyst for Oxidative Coupling of Methane," 49 pages.
Filing Receipt and Specification of U.S. Appl. No. 62/247,021, filed Oct. 27, 2015, entitled, "Ag—La—Ce Catalyst for Oxidative Coupling of Methane," 62 pages.
Filing Receipt and Specification of U.S. Appl. No. 62/317,760, filed Apr. 4, 2016, entitled, "Silver Promoted Catalysts for Oxidative Coupling of Methane," 40 pages.
Greish, Alexander A., et al., "Oxidative coupling of methane in the redox cyclic mode over the Ag—La2O3/SiO2 catalytic system," Mendeleev Communications, 2010, pp. 92-94, vol. 20, Elsevier.
Labinger, Jay A., "Oxidative Coupling of Methane: An Inherent Limit to Selectivity?," Catalysis Letters, 1988, pp. 371-376, vol. 1, J.C. Baltzer A.G. Scientific Publishing Company.
Lee, Mi Ran, et al., "A kinetic model for the oxidative coupling of methane over Na2WO4/Mn/SiO2," Fuel Processing Technology, 2012, pp. 175-182, vol. 96, Elsevier B.V.
Leyshon, D.W., "Thin Bed Reactor for Conversion of Methane to Higher Hydrocarbons," Natural Gas Conversion, 1991, p. 497-507, Elsevier Science Publishers B.V., Amsterdam.
Mahmoodi, S., et al., "Effect of promoter in the oxidative coupling of methane over synthesized Mn/SiO2 nanocatalysts via incipient wetness impregnation," Journal of Industrial and Engineering Chemistry, 2010, pp. 923-928 vol. 16, The Korean Society of Industrial and Engineering Chemistry, Elsevier B.V.
Mleczko, L., et al., "Catalytic oxidative coupling of methane-reaction engineering aspects and process schemes," Fuel Processing Technology, 1995, pp. 217-248, vol. 42, Elsevier Science, B.V.
Noon, Daniel, et al., "Oxidative Coupling of Methane by Nanofiber Catalysts," ChemCatChem Communications, 2013, pp. 146-149, vol. 5, Wiley-VCH Verlag GmbH & Co. KGaA, Weinheim.
Sinev, M. Yu., et al., "Kinetics of oxidative coupling of methane: Bridging the gap between comprehension and description," Journal of Natural Gas Chemistry, 2009, pp. 273-287, vol. 18, No. 3, Dalian Institute of Chemical Physics, Chinese Academy of Sciences.
Sung, Jae Suk, et al., "Peculiarities of oxidative coupling of methane in redox cyclic mode over Ag—La2O3/SiO2 catalysts," Applied Catalysis A: General, 2010, pp. 28-32, vol. 380, Elsevier B.V.
Yildiz, Mahmut, "Influences of Support Material Variation on Structure and Catalytic Performance of MnxOy—Na2WO4/SiO2 Catalyst for the Oxidative Coupling of Methane," Dissertation, Sep. 12, 2014, 250 pages, Berlin.
Zhang, Xin, et al., "Effect of Ag promoter on redox properties and catalytic performance of Ag—Mo—P—O catalysts for oxidative dehydrogenation of propane," Applied Surface Science, 2003, pp. 117-124, vol. 220, Elsevier, B.V.
Patent record of Singapore Patent No. SG146924B, published Apr. 29, 2011, including abstract and first claim, 3 pages, Thompson Innovation.
Fang, Xueping, et al., "Oxidative Coupling of Methane on W—Mn Catalysts," Journal of Molecular Catalysis (China), 1992, pp. 427-433, vol. 6, No. 6, including English abstract.
Fang, Xueping, et al., "Preparation and Characterization of W—Mn Catalyst for Oxidative Coupling of Methane," Journal of Molecular Catalysis (China), 1992, pp. 255-261, vol. 8, No. 4.
Foreign Communication from a related counterpart application—Written Opinion of the International Preliminary Examining Authority, Application No. PCT/US2016/041990 dated Jun. 26, 2017, 12 pages.
Filing Receipt and Specification of International Application No. PCT/US2017/048255 filed Aug. 25, 2016, entitled, "Multi-Stage Adiabatic Oxidative Coupling of Methane," 41 pages.
Foreign Communication from a related application—International Search Report and Written Opinion of the International Searching Authority of International Application No. PCT/US2017/048255 dated Nov. 23, 2017, 12 pages.
Foreign Communication from a related counterpart application—International Preliminary Report on Patentability, Application No. PCT/US2016/041990 dated Nov. 29, 2017, 29 pages.
Campbell, K.D., et al., "Methane Activation by Lanthanide Oxides," J. Phys. Chem., 1988, pp. 750-753, vol. 92, American Chemical Society.
Foreign communication from a related application—Examination Report of GCC Application No. GC 2016-31704, dated Sep. 17, 2018, 6 pages.
Foreign communication from a related application—Examination Report of GCC Application No. GC 2016-31704, dated Jan. 22, 2019, 4 pages.

\* cited by examiner

SILVER PROMOTED CATALYSTS FOR OXIDATIVE COUPLING OF METHANE

CROSS-REFERENCE TO RELATED APPLICATIONS

The present application is a non-provisional of and claims priority to U.S. Provisional Patent Application No. 62/192,761 filed Jul. 15, 2015 and entitled "Methane Oxidative Coupling with Silver Promoted MN-NA2WO4/SIO2," U.S. Provisional Patent Application Nos. 62/246,711 and 62/247,021, both filed Oct. 27, 2015 and entitled "Ag—La—Ce Catalyst for Oxidative Coupling of Methane," and U.S. Provisional Patent Application No. 62/317,760 filed Apr. 4, 2016 and entitled "Silver Promoted Catalysts for Oxidative Coupling of Methane," which applications are incorporated by reference herein in their entirety.

TECHNICAL FIELD

The present disclosure relates to catalyst compositions for oxidative coupling of methane (OCM), more specifically silver promoted catalyst compositions for OCM and methods of making and using same.

BACKGROUND

Hydrocarbons, and specifically olefins such as ethylene, are typically building blocks used to produce a wide range of products, for example, break-resistant containers and packaging materials. Currently, for industrial scale applications, ethylene is produced by heating natural gas condensates and petroleum distillates, which include ethane and higher hydrocarbons, and the produced ethylene is separated from a product mixture by using gas separation processes.

Oxidative coupling of the methane (OCM) has been the target of intense scientific and commercial interest for more than thirty years due to the tremendous potential of such technology to reduce costs, energy, and environmental emissions in the production of ethylene ($C_2H_4$). As an overall reaction, in the OCM, $CH_4$ and $O_2$ react exothermically over a catalyst to form $C_2H_4$, water ($H_2O$) and heat.

Ethylene can be produced by OCM as represented by Equations (I) and (II):

$$2CH_4 + O_2 \rightarrow C_2H_4 + 2H_2O \quad \Delta H = -67 \text{ kcal/mol} \quad \text{(I)}$$

$$2CH_4 + \tfrac{1}{2}O_2 \rightarrow C_2H_6 + H_2O \quad \Delta H = -42 \text{ kcal/mol} \quad \text{(II)}$$

Oxidative conversion of methane to ethylene is exothermic. Excess heat produced from these reactions (Equations (I) and (II)) can push conversion of methane to carbon monoxide and carbon dioxide rather than the desired $C_2$ hydrocarbon product (e.g., ethylene):

$$CH_4 + 1.5O_2 \rightarrow CO + 2H_2O \quad \Delta H = -124 \text{ kcal/mol} \quad \text{(III)}$$

$$CH_4 + 2O_2 \rightarrow CO_2 + 2H_2O \quad \Delta H = -192 \text{ kcal/mol} \quad \text{(IV)}$$

The excess heat from the reactions in Equations (III) and (IV) further exasperate this situation, thereby substantially reducing the selectivity of ethylene production when compared with carbon monoxide and carbon dioxide production.

Additionally, while the overall OCM is exothermic, catalysts are used to overcome the endothermic nature of the C—H bond breakage. The endothermic nature of the bond breakage is due to the chemical stability of methane, which is a chemically stable molecule due to the presence of its four strong tetrahedral C—H bonds (435 kJ/mol). When catalysts are used in the OCM, the exothermic reaction can lead to a large increase in catalyst bed temperature and uncontrolled heat excursions that can lead to catalyst deactivation and a further decrease in ethylene selectivity. Furthermore, the produced ethylene is highly reactive and can form unwanted and thermodynamically favored deep oxidation products.

Generally, in the OCM, $CH_4$ is first oxidatively converted into ethane ($C_2H_6$), and then into $C_2H_4$. $CH_4$ is activated heterogeneously on a catalyst surface, forming methyl free radicals (e.g., $CH_3\cdot$), which then couple in a gas phase to form $C_2H_6$. $C_2H_6$ subsequently undergoes dehydrogenation to form $C_2H_4$. An overall yield of desired $C_2$ hydrocarbons is reduced by non-selective reactions of methyl radicals with oxygen on the catalyst surface and/or in the gas phase, which produce (undesirable) carbon monoxide and carbon dioxide. Some of the best reported OCM outcomes encompass a ~20% conversion of methane and ~80% selectivity to desired $C_2$ hydrocarbons.

There are many catalyst systems developed for OCM processes, but such catalyst systems have many shortcomings. For example, conventional catalysts systems for OCM display catalyst performance problems, stemming from a need for high reaction temperatures. Thus, there is an ongoing need for the development of catalyst compositions for OCM processes.

BRIEF SUMMARY

Disclosed herein is an oxidative coupling of methane (OCM) catalyst composition doped with silver (Ag).

Also disclosed herein is an oxidative coupling of methane (OCM) catalyst composition comprising a lanthanum (III) and cerium (IV) mixture doped with silver (Ag).

Further disclosed herein is a supported oxidative coupling of methane (OCM) catalyst capable of catalyzing an OCM reaction, the supported OCM catalyst comprising silver (Ag) doped $Mn/Na_2WO_4$ and a metal oxide support, wherein the supported OCM catalyst has greater $CH_4$ conversion and $C_{2+}$ hydrocarbon selectivity as compared to the $CH_4$ conversion and $C_{2+}$ hydrocarbon selectivity, respectively, of an otherwise similar $Mn/Na_2WO_4$ metal oxide supported OCM catalyst that has not been doped with Ag.

Further disclosed herein is an oxidative coupling of methane (OCM) catalyst composition comprising one or more oxides doped with silver (Ag); wherein the one or more oxides comprises a single metal oxide, mixtures of single metal oxides, a mixed metal oxide, mixtures of mixed metal oxides, or combinations thereof; and wherein the one or more oxides is not $La_2O_3$ alone.

Further disclosed herein is a method of making an oxidative coupling of methane (OCM) catalyst composition comprising (a) calcining one or more oxides and/or oxide precursors to form one or more calcined oxides, wherein the one or more oxides comprises a single metal oxide, mixtures of single metal oxides, a mixed metal oxide, mixtures of mixed metal oxides, or combinations thereof, wherein the one or more oxides is not $La_2O_3$ alone, and wherein the oxide precursors comprise oxides, nitrates, carbonates, hydroxides, or combinations thereof, (b) doping the one or more calcined oxides with silver (Ag) to form the OCM catalyst composition, and (c) optionally thermally treating the OCM catalyst composition.

Further disclosed herein is a method for producing olefins comprising (a) introducing a reactant mixture to a reactor comprising an oxidative coupling of methane (OCM) catalyst composition, wherein the reactant mixture comprises methane ($CH_4$) and oxygen ($O_2$), wherein the OCM catalyst composition comprises one or more oxides doped with silver (Ag); wherein the one or more oxides comprises a single metal oxide, mixtures of single metal oxides, a mixed metal oxide, mixtures of mixed metal oxides, or combinations thereof, (b) allowing at least a portion of the reactant mixture to contact at least a portion of the OCM catalyst composition and react via an OCM reaction to form a product mixture comprising olefins, (c) recovering at least a portion of the product mixture from the reactor, and (d) recovering at least a portion of the olefins from the product mixture.

Further disclosed herein is a method of producing $C_{2+}$ hydrocarbons from an oxidative coupling of methane (OCM) reaction, the method comprising contacting a reactant feed that includes a methane containing gas and an oxygen containing gas with an OCM catalyst composition to produce a product stream comprising $C_{2+}$ hydrocarbons; wherein the OCM catalyst composition comprises one or more oxides doped with silver (Ag); wherein the one or more oxides comprises a single metal oxide, mixtures of single metal oxides, a mixed metal oxide, mixtures of mixed metal oxides, or combinations thereof; and wherein a selectivity to $C_{2+}$ hydrocarbons is from about 60% to about 90% at a reaction temperature of from about 200° C. to about 900° C.

Further disclosed herein is a system for producing $C_{2+}$ hydrocarbons, the system comprising (a) an inlet for a reactant feed comprising methane and oxygen, (b) a reaction zone that is configured to be in fluid communication with the inlet, wherein the reaction zone comprises an oxidative coupling of methane (OCM) catalyst composition; wherein the OCM catalyst composition comprises one or more oxides doped with silver (Ag); wherein the one or more oxides comprises a single metal oxide, mixtures of single metal oxides, a mixed metal oxide, mixtures of mixed metal oxides, or combinations thereof; wherein the reaction zone comprises the reactant feed and a product stream; and wherein a temperature of the reactant feed at the inlet, just prior to the inlet, during contact with the OCM catalyst composition, or combinations thereof is from about 200° C. to about 800° C., and (c) an outlet configured to be in fluid communication with the reaction zone and configured to remove the product stream comprising $C_{2+}$ hydrocarbons from the reaction zone.

Further disclosed herein is an oxidative coupling of methane (OCM) catalyst composition comprising a lanthanum (III) and cerium (IV) mixture doped with silver (Ag).

Further disclosed herein is a method of making an oxidative coupling of methane (OCM) catalyst composition comprising (a) forming a lanthanum (III) and cerium (III) mixture; (b) calcining the lanthanum (III) and cerium (III) mixture to form a lanthanum (III) and cerium (IV) mixture; (c) doping the lanthanum (III) and cerium (IV) mixture with silver (Ag) to form the OCM catalyst composition; and (d) optionally thermally treating the OCM catalyst composition.

Further disclosed herein is a method for producing olefins comprising (a) introducing a reactant mixture to a reactor comprising an oxidative coupling of methane (OCM) catalyst composition, wherein the reactant mixture comprises methane ($CH_4$) and oxygen ($O_2$), wherein the OCM catalyst composition comprises a lanthanum (III) and cerium (IV) mixture doped with silver (Ag); (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture.

Further disclosed herein is an oxidative coupling of methane (OCM) catalyst composition doped with silver (Ag).

Further disclosed herein is an oxidative coupling of methane (OCM) catalyst composition comprising silver (Ag).

Further disclosed herein is an oxidative coupling of methane (OCM) catalyst composition comprising silver (Ag) nanoparticles, Ag microparticles, Ag nanowires, or combinations thereof.

Further disclosed herein is a method of making an oxidative coupling of methane (OCM) catalyst composition comprising doping the OCM catalyst composition with silver (Ag); and optionally thermally treating the OCM catalyst composition.

Further disclosed herein is a method of making an oxidative coupling of methane (OCM) catalyst composition comprising adding silver (Ag) to the OCM catalyst composition; and optionally thermally treating the OCM catalyst composition.

Further disclosed herein is a method for producing olefins comprising (a) introducing a reactant mixture to a reactor comprising an oxidative coupling of methane (OCM) catalyst composition, wherein the reactant mixture comprises methane ($CH_4$) and oxygen ($O_2$), wherein the OCM catalyst composition is doped with silver (Ag), (b) allowing at least a portion of the reactant mixture to contact at least a portion of the OCM catalyst composition and react via an OCM reaction to form a product mixture comprising olefins, (c) recovering at least a portion of the product mixture from the reactor, and (d) recovering at least a portion of the olefins from the product mixture.

Further disclosed herein is a supported catalyst capable of catalyzing an oxidative couple of methane reaction, the supported catalyst comprising silver (Ag) doped $Mn/Na_2WO_4$ and a metal oxide support, wherein the catalyst has greater $CH_4$ conversion and $C_{2+}$ hydrocarbon selectivity as compared to the same $Mn/Na_2WO_4$ metal oxide supported catalyst that has not been doped with Ag.

BRIEF DESCRIPTION OF THE DRAWINGS

For a detailed description of the preferred embodiments of the disclosed methods, reference will now be made to the accompanying drawings in which.

DETAILED DESCRIPTION

Figure 1:
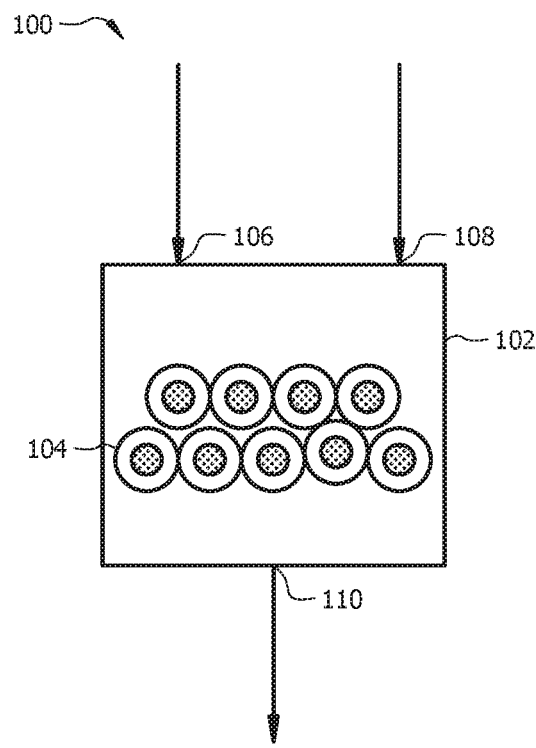
FIG. 1 displays a configuration of a system for producing $C_{2+}$ hydrocarbons comprising an oxidative coupling of methane (OCM) catalyst composition capable of catalyzing an OCM reaction.

Disclosed herein are oxidative coupling of methane (OCM) catalyst compositions and methods of making and using same. In an embodiment, an OCM catalyst composition can comprise one or more oxides doped with silver (Ag); wherein the one or more oxides comprises a single metal oxide, mixtures of single metal oxides, a mixed metal oxide, mixtures of mixed metal oxides, or combinations thereof; and wherein the one or more oxides is not $La_2O_3$ alone. In an embodiment, Ag can comprise Ag nanoparticles, Ag microparticles, Ag nanowires, and the like, or combinations thereof.

In an embodiment, a method of making an OCM catalyst composition can generally comprise the steps of (a) calcining one or more oxides and/or oxide precursors to form one or more calcined oxides, wherein the one or more oxides comprises a single metal oxide, mixtures of single metal oxides, a mixed metal oxide, mixtures of mixed metal oxides, or combinations thereof, wherein the one or more oxides is not $La_2O_3$ alone, and wherein the oxide precursors comprise oxides, nitrates, carbonates, hydroxides, any other suitable forms of precursors, and the like, or combinations thereof; (b) doping the one or more calcined oxides with Ag to form the OCM catalyst composition; and (c) optionally thermally treating the OCM catalyst composition. In some embodiments, the OCM catalyst composition can be formed into pellets by extrusion. In other embodiments, the OCM catalyst composition can be formed into tablets under pressure.

In an embodiment, a method for producing olefins can generally comprise the steps of (a) introducing a reactant mixture to a reactor comprising an OCM catalyst composition, wherein the reactant mixture comprises $CH_4$ and $O_2$, wherein the OCM catalyst composition comprises one or more oxides doped with Ag; wherein the one or more oxides comprises a single metal oxide, mixtures of single metal oxides, a mixed metal oxide, mixtures of mixed metal oxides, or combinations thereof; (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture. In an embodiment, the OCM reaction can be characterized by an ignition temperature that is decreased by from about 50° C. to about 500° C., when compared to an ignition temperature of an otherwise similar OCM reaction conducted in the presence of an OCM catalyst composition comprising one or more oxides without the Ag. In an embodiment, the OCM reaction can be characterized by a reaction temperature needed to achieve a 100% oxygen conversion that is decreased by from about 20° C. to about 500° C., when compared to a reaction temperature needed to achieve a 100% oxygen conversion of an otherwise similar OCM reaction conducted in the presence of an OCM catalyst composition comprising one or more oxides without the Ag.

Other than in the operating examples or where otherwise indicated, all numbers or expressions referring to quantities of ingredients, reaction conditions, and the like, used in the specification and claims are to be understood as modified in all instances by the term "about." In some aspects of the current disclosure, the terms "about" or "approximately" are defined as being close to as understood by one of ordinary skill in the art, and in one nonlimiting embodiment the terms are defined to be within 10%, alternatively within 5%, alternatively within 1%, or alternatively within 0.5%.

As used herein, the term "substantially" and its variations are defined as being largely but not necessarily wholly what is specified as understood by one of ordinary skill in the art, and in one nonlimiting aspect substantially refers to ranges within 10%, within 5%, within 1%, or within 0.5%.

Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an embodiment," "another embodiment," "other embodiments," "some embodiments," and so forth, means that a particular element (e.g., feature, structure, property, and/or characteristic) described in connection with the embodiment is included in at least an embodiment described herein, and may or may not be present in other embodiments. In addition, it is to be understood that the described element(s) can be combined in any suitable manner in the various embodiments.

The term "catalyst" means a substance which alters the rate of a chemical reaction. A catalyst may either increase the chemical reaction rate (i.e., a "positive catalyst") or decrease the reaction rate (i.e., a "negative catalyst"). Catalysts can participate in a reaction in a cyclic fashion such that the catalyst is cyclically regenerated. "Catalytic" means having the properties of a catalyst. For purposes of the disclosure herein the terms "catalyst" and "catalyst composition" are used interchangeably.

The term "dopant" or "doping agent" generally refers to one or more compounds and/or chemical species added to or incorporated within a catalyst to optimize catalytic performance (e.g., increase or decrease catalytic activity). As compared to an undoped catalyst, a doped catalyst may increase or decrease the selectivity, conversion, and/or yield of a reaction catalyzed by the doped catalyst. The terms "doped" and "promoted" are used interchangeably throughout the disclosure.

The term "conversion" as used herein refers to the mole fraction (i.e., mole percent) of a reactant converted to a product or products.

The term "selectivity" as used herein refers to the percent of converted reactant that went to a specified product, e.g., $C_{2+}$ hydrocarbon selectivity is the % of methane that formed ethane, ethylene and higher hydrocarbons (e.g., hydrocarbons having 2 or more carbon atoms).

In some aspects of the current disclosure, the term "nanowire" can refer to a nanowire structure having at least one diameter on the order of nanometers (e.g., between about 1 nanometer (nm) and about 100 nanometers) and an aspect ratio greater than about 10:1, unless otherwise specified herein. The "aspect ratio" of a nanowire refers the ratio of the actual length (L) of the nanowire to the diameter (D) of the nanowire.

In some aspects of the current disclosure, the term "nanoparticle" can refer to a particle having at least one diameter on the order of nanometers (e.g., between about 1 nm and about 100 nm), unless otherwise specified herein.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

The catalysts of the current disclosure can "comprise," "consist essentially of," or "consist of" particular ingredients, components, compositions, etc., disclosed throughout the specification. With respect to the transitional phase "consisting essentially of," in one nonlimiting aspect, a basic and novel characteristic of the catalyst is its capability to catalyze the production of $C_{2+}$ hydrocarbons from a gas that contains methane.

Unless defined otherwise, technical and scientific terms used herein have the same meaning as is commonly understood by one of skill in the art.

In an embodiment, a method for producing olefins can comprise introducing a reactant mixture to a reactor comprising an oxidative coupling of methane (OCM) catalyst composition to form a product mixture comprising olefins, wherein the reactant mixture comprises methane ($CH_4$) and oxygen ($O_2$), and wherein the OCM catalyst composition comprises one or more oxides doped with silver (Ag); wherein the one or more oxides comprises a single metal oxide, mixtures of single metal oxides, a mixed metal oxide, mixtures of mixed metal oxides, or combinations thereof.

In an embodiment, the reactant mixture can be a gaseous mixture. In an embodiment, the reactant mixture can comprise a hydrocarbon or mixtures of hydrocarbons, and oxygen. In some embodiments, the hydrocarbon or mixtures of hydrocarbons can comprise natural gas (e.g., $CH_4$), liquefied petroleum gas comprising $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), oxygenated hydrocarbons, biodiesel, alcohols, dimethyl ether, and the like, or combinations thereof. In an embodiment, the reactant mixture can comprise $CH_4$ and $O_2$.

In an embodiment, the $O_2$ used in the reactant mixture can be oxygen gas (which may be obtained via a membrane separation process), technical oxygen (which may contain some air), air, oxygen enriched air, and the like, or combinations thereof.

In an embodiment, the reactant mixture can be characterized by a methane to oxygen ($CH_4/O_2$) molar ratio of from about 1:1 to about 20:1, alternatively from about 1:1 to about 16:1, alternatively from about 2:1 to about 15:1, alternatively from about 2.5:1 to about 10:1, or alternatively from about 3:1 to about 9:1. As will be appreciated by one of skill in the art, and with the help of this disclosure, the greater the $CH_4/O_2$ molar ratio, the greater a selectivity to desired $C_2$ hydrocarbons, and the lower the $CH_4$ conversion.

In an embodiment, the reactant mixture can further comprise a diluent. The diluent is inert with respect to the OCM reaction, e.g., the diluent does not participate in the OCM reaction. In an embodiment, the diluent can comprise water, nitrogen, inert gases, and the like, or combinations thereof.

In an embodiment, the diluent can provide for heat control of the OCM reaction, e.g., the diluent can act as a heat sink. Generally, an inert compound (e.g., a diluent) can absorb some of the heat produced in the exothermic OCM reaction, without degrading or participating in any reaction (OCM or other reaction), thereby providing for controlling a temperature inside the reactor. As will be appreciated by one of skill in the art, and with the help of this disclosure, the diluent can be introduced to the reactor and/or as part of the reactant mixture (at a reactant mixture temperature), and as such the temperature of the diluent entering the reactor is much lower with the OCM catalyst composition disclosed herein, and the diluent can act as a better heat sink, thereby allowing for a better control of reaction temperature.

In an embodiment, the diluent can be present in the reactant mixture in an amount of from about 0.5% to about 80%, alternatively from about 5% to about 50%, or alternatively from about 10% to about 30%, based on the total volume of the reactant mixture.

In an embodiment, a method for producing olefins can comprise introducing the reactant mixture to a reactor, wherein the reactor comprises the OCM catalyst composition. In such embodiment, the reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In an embodiment, the reactor comprises an adiabatic reactor (e.g., a continuous flow adiabatic reactor).

In an embodiment, the OCM reaction can be characterized by an ignition temperature that is decreased by from about 50° C. to about 500° C., alternatively from about 75° C. to about 400° C., or alternatively from about 100° C. to about 300° C., when compared to an ignition temperature of an otherwise similar OCM reaction conducted in the presence of an OCM catalyst composition comprising one or more oxides without the Ag.

In an embodiment, the reactant mixture can be introduced to the reactor at a temperature of from about 200° C. to about 800° C., alternatively from about 225° C. to about 650° C., or alternatively from about 250° C. to about 500° C. As will be appreciated by one of skill in the art, and with the help of this disclosure, while the OCM reaction is exothermic, heat input is necessary for promoting the formation of methyl radicals from $CH_4$, as the C—H bonds of $CH_4$ are very stable, and the formation of methyl radicals from $CH_4$ is endothermic. Further, as will be appreciated by one of skill in the art, and with the help of this disclosure, with a lower ignition temperature catalyst, the heat input for the feed (e.g., reactant mixture) to start the reaction can be lowered, so energy can be saved.

In an embodiment, the reactant mixture can be introduced to the reactor at a temperature effective to promote an OCM reaction. In an embodiment, the OCM reaction can be characterized by an ignition temperature of from about 200° C. to about 800° C., alternatively from about 225° C. to about 650° C., alternatively from about 200° C. to about 500° C., alternatively from about 250° C. to about 500° C., alternatively from about 225° C. to about 475° C., or alternatively from about 250° C. to about 450° C.

In an embodiment, the OCM reaction can be characterized by a reaction temperature needed to achieve a 100% oxygen conversion that is decreased by from about 20° C. to about 500° C., alternatively from about 50° C. to about 400° C., or alternatively from about 75° C. to about 300° C. when compared to a reaction temperature needed to achieve a 100% oxygen conversion of an otherwise similar OCM reaction conducted in the presence of an OCM catalyst composition comprising one or more oxides without the Ag. Without wishing to be limited by theory, Ag promotion of the OCM catalyst increases catalyst activity and allows the OCM catalyst to reach the same oxygen conversion at a lower temperature. Further, without wishing to be limited by theory, Ag promotion of the OCM catalyst can shift the entire temperature profile of an OCM reaction towards lower temperatures, by increasing catalyst activity and facilitating reaching the same conversion (e.g., oxygen conversion, methane conversion, etc.) at lower temperatures.

In an embodiment, the reactor can comprise a catalyst bed comprising the OCM catalyst composition. In an embodiment, the catalyst bed can be characterized by a catalyst bed temperature of from about 200° C. to about 1,100° C., alternatively from about 225° C. to about 1,000° C., or alternatively from about 250° C. to about 900° C.

In an embodiment, the catalyst bed can be characterized by a catalyst bed temperature that is decreased by from about 20° C. to about 500° C., alternatively from about 50° C. to about 400° C., or alternatively from about 75° C. to about 300° C., when compared to a catalyst bed temperature of an otherwise similar catalyst bed comprising an OCM catalyst composition comprising one or more oxides without the Ag. As will be appreciated by one of skill in the art, and with the help of this disclosure, decreasing the ignition temperature for the OCM reaction leads to a decrease in the overall OCM reaction temperature, which further leads to a decreased catalyst bed temperature. Further, as will be appreciated by one of skill in the art, and with the help of this disclosure, a decrease in the temperature needed to achieve a 100% oxygen conversion leads to a decrease in the overall OCM reaction temperature, which further leads to a decreased catalyst bed temperature.

In an embodiment, the ignition temperature as disclosed herein (e.g., from about 200° C. to about 800° C.), along with an overall decrease in the reaction temperature (e.g., a temperature needed to achieve 100% oxygen conversion), can minimize hot spots formation within the reactor (e.g., hot spots formation in the catalyst bed). Generally, hot spots are portions (e.g., areas) of catalyst that exceed the reaction temperature, and such hot spots can lead to thermal deactivation of the catalyst and/or enhancement of deep oxidation reactions. Deep oxidation reactions include oxidation of methane to $CO_y$ (e.g., CO, $CO_2$). As will be appreciated by one of skill in the art, and with the help of this disclosure, a reduced ignition temperature (when compared to an ignition temperature of an otherwise similar OCM reaction conducted in the presence of an OCM catalyst composition comprising one or more oxides without the Ag) can allow for an overall reduced OCM reaction temperature or catalyst bed temperature, which in turn can minimize hot spots formation within the reactor. As will be appreciated by one of skill in the art, and with the help of this disclosure, a decrease in the ignition temperature for the OCM reaction and/or a decrease in the temperature needed to achieve a 100% oxygen conversion leads to a decrease in the overall OCM reaction temperature and to a decreased catalyst bed temperature, which further leads to a lower temperature of the hot spots, which will enhance the catalyst stability.

In an embodiment, the reactor can be characterized by a pressure of from about ambient pressure (e.g., atmospheric pressure) to about 500 psig, alternatively from about ambient pressure to about 200 psig, or alternatively from about ambient pressure to about 100 psig. In an embodiment, the method for producing olefins as disclosed herein can be carried out at ambient pressure.

In an embodiment, the reactor can be characterized by a gas hourly space velocity (GHSV) of from about 500 $h^{-1}$ to about 10,000,000 $h^{-1}$, alternatively from about 500 $h^{-1}$ to about 1,000,000 $h^{-1}$, alternatively from about 500 $h^{-1}$ to about 100,000 $h^{-1}$, alternatively from about 500 $h^{-1}$ to about 50,000 $h^{-1}$, alternatively from about 1,000 $h^{-1}$ to about 40,000 $h^{-1}$, or alternatively from about 1,500 $h^{-1}$ to about 25,000 $h^{-1}$. Generally, the GHSV relates a reactant (e.g., reactant mixture) gas flow rate to a reactor volume. GHSV is usually measured at standard temperature and pressure.

In an embodiment, the reactor can comprise an OCM catalyst composition comprising one or more oxides doped with silver (Ag); wherein the one or more oxides comprises a single metal oxide, mixtures of single metal oxides, a mixed metal oxide, mixtures of mixed metal oxides, or combinations thereof; and wherein the OCM catalyst composition catalyzes the OCM reaction (e.g., the catalyst catalyzes an oxidative coupling or conversion of $CH_4$ to olefins). For purposes of the disclosure herein the term "doped" refers to a physical bond and/or a chemical bond (e.g., a covalent bond) that is established between the one or more oxides and Ag. For example, Ag (e.g., Ag nanoparticles, microparticles, nanowires, etc.) can be retained onto the one or more oxides by electrostatic interactions, or other physical and/or chemical interactions.

In an embodiment, the one or more oxides can be present in the OCM catalyst composition in an amount of from about 0.01 wt. % to about 99.9 wt. %, alternatively from about 10.0 wt. % to about 90.0 wt. %, or alternatively from about 30.0 wt. % to about 70.0 wt. %, based on the total weight of the OCM catalyst composition. As will be appreciated by one of skill in the art, and with the help of this disclosure, a portion of the one or more oxides, in the presence of water, such as atmospheric moisture, can convert to hydroxides, and it is possible that the OCM catalyst composition will comprise some hydroxides, due to exposing the OCM catalyst composition comprising the one or more oxides to water (e.g., atmospheric moisture).

In an embodiment, the single metal oxide comprises one metal cation selected from the group consisting of alkali metal cations, alkaline earth metal cations, rare earth element cations, and cations of elements that can form oxides with redox properties. A single metal oxide can be characterized by the general formula $M_xO_y$; wherein M is the metal cation selected from the group consisting of alkali metal cations, alkaline earth metal cations, rare earth element cations, and cations of elements that can form oxides with redox properties; and wherein x and y are integers from 1 to 7, alternatively from 1 to 5, or alternatively from 1 to 3. A single metal oxide contains one and only one metal cation. Nonlimiting examples of single metal oxides suitable for use in the OCM catalyst compositions of the present disclosure include $CeO_2$, $Ce_2O_3$, $La_2O_3$, $Li_2O$, $Na_2O$, $Cs_2O$, $WO_3$, CaO, MgO, SrO, BaO, MnO, $W_2O_3$, $SnO_2$, $Yb_2O_3$ and $Sm_2O_3$.

In an embodiment, mixtures of single metal oxides can comprise two or more different single metal oxides, wherein the two or more different single metal oxides have been mixed together to form the mixture of single metal oxides. In an embodiment, mixtures of single metal oxides can comprise two or more different single metal oxides, wherein each single metal oxide can be selected from the group consisting of $CeO_2$, $Ce_2O_3$, $La_2O_3$, $Li_2O$, $Na_2O$, $Cs_2O$, $WO_3$, CaO, MgO, SrO, BaO, MnO, $W_2O_3$, $SnO_2$, $Yb_2O_3$ and $Sm_2O_3$. Nonlimiting examples of mixtures of single metal oxides suitable for use in the OCM catalyst compositions of the present disclosure include $La_2O_3$—$CeO_2$, CaO—MgO, CaO—BaO, MnO—$W_2O_3$, MnO—$W_2O_3$—$Na_2O$, $La_2O_3$—$CeO_2$—$Na_2O$, $La_2O_3$—$CeO_2$—CaO, $Na_2O$—MnO—$WO_3$—$La_2O_3$, $La_2O_3$—$CeO_2$—MnO—$WO_3$—SrO, and the like, or combinations thereof.

In an embodiment, the mixed metal oxide comprises two or more different metal cations, wherein each metal cation can be independently selected from the group consisting of alkali metal cations, alkaline earth metal cations, rare earth element cations, and cations of elements that can form oxides with redox properties. A mixed metal oxide can be characterized by the general formula $M^1_{x1}M^2_{x2}O_y$; wherein $M^1$ and $M^2$ are metal cations; wherein each of the $M^1$ and $M^2$ can be independently selected from the group consisting of alkali metal cations, alkaline earth metal cations, rare earth element cations, and cations of elements that can form oxides with redox properties; and wherein x1, x2 and y are integers from 1 to 15, alternatively from 1 to 10, or alternatively from 1 to 7. In some embodiments, $M^1$ and $M^2$ can be cations of different chemical elements, for example $M^1$ can be a lanthanum cation and $M^2$ can be a magnesium cation. In other embodiments, $M^1$ and $M^2$ can be different cations of the same chemical element, wherein $M^1$ and $M^2$ can have different oxidation states. For example, the mixed metal oxide can comprise $Mn_3O_4$, wherein $M^1$ can be a Mn (II) cation and $M^2$ can be a Mn (III) cation. Nonlimiting examples of mixed metal oxides suitable for use in the OCM catalyst compositions of the present disclosure include Mn/$Na_2WO_4$, $Mn_3O_4$, Li/MgO, $Li_2O$—SrO/$La_2O_3$, La/MgO, Na—Mn—O, $Na_2WO_4$, Ca/$CeO_2$, Sr/Mn—$Na_2WO_4$, and the like, or combinations thereof.

In an embodiment, mixtures of mixed metal oxides can comprise two or more different mixed metal oxides, wherein the two or more different mixed metal oxides have been mixed together to form the mixture of mixed metal oxides. In an embodiment, mixtures of mixed metal oxides can comprise two or more different mixed metal oxides, wherein each mixed metal oxide can be selected from the group consisting of Mn/$Na_2WO_4$, $Mn_3O_4$, Li/MgO, $Li_2O$/SrO, La/MgO, Na—Mn—O, $Na_2WO_4$, Ca/$CeO_2$ and Sr/Mn—$Na_2WO_4$. Nonlimiting examples of mixtures of mixed metal oxides suitable for use in the OCM catalyst compositions of the present disclosure include Mn/$Na_2WO_4$, Li/MgO, $Li_2O$—SrO/$La_2O_3$, La/MgO, Na—Mn—O, $Na_2WO_4$, Ca/$CeO_2$, Sr/Mn—$Na_2WO_4$, mixtures thereof, and the like, or combinations thereof.

In an embodiment, the OCM catalyst composition can comprise one or more oxides doped with Ag; wherein the one or more oxides can comprise alkali metal oxides, alkaline earth metal oxides, rare earth element oxides, oxides of elements that can form oxides with redox properties, or combinations thereof. As will be appreciated by one of skill in the art, and with the help of this disclosure, a mixed metal oxide can be regarded as belonging to more than one type of oxide category, when $M^1$ and $M^2$ are cations of different chemical elements. For example, $Na_2WO_4$ can be regarded as both an alkali metal oxide (e.g., sodium oxide) and an oxide of an element that can form oxides with redox properties (e.g., oxide of tungsten).

In an embodiment, the alkali metal oxides suitable for use in the OCM catalyst compositions of the present disclosure can comprise cations of lithium (Li), sodium (Na), potassium (K), rubidium (Rb), cesium (Cs), or combinations thereof.

In an embodiment, the alkaline earth metal oxides suitable for use in the OCM catalyst compositions of the present disclosure can comprise cations of magnesium (Mg), calcium (Ca), strontium (Sr), barium (Ba), or combinations thereof.

In an embodiment, the rare earth metal oxides suitable for use in the OCM catalyst compositions of the present disclosure can comprise cations of lanthanum (La), cerium (Ce), praseodymium (Pr), neodymium (Nd), samarium (Sm), europium (Eu), dysprosium (Dy), holmium (Ho), erbium (Er), ytterbium (Yb), and the like, or combinations thereof.

In an embodiment, the oxides of elements that can form oxides with redox properties suitable for use in the OCM catalyst compositions of the present disclosure can comprise cations of manganese (Mn), tungsten (W), vanadium (V), tin (Sn), antimony (Sb), phosphorus (P), arsenic (As), chromium (Cr), bismuth (Bi), gallium (Ga), rhenium (Re), lead (Pb), iron (Fe), cobalt (Co), nickel (Ni), copper (Cu), niobium (Nb), molybdenum (Mo), and the like, or combinations thereof.

In an embodiment, the OCM catalyst composition can comprise one or more oxides doped with Ag; wherein the one or more oxides can comprise $CeO_2$, $La_2O_3$, $La_2O_3$—$CeO_2$, Ca/$CeO_2$, Mn/$Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, MnO—$W_2O_3$, MnO—$W_2O_3$—$Na_2O$, MnO—$W_2O_3$—$Li_2O$, SrO/$La_2O_3$, $Ce_2O_3$, La/MgO, $La_2O_3$—$CeO_2$—$Na_2O$, $La_2O_3$—$CeO_2$—CaO, $Na_2O$—MnO—$WO_3$—$La_2O_3$, $La_2O_3$—$CeO_2$—MnO—$WO_3$—SrO, Na—Mn—$La_2O_3$/$Al_2O_3$, Na—Mn—O/$SiO_2$, $Na_2WO_4$—Mn/$SiO_2$, $Na_2WO_4$—Mn—O/$SiO_2$, Na/Mn/O, $Na_2WO_4$, $Mn_2O_3$/$Na_2WO_4$, $Mn_3O_4$/$Na_2WO_4$, $MnWO_4$/$Na_2WO_4$, $MnWO_4$/$Na_2WO_4$, Mn/$WO_4$, $Na_2WO_4$/Mn, Sr/Mn—$Na_2WO_4$, and the like, or combinations thereof. In some embodiments, the one or more oxides of the OCM catalyst composition is not $La_2O_3$ alone. In other embodiments, the one or more oxides of the OCM catalyst composition is $La_2O_3$ alone.

In an embodiment, the Ag can comprise Ag nanoparticles, Ag microparticles, Ag nanowires, and the like, or combinations thereof. In an embodiment, the OCM catalyst composition can comprise from about 0.1 wt. % to about 20.0 wt. %, alternatively from about 0.5 wt. % to about 10.0 wt. %, or alternatively from about 1.0 wt. % to about 5.0 wt. % Ag, based on the total weight of the OCM catalyst composition.

In an embodiment, the Ag comprises Ag nanoparticles, wherein the Ag nanoparticles can be characterized by an average size of from about 1 nm to about 500 nm, alternatively from about 2 nm to about 250 nm, alternatively from about 2.5 nm to about 100 nm, alternatively from about 5 nm to about 25 nm, or alternatively from about 10 nm to about 20 nm.

In an embodiment, the Ag comprises Ag microparticles, wherein the Ag microparticles can be characterized by an average size of from about 0.5 microns to about 50 microns, alternatively from about 0.5 microns to about 1.25 microns, alternatively from about 1 micron to about 25 microns, or alternatively from about 5 microns to about 10 microns.

In an embodiment, the Ag comprises Ag nanowires, wherein the Ag nanowires can be characterized by an average diameter of from about 1 nm to about 500 nm, alternatively from about 2 nm to about 100 nm, alternatively from about 2.5 nm to about 50 nm, or alternatively from about 25 nm to about 50 nm; and by an average length of from about 0.05 microns to about 50 microns, alternatively from about 1 micron to about 25 microns, alternatively from about 2 micron to about 50 microns, or alternatively from about 5 microns to about 10 microns.

In an embodiment, the OCM catalyst composition can comprise any suitable OCM catalyst doped with Ag. Without wishing to be limited by theory, Ag can promote a re-oxidation step for the OCM catalyst, which step is believed to be the rate determining step (as opposed to methyl radical formation) for the OCM reaction. Further, without wishing to be limited by theory, a catalyst promoter (e.g., Ag) that promotes the re-oxidation step for the OCM catalyst can lead to an overall lower OCM reaction temperature. Further, without wishing to be limited by theory, metal oxide catalysts can abstract a hydrogen radical from a methane molecule (that becomes a methyl radical), and such oxides can become reduced oxides, wherein an oxygen of the oxide becomes a hydroxyl group, thereby rendering the oxide reduced. Further, without wishing to be limited by theory, in the presence of the oxygen of the reactant mixture, the metal oxide catalyst can undergo a step of re-oxidation, wherein the hydroxyl of the reduced oxide can form water, and wherein Ag promotes the catalyst re-oxidation step. As will be appreciated by one of skill in the art, and with the help of this disclosure, Ag promotes as well the step wherein the metal oxide catalysts can abstract a hydrogen radical from a methane molecule that becomes a methyl radical (in addition to promoting the re-oxidations step). The re-oxidation step for OCM catalysts is described in more detail in Sinev et al., J. Natural Gas Chemistry, 18 (2009) p. 273, which is incorporated by reference herein in its entirety.

In an embodiment, the OCM catalyst compositions suitable for use in the present disclosure can be supported OCM catalyst compositions and/or unsupported OCM catalyst compositions. In some embodiments, the supported OCM catalyst compositions can comprise a support, wherein the support can be catalytically active (e.g., the support can catalyze an OCM reaction). For example, the catalytically active support can comprise a metal oxide support, such as MgO. In other embodiments, the supported OCM catalyst compositions can comprise a support, wherein the support can be catalytically inactive (e.g., the support cannot catalyze an OCM reaction), such as $SiO_2$. In yet other embodiments, the supported OCM catalyst compositions can comprise a catalytically active support and a catalytically inactive support. As will be appreciated by one of skill in the art, and with the help of this disclosure, the support can be purchased or can be prepared by using any suitable methodology, such as for example precipitation/co-precipitation, sol-gel techniques, templates/surface derivatized metal oxides synthesis, solid-state synthesis of mixed metal oxides, microemulsion techniques, solvothermal techniques, sonochemical techniques, combustion synthesis, etc.

In some embodiments, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), calcium oxide (CaO), strontium oxide (SrO), zirconium oxide ($ZrO_2$), zinc oxide (ZnO), lithium aluminum oxide ($LiAlO_2$), magnesium aluminum oxide ($MgAlO_4$), manganese oxides (MnO, $MnO_2$, $Mn_3O_4$), lanthanum oxide ($La_2O_3$), activated carbon, silica gel, zeolites, activated clays, silicon carbide (SiC), diatomaceous earth, magnesia, aluminosilicates, calcium aluminate, carbonates, $MgCO_3$, $CaCO_3$, $SrCO_3$, $BaCO_3$, $Y_2(CO_3)_3$, $La_2(CO_3)_3$, and the like, or combinations thereof. In an embodiment, the support can comprise MgO, $Al_2O_3$, $SiO_2$, $ZrO_2$, and the like, or combinations thereof.

In an embodiment, the OCM catalyst composition can further comprise a support, wherein at least a portion of the OCM catalyst composition contacts, coats, is embedded in, is supported by, and/or is distributed throughout at least a portion of the support. In such embodiment, the support can be in the form of particles, pellets, monoliths, foams, honeycombs, and the like, or combinations thereof. Nonlimiting examples of support particle shapes include cylindrical, discoidal, spherical, tabular, ellipsoidal, equant, irregular, cubic, acicular, and the like, or combinations thereof.

In an embodiment, the OCM catalyst composition can further comprise a porous support. As will be appreciated by one of skill in the art, and with the help of this disclosure, a porous material (e.g., support, tablet, pellet, etc.) can provide for an enhanced surface area of contact between the OCM catalyst composition and the reactant mixture, which in turn would result in a higher $CH_4$ conversion to $CH_3$.

In some embodiments, the OCM catalyst composition can be introduced as a powder to the reactor. In other embodiments, the OCM catalyst composition can be first formed into pellets and/or tablets and then introduced to the reactor.

In an embodiment, the OCM catalyst composition tablets can exclude a binder. In an embodiment, the OCM catalyst composition pellets can comprise a binder, such as for example clays (e.g., aluminosilicates), amorphous aluminophosphate, alumina, silica, titania, zirconia, and the like, or combinations thereof.

In an embodiment, the OCM catalyst composition can be characterized by a hot spot temperature ($T_{hot}$). Generally, the $T_{hot}$ of a catalyst represents the highest temperature in the catalyst bed. The higher the $T_{hot}$, the higher the chance the catalyst loses its catalytic ability due to thermal degradation of the catalyst. Thermal degradation of a catalyst can involve a variety of distinct processes, such as sintering of catalytically active sites (e.g., agglomeration of catalytically active sites with a reduction in catalytically active surface area); evaporation of promoters from the catalyst; and the like; or combinations thereof. In an embodiment, loss of catalytic activity can be related to a loss of methane and/or oxygen conversion, wherein oxygen conversion can be reduced by from about 100% to about 95%, alternatively from about 100% to about 98.0%, or alternatively from about 100% to 99.5%, within 2,000 hours of catalyst use. In such embodiment, the loss of catalytic activity can be due to a loss of some components from the catalyst, fusing of active material to a non-active catalyst phase, and the like, or combinations thereof.

In an embodiment, the $T_{hot}$ of an OCM catalyst as disclosed herein can be decreased by from about 20° C. to about 1,000° C., alternatively from about 50° C. to about 750° C., or alternatively from about 75° C. to about 500° C., when compared to $T_{hot}$ of an otherwise similar OCM catalyst comprising one or more oxides without the Ag. The decrease in $T_{hot}$ can be due to a lower ignition temperature and/or an overall lower reaction temperature (e.g., a temperature needed to achieve 100% oxygen conversion), as described herein. In an embodiment, the OCM catalyst composition as disclosed herein can be characterized by a stability that is increased when compared to a stability of an otherwise similar OCM catalyst composition comprising one or more oxides without the Ag. As will be appreciated by one of skill in the art, and with the help of this disclosure, the lower the ignition temperature and/or the lower the overall reaction temperature, the lower the hot spots temperature, and the greater the stability and selectivity of the catalyst. The enhanced stability of the OCM catalyst composition as disclosed herein can lead to enhanced selectivity. As will be appreciated by one of skill in the art, and with the help of this disclosure, the hot spots can decrease catalyst selectivity.

In an embodiment, the OCM catalyst composition as disclosed herein can be characterized by a catalyst life that can be increased by from about 2 to about 100 times, alternatively from about 5 to about 95 times, or alternatively from about 10 to about 90 times when compared to a catalyst life of an otherwise similar OCM catalyst composition comprising one or more oxides without the Ag. For purposes of the disclosure herein, the catalyst life of a catalyst refers to the amount of time that the catalyst provides its catalytic performance without losing it.

In an embodiment, the OCM catalyst composition can be made by using any suitable methodology. In an embodiment, a base or "parent" OCM catalyst composition (for example, an OCM catalyst such as a lanthanum-cerium OCM catalyst composition, a sodium-manganese OCM catalyst composition, a manganese-sodium-tungsten OCM catalyst composition, or any other suitable type of OCM catalyst composition) may be modified by the addition of silver as described herein. In an embodiment, an OCM catalyst composition may comprise silver (Ag), and the Ag and added via any suitable technique such as admixing, bulk mixing, granulation, deposition, sputtering, compounding, extruding, and the like, or combinations thereof. In an embodiment, an oxidative coupling of methane (OCM) catalyst composition may be doped with silver (Ag). In some embodiments, the added Ag has a predefined particle shape and size that survives incorporation into the OCM catalyst composition. In such embodiment, the Ag may comprise Ag nanoparticles, Ag microparticles, Ag nanowires, or combinations thereof.

In an embodiment, a method of making an OCM catalyst composition as disclosed herein can comprise contacting the OCM catalyst composition with Ag, doping the OCM catalyst with Ag, or otherwise adding Ag to the OCM catalyst; and optionally thermally treating the OCM catalyst composition. The Ag may comprise Ag nanoparticles, Ag microparticles, Ag nanowires, or combinations thereof. The method may further comprise forming the OCM catalyst composition into pellets by extrusion. The method may further comprise forming the OCM catalyst composition into tablets under pressure. The method may further comprise contacting the OCM catalyst composition with a support. A modified OCM catalyst comprising Ag may be obtained by such methods.

In an embodiment, a method of making an OCM catalyst composition can comprise calcining one or more oxides and/or oxide precursors to form one or more calcined oxides, wherein the one or more oxides comprises a single metal oxide, mixtures of single metal oxides, a mixed metal oxide, mixtures of mixed metal oxides, or combinations thereof. In an embodiment, an oxide precursor can be any suitable compound that can produce the one or more oxides as disclosed herein subsequent to a calcining step. Nonlimiting examples of oxide precursors include oxides, nitrates, carbonates, hydroxides, any other suitable forms of precursors, and the like, or combinations thereof. For example, $La(NO_3)_3$ can be calcined to yield $La_2O_3$. As another example, $Ce(NO_3)_3$ can be calcined to yield $CeO_2$. As will be appreciated by one of skill in the art, and with the help of this disclosure, a calcining step can change the oxidation state of cations in the one or more oxides and/or oxide precursors.

In an embodiment, the one or more oxides and/or oxide precursors can be calcined at a temperature of from about 500° C. to about 900° C., alternatively from about 550° C. to about 800° C., or alternatively from about 600° C. to about 700° C., to yield one or more calcined oxides. In an embodiment, the one or more oxides and/or oxide precursors can be calcined for a time period of from about 1 hour to about 12 hours, alternatively from about 2.5 hours to about 10 hours, or alternatively from about 4 hours to about 6 hours.

In an embodiment, a method of making an OCM catalyst composition can comprise doping the one or more calcined oxides with silver (Ag) to form the OCM catalyst composition. The Ag comprises Ag nanoparticles, Ag microparticles, Ag nanowires, and the like, or combinations thereof.

In such embodiment, the one or more calcined oxides can be contacted with a Ag aqueous dispersion to form a Ag, and one or more calcined oxides aqueous dispersion. Generally, an aqueous dispersion refers to a two-phased system that is made up of extremely fine particles (e.g., Ag particles, such as Ag nanoparticles, Ag microparticles, Ag nanowires, etc.; and/or one or more calcined oxides particles) that are uniformly distributed throughout water or an aqueous medium. The Ag, and one or more calcined oxides aqueous dispersion can be stirred or agitated to obtain an uniform aqueous dispersion.

In an embodiment, at least a portion of the Ag, and one or more calcined oxides aqueous dispersion can be dried at a temperature of from about 75° C. to about 150° C., alternatively from about 90° C. to about 140° C., or alternatively from about 100° C. to about 125° C., to yield the OCM catalyst composition (e.g., one or more oxides doped with Ag). In such embodiment, the Ag, and one or more calcined oxides aqueous dispersion can be dried for a time period of from about 4 hours to about 24 hours, alternatively from about 8 hours to about 16 hours, or alternatively from about 10 hours to about 14 hours.

In some embodiments, the one or more oxides and/or the one or more calcined oxides can be contacted with a Ag doping agent, for example with an aqueous solution of a Ag doping agent, to form Ag doped oxides and/or Ag doped calcined oxides. The Ag doped oxides and/or Ag doped calcined oxides can be further dried, calcined, and/or thermally treated as disclosed herein for oxides doped with metallic Ag (e.g., Ag nanoparticles, Ag microparticles, Ag nanowires, and the like, or combinations thereof) to produce the OCM catalyst composition. Nonlimiting examples of Ag doping agents suitable for use in the present disclosure include silver salts, silver acetate, silver acetylide, silver arsenate, silver azide, silver behenate, silver bromate, silver bromide, silver carbonate, silver chlorate, silver chloride, silver chromate, silver cyanate, silver cyanide, silver dichromate, silver fulminate, silver hexafluorophosphate, silver iodate, silver iodide, silver molybdate, silver nitrate, silver nitride, silver nitrite, silver oxalate, silver oxide, silver perchlorate, silver permanganate, silver perrhenate, silver phosphate, silver proteinate, silver selenite, silver subfluoride, silver sulfadiazine, silver sulfate, silver sulfide, silver sulfite, silver telluride, silver tetrafluoroborate, silver thiocyanate, silver trifluoromethanesulfonate, silver fluoride, silver selenide, silver oxide, and the like, or combinations thereof.

In an embodiment, a method of making an OCM catalyst composition can comprise optionally thermally treating the OCM catalyst composition. In an embodiment, at least a portion of the OCM catalyst composition (e.g., one or more oxides doped with Ag) can be thermally treated at a temperature of from about 150° C. to about 600° C., alternatively from about 200° C. to about 550° C., or alternatively from about 250° C. to about 500° C., to yield a thermally treated OCM catalyst composition. In such embodiment, the one or more oxides doped with Ag can be thermally treated for a time period of from about 2 hours to about 24 hours, alternatively from about 4 hours to about 16 hours, or alternatively from about 5 hours to about 12 hours.

In some embodiments, a method of making an OCM catalyst composition can further comprise contacting the OCM catalyst composition with a support to yield a supported catalyst (e.g., an OCM supported catalyst, an OCM supported catalyst composition, etc.).

In other embodiments, (i) the one or more calcined oxides can be formed as previously disclosed herein in the presence of a support, and/or (ii) the one or more calcined oxides can be doped with Ag as previously disclosed herein in the presence of a support; to yield an OCM catalyst composition (e.g., a supported catalyst, an OCM supported catalyst, an OCM supported catalyst composition, etc.).

In an embodiment, a method of making an OCM catalyst composition can further comprise forming the OCM catalyst composition into pellets by extrusion. In such embodiment, the OCM catalyst composition (e.g., powder) and a binder can be introduced to an extruder to form pellets. The extruder can be a single screw extruder, a twin screw extruder, or any other suitable extrusion machines, and the like.

In an embodiment, a method of making an OCM catalyst composition can further comprise forming the OCM catalyst composition into tablets under pressure. In an embodiment, tablets of the OCM catalyst composition can be formed in a tablet press by applying an appropriate amount of pressure (e.g., force in the form of pressure) to the OCM catalyst composition (e.g., powder), wherein OCM catalyst composition particles (e.g., powder particles) are compacted together.

In an embodiment, a method for producing olefins can comprise allowing at least a portion of the reactant mixture to contact at least a portion of the OCM catalyst composition and react via an OCM reaction to form a product mixture comprising olefins.

In an embodiment, the product mixture can comprise $C_{2+}$ hydrocarbons, wherein the $C_{2+}$ hydrocarbons can comprise $C_2$ hydrocarbons and $C_3$ hydrocarbons. In an embodiment, the $C_{2+}$ hydrocarbons can further comprise $C_4$ hydrocarbons ($C_4s$), such as for example butane, iso-butane, n-butane, butylene, etc. Reactant conversions (e.g., methane conversion, oxygen conversion, etc.) and selectivities to certain products (e.g., selectivity to $C_{2+}$ hydrocarbons, selectivity to $C_2$ hydrocarbons, selectivity to ethylene, etc.) can be calculated as disclosed in more detail in the Examples section, for example such as described in equations (1)-(3).

In an embodiment, equal to or greater than about 10 mol %, alternatively equal to or greater than about 30 mol %, or alternatively equal to or greater than about 50 mol % of the methane in the reactant mixture can be converted to $C_{2+}$ hydrocarbons. Generally, a selectivity to a certain product refers to the amount of that particular product formed divided by the total amount of products formed.

In an embodiment, the $C_2$ hydrocarbons can comprise ethylene ($C_2H_4$) and ethane ($C_2H_6$). In some embodiments, a $C_2H_4$ content of the product mixture can be higher than a $C_2H_6$ content of the product mixture. In an embodiment, the $C_2$ hydrocarbons can further comprise acetylene ($C_2H_2$).

In an embodiment, equal to or greater than about 40 mol %, alternatively equal to or greater than about 70 mol %, or alternatively equal to or greater than about 90 mol % of selectivity to $C_2$ hydrocarbons can be obtained.

In an embodiment, equal to or greater than about 20 mol %, alternatively equal to or greater than about 50 mol %, or alternatively equal to or greater than about 80 mol % of selectivity to ethylene can be obtained.

In an embodiment, the $C_3$ hydrocarbons can comprise propylene ($C_3H_6$) and propane ($C_3H_8$).

In an embodiment, the product mixture comprises coupling products, deep oxidation products (e.g., CO and $CO_2$), and unreacted methane. In an embodiment, the coupling products can comprise olefins (e.g., alkenes, characterized by a general formula $C_nH_{2n}$) and paraffins (e.g., alkanes, characterized by a general formula $C_nH_{2n+2}$).

In an embodiment, equal to or greater than about 20 mol %, alternatively equal to or greater than about 55 mol %, or alternatively equal to or greater than about 85 mol % of selectivity to olefins can be obtained.

In an embodiment, a method for producing olefins can further comprise minimizing deep oxidation of methane to CO and $CO_2$. In an embodiment, the product mixture can comprise less than about 15 mol % CO and $CO_2$, alternatively less than about 10 mol % CO and $CO_2$, or alternatively less than about 5 mol % CO and $CO_2$. As will be appreciated by one of skill in the art, and with the help of this disclosure, within certain temperature ranges, the higher the reaction temperature, the higher the selectivity to desired products (e.g., olefins, hydrocarbons, etc.); however, generally, extremely high reaction temperatures (e.g., over about 1,000° C.) can lead to an increase in deep oxidation products (e.g., CO, $CO_2$). Further, as will be appreciated by one of skill in the art, and with the help of this disclosure, the novel OCM catalyst composition as disclosed herein allows for a reduced ignition temperature, thus allowing for a reduced OCM reaction temperature, thereby minimizing deep oxidation reactions.

In an embodiment, the OCM catalyst composition as disclosed herein (e.g., unsupported catalyst and/or supported catalyst capable of catalyzing an OCM reaction) can have a greater methane conversion and $C_{2+}$ hydrocarbon selectivity as compared to the same OCM catalyst composition comprising one or more oxides that has not been doped with Ag. Generally, a conversion of a reagent or reactant refers to the percentage (usually mol %) of reagent that reacted to both undesired and desired products, based on the total amount (e.g., moles) of reagent present before any reaction took place.

In some aspects, the methane conversion in the presence of an OCM catalyst composition as disclosed herein (e.g., unsupported catalyst and/or supported catalyst capable of catalyzing an OCM reaction) can be from about 10% to about 60%, alternatively from about 12.5% to about 50%, or alternatively from about 15% to about 45%.

In an embodiment, a method for producing olefins can comprise recovering at least a portion of the product mixture from the reactor, wherein the product mixture can be collected as an outlet gas mixture from the reactor. In an embodiment, a method for producing olefins can comprise recovering at least a portion of the $C_2$ hydrocarbons from the product mixture. In an embodiment, the product mixture can comprise $C_{2+}$ hydrocarbons (including olefins), unreacted methane, and optionally a diluent. The water produced from the OCM reaction and the water used as a diluent (if water diluent is used) can be separated from the product mixture prior to separating any of the other product mixture components. For example, by cooling down the product mixture to a temperature where the water condenses (e.g., below 100° C. at ambient pressure), the water can be removed from the product mixture, by using a flash chamber for example.

In an embodiment, at least a portion of the $C_{2+}$ hydrocarbons can be separated (e.g., recovered) from the product mixture to yield recovered $C_{2+}$ hydrocarbons. The $C_{2+}$ hydrocarbons can be separated from the product mixture by using any suitable separation technique. In an embodiment, at least a portion of the $C_{2+}$ hydrocarbons can be separated from the product mixture by distillation (e.g., cryogenic distillation).

In an embodiment, at least a portion of the recovered $C_{2+}$ hydrocarbons can be used for ethylene production. In some embodiments, at least a portion of ethylene can be separated from the product mixture (e.g., from the $C_{2+}$ hydrocarbons, from the recovered $C_{2+}$ hydrocarbons) to yield recovered ethylene and recovered hydrocarbons, by using any suitable separation technique (e.g., distillation). In other embodiments, at least a portion of the recovered hydrocarbons (e.g., recovered $C_{2+}$ hydrocarbons after olefin separation, such as separation of $C_2H_4$ and $C_3H_6$) can be converted to ethylene, for example by a conventional steam cracking process.

In an embodiment, a method for producing olefins can comprise recovering at least a portion of the olefins from the product mixture. In an embodiment, at least a portion of the olefins can be separated from the product mixture by distillation (e.g., cryogenic distillation). As will be appreciated by one of skill in the art, and with the help of this disclosure, the olefins are generally individually separated from their paraffin counterparts by distillation (e.g., cryogenic distillation). For example ethylene can be separated from ethane by distillation (e.g., cryogenic distillation). As another example, propylene can be separated from propane by distillation (e.g., cryogenic distillation).

In an embodiment, at least a portion of the unreacted methane can be separated from the product mixture to yield recovered methane. Methane can be separated from the product mixture by using any suitable separation technique, such as for example distillation (e.g., cryogenic distillation). In an embodiment, at least a portion of the recovered methane can be recycled to the reactant mixture.

In an embodiment, an OCM catalyst composition can comprise (i) from about 0.1 wt. % to about 20 wt. % Ag; and (ii) from about 45.0 wt. % to about 99.0 wt. % lanthanum (III), and from about 0.9 wt. % to about 50.0 wt. % cerium (IV); wherein lanthanum (III) comprises $La_2O_3$ and optionally $La(OH)_3$; and wherein cerium (IV) comprises $CeO_2$. As will be appreciated by one of skill in the art, and with the help of this disclosure, a portion of $La_2O_3$, in the presence of water, such as atmospheric moisture, can convert to $La(OH)_3$, and it is possible that the OCM catalyst composition will comprise some $La(OH)_3$, due to exposing the OCM catalyst composition comprising $La_2O_3$ to water (e.g., atmospheric moisture).

In an embodiment, an OCM catalyst composition can comprise a $La_2O_3$ and $CeO_2$ mixture doped with Ag nanoparticles, wherein the Ag nanoparticles can be characterized by an average size of from about 10 nm to about 20 nm. In such embodiment, the OCM catalyst composition can further comprise $La(OH)_3$.

In an embodiment, an OCM catalyst composition can comprise a $La_2O_3$ and $CeO_2$ mixture doped with Ag microparticles (e.g., Ag powder), wherein the Ag microparticles can be characterized by an average size of from about 0.5 microns to about 1.25 microns. In such embodiment, the OCM catalyst composition can further comprise $La(OH)_3$.

In an embodiment, an OCM catalyst composition can comprise a $La_2O_3$ and $CeO_2$ mixture doped with Ag nanowires, wherein the Ag nanowires can be characterized by an average diameter of from about 25 nm to about 50 nm; and by an average length of from about 2 microns to about 50 microns. In such embodiment, the OCM catalyst composition can further comprise $La(OH)_3$.

In an embodiment, an OCM catalyst composition can comprise a silver (Ag) doped $Mn/Na_2WO_4$ and a metal oxide support (e.g., silver doped $Mn/Na_2WO_4$ metal oxide supported OCM catalyst, silver doped $Mn/Na_2WO_4$ metal oxide supported OCM catalyst composition, silver doped $Mn/Na_2WO_4$ metal oxide supported catalyst, silver doped $Mn/Na_2WO_4$ metal oxide supported catalyst composition, etc.), wherein the catalyst has greater methane conversion and $C_{2+}$ hydrocarbon selectivity as compared to the same $Mn/Na_2WO_4$ metal oxide supported catalyst that has not been doped with Ag. The Ag may comprise Ag nanoparticles, Ag microparticles, Ag nanowires, or combinations thereof.

In an embodiment, a method of producing $C_{2+}$ hydrocarbons from an OCM reaction can comprise contacting a reactant mixture (e.g., a reactant feed that includes a methane containing gas and an oxygen containing gas) with an OCM catalyst composition to produce a product mixture (e.g., a product stream) comprising $C_{2+}$ hydrocarbons; wherein the OCM catalyst composition comprises one or more oxides doped with Ag; wherein the one or more oxides comprises a single metal oxide, mixtures of single metal oxides, a mixed metal oxide, mixtures of mixed metal oxides, or combinations thereof; and wherein a selectivity to $C_{2+}$ hydrocarbons is from about 60% to about 90% at a reaction temperature of from about 200° C. to about 900° C.

In an embodiment, a method for producing olefins comprises (a) introducing a reactant mixture to a reactor comprising an OCM catalyst composition, wherein the reactant mixture comprises $CH_4$ and $O_2$, wherein the OCM catalyst composition is doped with Ag, and wherein the OCM catalyst composition comprises one or more oxides doped with Ag; wherein the one or more oxides comprises a single metal oxide, mixtures of single metal oxides, a mixed metal oxide, mixtures of mixed metal oxides, or combinations thereof; (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture. The Ag may comprise Ag nanoparticles, Ag microparticles, Ag nanowires, or combinations thereof. The OCM reaction may be characterized by an ignition temperature of from about 200° C. to about 800° C. The OCM reaction may be characterized by an ignition temperature that is decreased by from about 50° C. to about 500° C., when compared to an ignition temperature of an otherwise similar OCM reaction conducted in the presence of an OCM catalyst composition without the Ag. The reactor may comprise a catalyst bed comprising the OCM catalyst composition, wherein the catalyst bed is characterized by a catalyst bed temperature of from about 200° C. to about 1,100° C. The reactor may comprise a catalyst bed comprising the OCM catalyst composition, wherein the catalyst bed is characterized by a catalyst bed temperature that is decreased by from about 20° C. to about 500° C., when compared to a catalyst bed temperature of an otherwise similar catalyst bed comprising an OCM catalyst composition without the Ag. The reactor may comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, or combinations thereof. The reactant mixture may further comprise a diluent. The diluent may comprise water, nitrogen, inert gases, or combinations thereof. Equal to or greater than about 10 mol % of the methane in the reactant mixture may be converted to $C_{2+}$ hydrocarbons. Equal to or greater than about 20 mol % of selectivity to olefins may be obtained. Equal to or greater than about 40 mol % of selectivity to $C_2$ hydrocarbons may be obtained. Equal to or greater than about 20 mol % of selectivity to ethylene may be obtained. The product mixture may comprise less than about 15 mol % CO and $CO_2$. The method may further comprise minimizing deep oxidation of methane to CO and $CO_2$.

In an embodiment, a system for producing $C_{2+}$ hydrocarbons can comprise (a) an inlet for a reactant feed (e.g., reactant mixture) comprising methane and oxygen; (b) a reaction zone that is configured to be in fluid communication with the inlet, wherein the reaction zone comprises an OCM catalyst composition; wherein the OCM catalyst composition comprises one or more oxides doped with Ag; wherein the one or more oxides comprises a single metal oxide, mixtures of single metal oxides, a mixed metal oxide, mixtures of mixed metal oxides, or combinations thereof; wherein the reaction zone comprises the reactant mixture and a product stream; and wherein a temperature of the reactant feed at the inlet, just prior to the inlet, during contact with the OCM catalyst composition, or combinations thereof is from about 200° C. to about 800° C.; and (c) an outlet configured to be in fluid communication with the reaction zone and configured to remove the product stream comprising $C_{2+}$ hydrocarbons from the reaction zone.

Ag—La—Ce Catalyst

In an embodiment, a method for producing olefins can comprise introducing a reactant mixture to a reactor comprising an oxidative coupling of methane (OCM) catalyst composition to form a product mixture comprising olefins, wherein the reactant mixture comprises methane ($CH_4$) and oxygen ($O_2$), and wherein the OCM catalyst composition comprises a lanthanum (III) and cerium (IV) mixture doped with silver (Ag) (i.e., Ag—La—Ce catalyst, Ag—La—Ce catalyst composition). The reactant mixture contacts the Ag—La—Ce catalyst composition to form a product mixture comprising $C_{2+}$ hydrocarbons (e.g., olefins).

In an embodiment, the reactant mixture that is contacted with the Ag—La—Ce catalyst composition can be a gaseous mixture. In such embodiment, the reactant mixture can comprise a hydrocarbon or mixtures of hydrocarbons, and oxygen; wherein the hydrocarbon or mixtures of hydrocarbons can comprise natural gas (e.g., $CH_4$), liquefied petroleum gas comprising $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), oxygenated hydrocarbons, biodiesel, alcohols, dimethyl ether, and the like, or combinations thereof. In an embodiment, the reactant mixture that is contacted with the Ag—La—Ce catalyst composition can comprise $CH_4$ and $O_2$.

In an embodiment, the $O_2$ used in the reactant mixture that is contacted with the Ag—La—Ce catalyst composition can be oxygen gas (which may be obtained via a membrane separation process), technical oxygen (which may contain some air), air, oxygen enriched air, and the like, or combinations thereof.

In an embodiment, the reactant mixture that is contacted with the Ag—La—Ce catalyst composition can be characterized by a methane to oxygen molar ratio of from about 1:1 to about 20:1, alternatively from about 1:1 to about 16:1, alternatively from about 2:1 to about 15:1, alternatively from about 2.5:1 to about 10:1, or alternatively from about 3:1 to about 9:1.

In an embodiment, the reactant mixture that is contacted with the Ag—La—Ce catalyst composition can further comprise a diluent; wherein the diluent is inert with respect to the OCM reaction, e.g., the diluent does not participate in the OCM reaction; and wherein the diluent can comprise water, nitrogen, inert gases, and the like, or combinations thereof.

In an embodiment, the diluent can provide for heat control of the OCM reaction conducted in the presence of the Ag—La—Ce catalyst composition, e.g., the diluent can act as a heat sink. An inert compound (e.g., a diluent) can absorb some of the heat produced in the exothermic OCM reaction conducted in the presence of the Ag—La—Ce catalyst composition, without degrading or participating in any reaction (OCM or other reaction), thereby providing for controlling a temperature inside the reactor. As will be appreciated by one of skill in the art, and with the help of this disclosure, the diluent can be introduced to the reactor and/or as part of the reactant mixture that is contacted with the Ag—La—Ce catalyst composition (at a reactant mixture temperature), and as such the temperature of the diluent entering the reactor is much lower with the Ag—La—Ce catalyst composition disclosed herein, and the diluent can act as a better heat sink, thereby allowing for a better control of the reaction temperature.

In an embodiment, the diluent can be present in the reactant mixture that is contacted with the Ag—La—Ce catalyst composition in an amount of from about 0.5% to about 80%, alternatively from about 5% to about 50%, or alternatively from about 10% to about 30%, based on the total volume of the reactant mixture.

In an embodiment, a method for producing olefins can comprise introducing the reactant mixture to a reactor, wherein the reactor comprises the Ag—La—Ce catalyst composition. In such embodiment, the reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In an embodiment, the reactor comprising the Ag—La—Ce catalyst composition can be an adiabatic reactor.

In an embodiment, the reactor comprising the Ag—La—Ce catalyst composition can be characterized by a GHSV of from about 500 $h^{-1}$ to about 10,000,000 $h^{-1}$, alternatively from about 500 $h^{-1}$ to about 1,000,000 $h^{-1}$, alternatively from about 500 $h^{-1}$ to about 100,000 $h^{-1}$, alternatively from about 500 h$^{-1}$ to about 50,000 h$^{-1}$, alternatively from about 1,000 h$^{-1}$ to about 40,000 h$^{-1}$, or alternatively from about 1,500 h$^{-1}$ to about 25,000 h$^{-1}$.

In an embodiment, the OCM reaction conducted in the presence of the Ag—La—Ce catalyst composition can be characterized by an ignition temperature that is decreased by from about 50° C. to about 300° C., alternatively from about 75° C. to about 275° C., or alternatively from about 100° C. to about 250° C., when compared to an ignition temperature of an otherwise similar OCM reaction conducted in the presence of an OCM catalyst composition comprising a lanthanum (III) and cerium (IV) mixture without the Ag.

In an embodiment, the reactant mixture that is contacted with the Ag—La—Ce catalyst composition can be introduced to the reactor at an ignition temperature of from about 200° C. to about 500° C., alternatively from about 225° C. to about 475° C., or alternatively from about 250° C. to about 450° C. As will be appreciated by one of skill in the art, and with the help of this disclosure, while the OCM reaction conducted in the presence of the Ag—La—Ce catalyst composition is exothermic, heat input is necessary for promoting the formation of methyl radicals from $CH_4$, as the C—H bonds of $CH_4$ are very stable, and the formation of methyl radicals from $CH_4$ is endothermic. Further, as will be appreciated by one of skill in the art, and with the help of this disclosure, with a lower ignition temperature catalyst (e.g., Ag—La—Ce catalyst), the heat input for the feed (e.g., reactant mixture) to start the reaction can be lowered, so energy can be saved.

In an embodiment, the reactant mixture that is contacted with the Ag—La—Ce catalyst composition can be introduced to the reactor at a temperature effective to promote an OCM reaction. In an embodiment, the OCM reaction conducted in the presence of the Ag—La—Ce catalyst composition can be characterized by an ignition temperature of from about 200° C. to about 500° C., alternatively from about 225° C. to about 475° C., or alternatively from about 250° C. to about 450° C.

In an embodiment, the reactor can comprise a catalyst bed comprising the Ag—La—Ce catalyst composition. In such embodiment, the catalyst bed can be characterized by a catalyst bed temperature of from about 200° C. to about 1,100° C., alternatively from about 225° C. to about 1,000° C., or alternatively from about 250° C. to about 900° C.

In an embodiment, the catalyst bed comprising the Ag—La—Ce catalyst composition can be characterized by a catalyst bed temperature that is decreased by from about 50° C. to about 300° C., alternatively from about 75° C. to about 275° C., or alternatively from about 100° C. to about 250° C., when compared to a catalyst bed temperature of an otherwise similar catalyst bed comprising an OCM catalyst composition comprising a lanthanum (III) and cerium (IV) mixture without the Ag.

In an embodiment, the ignition temperature as disclosed herein (e.g., from about 200° C. to about) 500° C can minimize hot spots formation within the reactor comprising the Ag—La—Ce catalyst composition (e.g., hot spots formation in the catalyst bed comprising the Ag—La—Ce catalyst composition). Generally, hot spots are portions (e.g., areas) of catalyst (e.g., Ag—La—Ce catalyst composition) that exceed the reaction temperature, and such hot spots can lead to thermal deactivation of the catalyst and/or enhancement of deep oxidation reactions. As will be appreciated by one of skill in the art, and with the help of this disclosure, a reduced ignition temperature of an OCM reaction conducted in the presence of the Ag—La—Ce catalyst composition (when compared to an ignition temperature of an otherwise similar OCM reaction conducted in the presence of an OCM catalyst composition comprising a lanthanum (III) and cerium (IV) mixture without the Ag) can allow for an overall reduced OCM reaction temperature or catalyst bed temperature, which in turn can minimize hot spots formation within the reactor.

In an embodiment, the reactor comprising the Ag—La—Ce catalyst composition can be characterized by a pressure of from about ambient pressure (e.g., atmospheric pressure) to about 500 psig, alternatively from about ambient pressure to about 200 psig, or alternatively from about ambient pressure to about 100 psig. In an embodiment, the method for producing olefins by using the Ag—La—Ce catalyst composition as disclosed herein can be carried out at ambient pressure.

In an embodiment, the reactor can comprise an OCM catalyst composition comprising a lanthanum (III) (La(III)) and cerium (IV) (Ce(IV)) mixture doped with silver (Ag), wherein the OCM catalyst composition catalyzes the OCM reaction (e.g., the catalyst catalyzes an oxidative coupling or conversion of $CH_4$ to olefins).

In an embodiment, the Ag of the Ag—La—Ce catalyst composition comprises Ag nanoparticles, Ag microparticles, Ag nanowires, and the like, or combinations thereof. In an embodiment, the Ag—La—Ce catalyst composition can comprise from about 0.1 wt. % to about 20.0 wt. %, alternatively from about 0.5 wt. % to about 10.0 wt. %, or alternatively from about 1.0 wt. % to about 5.0 wt. % Ag, based on the total weight of the Ag—La—Ce catalyst composition.

In an embodiment, the Ag of the Ag—La—Ce catalyst composition comprises Ag nanoparticles, wherein the Ag nanoparticles can be characterized by an average size of from about 1 nm to about 500 nm, alternatively from about 2 nm to about 250 nm, alternatively from about 2.5 nm to about 100 nm, alternatively from about 5 nm to about 25 nm, or alternatively from about 10 nm to about 20 nm.

In an embodiment, the Ag of the Ag—La—Ce catalyst composition comprises Ag microparticles, wherein the Ag microparticles can be characterized by an average size of from about 0.5 microns to about 50 microns, alternatively from about 0.5 microns to about 1.25 microns, alternatively from about 1 micron to about 25 microns, or alternatively from about 5 microns to about 10 microns.

In an embodiment, the Ag of the Ag—La—Ce catalyst composition comprises Ag nanowires, wherein the Ag nanowires can be characterized by an average diameter of from about 1 nm to about 500 nm, alternatively from about 2 nm to about 100 nm, alternatively from about 2.5 nm to about 50 nm, or alternatively from about 25 nm to about 50 nm; and by an average length of from about 0.05 microns to about 50 microns, alternatively from about 1 micron to about 25 microns, alternatively from about 2 micron to about 50 microns, or alternatively from about 5 microns to about 10 microns.

In an embodiment, the Ag—La—Ce catalyst composition can comprise from about 45.0 wt. % to about 99.0 wt. %, alternatively from about 50.0 wt. % to about 99.0 wt. %, alternatively from about 75.0 wt. % to about 98.0 wt. %, or alternatively from about 85.0 wt. % to about 95.0 wt. % La(III), based on the total weight of the OCM catalyst composition. In such embodiment, La(III) can comprise $La_2O_3$, and optionally $La(OH)_3$. As will be appreciated by one of skill in the art, and with the help of this disclosure, a portion of $La_2O_3$, in the presence of water, such as atmospheric moisture, can convert to $La(OH)_3$, and it is possible that the OCM catalyst composition will comprise some La(OH)$_3$, due to exposing the Ag—La—Ce catalyst composition comprising La$_2$O$_3$ to water (e.g., atmospheric moisture).

In an embodiment, the Ag—La—Ce catalyst composition can comprise from about 0.5 wt. % to about 50.0 wt. %, alternatively from about 0.6 wt. % to about 50.0 wt. %, alternatively from about 0.7 wt. % to about 50.0 wt. %, alternatively from about 0.8 wt. % to about 50.0 wt. %, alternatively from about 0.9 wt. % to about 50.0 wt. %, alternatively from about 1.0 wt. % to about 50.0 wt. %, alternatively from about 2.5 wt. % to about 25.0 wt. %, or alternatively from about 5.0 wt. % to about 15.0 wt. % Ce(IV), based on the total weight of the Ag—La—Ce catalyst composition. In such embodiment, Ce(IV) can comprise CeO$_2$.

In an embodiment, La(III) and Ce(IV) mixture can comprise a La(III) and Ce(IV) powder, wherein the La(III) and Ce(IV) powder comprises La(III) and Ce(IV) powder particles. Without wishing to be limited by theory, it is expected that the La(III) and Ce(IV) powder particles comprise both La(III) and Ce(IV) (e.g., each powder particle is heterogeneous, in that it should contain both La$_2$O$_3$ and CeO$_2$), due to the way the La(III) and Ce(IV) mixture is synthesized, which synthesis will be described in more detail later herein. Further, without wishing to be limited by theory, while it is possible that some powder particles will only comprise La(III) or Ce(IV), however, the amount of powder particles comprising only La(III) or only Ce(IV) in the La(III) and Ce(IV) mixture is expected to be extremely low, e.g., the La(III) and Ce(IV) mixture might comprise less than about 10 wt. %, alternatively less than about 5 wt. %, alternatively less than about 1 wt. %, alternatively less than about 0.5 wt. %, or alternatively less than about 0.1 wt. %, powder particles comprising only La(III) or only Ce(IV), based on the total weight of the La(III) and Ce(IV) mixture.

In an embodiment, the La(III) and Ce(IV) mixture is doped with Ag. In an embodiment, the La(III) and Ce(IV) mixture doped with Ag can be a powder. As will be appreciated by one of skill in the art, and with the help of this disclosure, doping a La(III) and Ce(IV) powder with Ag can result in a powder (e.g., Ag—La—Ce catalyst composition powder). For purposes of the disclosure herein the term "doped" refers to a physical bond and/or a chemical bond (e.g., a covalent bond) that is established between La(III) and Ce(IV) mixture particles and Ag. For example, one or more Ag particles (e.g., nanoparticles, microparticles, nanowires, etc.) can be retained onto one or more La(III) and Ce(IV) mixture particles (e.g., La(III) and Ce(IV) powder particles) by electrostatic interactions, or other physical and/or chemical interactions. As will be appreciated by one of skill in the art, and with the help of this disclosure, each Ag particle can be doping (e.g., can be retained onto) one or more La(III) and Ce(IV) mixture particles. Further, as will be appreciated by one of skill in the art, and with the help of this disclosure, each La(III) and Ce(IV) mixture particle can be doped with (e.g., can retain) one or more Ag particles. Further, as will be appreciated by one of skill in the art, and with the help of this disclosure, it is possible that some La(III) and Ce(IV) mixture particles are not doped with Ag, and/or that some Ag particles are not retained onto (e.g., doping) La(III) and Ce(IV) mixture particles. Without wishing to be limited by theory, Ag particles not doping La(III) and Ce(IV) mixture particles, as well as La(III) and Ce(IV) mixture particles not doped with Ag, are expected to exhibit some catalytic properties with respect to the OCM reaction, although not to the same extent to which the La(III) and Ce(IV) mixture particles doped with Ag exhibit some catalytic properties with respect to the OCM reaction. The amount of powder particles comprising only Ag in the La(III) and Ce(IV) mixture doped with Ag is expected to be extremely low, e.g., the La(III) and Ce(IV) mixture doped with Ag might comprise less than about 10 wt. %, alternatively less than about 5 wt. %, alternatively less than about 1 wt. %, alternatively less than about 0.5 wt. %, or alternatively less than about 0.1 wt. %, powder particles comprising only Ag, based on the total weight of the La(III) and Ce(IV) mixture doped with Ag.

In an embodiment, the Ag—La—Ce catalyst composition suitable for use in the present disclosure can be supported Ag—La—Ce catalyst composition and/or unsupported Ag—La—Ce catalyst composition. In some embodiments, the supported Ag—La—Ce catalyst composition can comprise a support, wherein the support can be catalytically active (e.g., the support can catalyze an OCM reaction). In other embodiments, the supported Ag—La—Ce catalyst composition can comprise a support, wherein the support can be catalytically inactive (e.g., the support cannot catalyze an OCM reaction). In yet other embodiments, the supported Ag—La—Ce catalyst composition can comprise a catalytically active support and a catalytically inactive support. Nonlimiting examples of a support suitable for use in the present disclosure in supported Ag—La—Ce catalyst compositions include MgO, Al$_2$O$_3$, SiO$_2$, ZrO$_2$, and the like, or combinations thereof. As will be appreciated by one of skill in the art, and with the help of this disclosure, the support used in supported Ag—La—Ce catalyst compositions can be purchased or can be prepared by using any suitable methodology, such as for example precipitation/co-precipitation, sol-gel techniques, templates/surface derivatized metal oxides synthesis, solid-state synthesis of mixed metal oxides, microemulsion techniques, solvothermal techniques, sonochemical techniques, combustion synthesis, etc.

In an embodiment, the Ag—La—Ce catalyst composition can further comprise a support, wherein at least a portion of the Ag—La—Ce catalyst composition contacts, coats, is embedded in, is supported by, and/or is distributed throughout at least a portion of the support. In such embodiment, the support can be in the form of particles, pellets, monoliths, foams, honeycombs, and the like, or combinations thereof. Nonlimiting examples of support particle shapes suitable for use in supported Ag—La—Ce catalyst compositions include cylindrical, discoidal, spherical, tabular, ellipsoidal, equant, irregular, cubic, acicular, and the like, or combinations thereof.

In an embodiment, the Ag—La—Ce catalyst composition can further comprise a porous support. As will be appreciated by one of skill in the art, and with the help of this disclosure, a porous material (e.g., support, tablet, pellet, etc.) can provide for an enhanced surface area of contact between the Ag—La—Ce catalyst composition and the reactant mixture, which in turn would result in a higher CH$_4$ conversion to CH$_3$.

In some embodiments, the Ag—La—Ce catalyst composition can be introduced as a powder to the reactor. In other embodiments, the Ag—La—Ce catalyst composition can be first formed into pellets and/or tablets and then introduced to the reactor.

In an embodiment, the Ag—La—Ce catalyst composition tablets can exclude a binder. In an embodiment, the Ag—La—Ce catalyst composition pellets can comprise a binder, such as for example clays (e.g., aluminosilicates), amorphous aluminophosphate, alumina, silica, titania, zirconia, and the like, or combinations thereof.

In an embodiment, the Ag—La—Ce catalyst composition can be characterized by a hot spot temperature ($T_{hot}$). Generally, the $T_{hot}$ of a catalyst represents the highest temperature in the catalyst bed comprising the Ag—La—Ce catalyst composition. The higher the $T_{hot}$, the higher the chance the Ag—La—Ce catalyst loses its catalytic ability due to thermal degradation of the Ag—La—Ce catalyst. Thermal degradation of a Ag—La—Ce catalyst can involve a variety of distinct processes, such as sintering of catalytically active sites (e.g., agglomeration of catalytically active sites with a reduction in catalytically active surface area); evaporation of promoters from the catalyst and the like; or combinations thereof. In an embodiment, loss of catalytic activity of a Ag—La—Ce catalyst composition can be related to a loss of methane and/or oxygen conversion, wherein oxygen conversion can be reduced by from about 100% to about 95%, alternatively from about 100% to about 98.0%, or alternatively from about 100% to 99.5%, within 2,000 hours of catalyst use. In such embodiment, the loss of catalytic activity can be due to a loss of some components from the Ag—La—Ce catalyst composition, fusing of active material to a non-active catalyst phase, and the like, or combinations thereof.

In an embodiment, the Ag—La—Ce catalyst composition can be characterized by a catalyst life that can be increased by from about 2 to about 100 times, when compared to a catalyst life of an otherwise similar OCM catalyst composition comprising a La(III) and Ce(III) mixture without the Ag. For purposes of the disclosure herein, the life of a Ag—La—Ce catalyst refers to the amount of time that the Ag—La—Ce catalyst provides its catalytic performance without losing it.

In an embodiment, the Ag—La—Ce catalyst composition can be made by using any suitable methodology. In an embodiment, a method of making an Ag—La—Ce catalyst composition can comprise forming a La(III) and Ce(III) mixture.

In an embodiment, forming a La(III) and Ce(III) mixture can comprise contacting a La(III) aqueous solution with a Ce(III) aqueous solution to yield a La(III) and Ce(III) aqueous solution. In an embodiment, the La(III) aqueous solution can be prepared by dissolving $La(NO_3)_3 \cdot 6H_2O$, $La_2(CO_3)_3$—$H_2O$, $LaCl_3 \cdot xH_2O$, and the like, or combinations thereof, in water or any suitable aqueous medium. In an embodiment, the Ce(III) aqueous solution can be prepared by dissolving $Ce(NO_3)_3 \cdot 6H_2O$, $Ce_2(CO_3)_3$—$H_2O$, $CeCl_3 \cdot xH_2O$, and the like, or combinations thereof, in water or any suitable aqueous medium.

In an embodiment, at least a portion of the La(III) and Ce(III) aqueous solution can be heated to a temperature of from about 50° C. to about 99° C., alternatively from about 65° C. to about 95° C., or alternatively from about 80° C. to about 90° C., to yield a heated La(III) and Ce(III) aqueous solution. In such embodiment, the La(III) and Ce(III) aqueous solution can be heated for a time period of from about 15 minutes to about 4 hours, alternatively from about 1 hour to about 3 hours, or alternatively from about 1.5 hours to about 2.5 hours.

In an embodiment, at least a portion of the heated La(III) and Ce(III) aqueous solution can be dried at a temperature of from about 100° C. to about 150° C., alternatively from about 110° C. to about 140° C., or alternatively from about 120° C. to about 130° C., to yield a La(III) and Ce(III) mixture, wherein the La(III) and Ce(III) mixture can comprise $La(NO_3)_3$ and $Ce(NO_3)_3$. In such embodiment, the heated La(III) and Ce(III) aqueous solution can be dried for a time period of from about 4 hours to about 24 hours, alternatively from about 8 hours to about 16 hours, or alternatively from about 10 hours to about 14 hours.

In an embodiment, a method of making a Ag—La—Ce catalyst composition can comprise calcining the lanthanum (III) and cerium (III) mixture to form a lanthanum (III) and cerium (IV) mixture. In an embodiment, the La(III) and Ce(III) mixture can be calcined at a temperature of from about 500° C. to about 700° C., alternatively from about 550° C. to about 675° C., or alternatively from about 600° C. to about 650° C., to yield a La(III) and Ce(IV) mixture, wherein the La(III) and Ce(IV) mixture can comprise $La_2O_3$, $La(OH)_3$ and $CeO_2$. Without wishing to be limited by theory, during calcining the lanthanum (III) and cerium (III) mixture, the nitrates (e.g., $La(NO_3)_3$ and $Ce(NO_3)_3$) are converted into the corresponding oxides (e.g., $La_2O_3$, $La(OH)_3$ and $CeO_2$, respectively). In an embodiment, the La(III) and Ce(III) mixture can be calcined for a time period of from about 1 hour to about 12 hours, alternatively from about 2.5 hours to about 10 hours, or alternatively from about 4 hours to about 6 hours. In an embodiment, the La(III) and Ce(IV) mixture comprises a powder.

In an embodiment, a method of making a Ag—La—Ce catalyst composition can comprise doping the La(III) and Ce(IV) mixture with Ag to form the Ag—La—Ce catalyst composition. The Ag used for doping the La(III) and Ce(IV) mixture comprises Ag nanoparticles, Ag microparticles, Ag nanowires, and the like, or combinations thereof. In such embodiment, the La(III) and Ce(IV) mixture can be contacted with a Ag aqueous dispersion to form a Ag, La(III) and Ce(IV) aqueous dispersion. Generally, an aqueous dispersion refers to a two-phased system that is made up of extremely fine particles (e.g., Ag particles, such as Ag nanoparticles, Ag microparticles, Ag nanowires, etc.; and/or La(III) and Ce(IV) mixture particles) that are uniformly distributed throughout water or an aqueous medium. The Ag, La(III) and Ce(IV) aqueous dispersion can be stirred or agitated to obtain an uniform aqueous dispersion.

In an embodiment, at least a portion of the Ag, La(III) and Ce(IV) aqueous dispersion can be dried at a temperature of from about 75° C. to about 150° C., alternatively from about 90° C. to about 140° C., or alternatively from about 100° C. to about 125° C., to yield a La(III) and Ce(IV) mixture doped with Ag. In such embodiment, the Ag, La(III) and Ce(IV) aqueous dispersion can be dried for a time period of from about 4 hours to about 24 hours, alternatively from about 8 hours to about 16 hours, or alternatively from about 10 hours to about 14 hours. In an embodiment, the La(III) and Ce(IV) mixture doped with Ag comprises a powder.

In an embodiment, a method of making a Ag—La—Ce catalyst composition can comprise optionally thermally treating the Ag—La—Ce catalyst composition. In an embodiment, at least a portion of the Ag—La—Ce catalyst composition (e.g., La(III) and Ce(IV) mixture doped with Ag) can be thermally treated at a temperature of from about 150° C. to about 600° C., alternatively from about 200° C. to about 550° C., or alternatively from about 250° C. to about 500° C., to yield a thermally treated Ag—La—Ce catalyst composition. In such embodiment, the La(III) and Ce(IV) mixture doped with Ag can be thermally treated for a time period of from about 2 hours to about 24 hours, alternatively from about 4 hours to about 16 hours, or alternatively from about 5 hours to about 12 hours.

In some embodiments, a method of making a Ag—La—Ce catalyst composition can further comprise contacting the Ag—La—Ce catalyst composition with a support to yield a supported catalyst (e.g., a Ag—La—Ce supported catalyst, a Ag—La—Ce supported catalyst composition, etc.).

In other embodiments, the La(III) and Ce(III) mixture can be formed as previously disclosed herein in the presence of a support; and/or (ii) the La(III) and Ce(IV) mixture can be doped with Ag as previously disclosed herein in the presence of a support; to yield a Ag—La—Ce catalyst composition (e.g., a supported catalyst, a Ag—La—Ce supported catalyst, a Ag—La—Ce supported catalyst composition, etc.).

In an embodiment, a method of making a Ag—La—Ce catalyst composition can further comprise forming the Ag—La—Ce catalyst composition into pellets by extrusion. In such embodiment, the Ag—La—Ce catalyst composition (e.g., powder) and a binder can be introduced to an extruder to form pellets; wherein the extruder can be a single screw extruder, a twin screw extruder, or any other suitable extrusion machines, and the like.

In an embodiment, a method of making a Ag—La—Ce catalyst composition can further comprise forming the Ag—La—Ce catalyst composition into tablets under pressure. In an embodiment, tablets of the Ag—La—Ce catalyst composition can be formed in a tablet press by applying an appropriate amount of pressure (e.g., force in the form of pressure) to the Ag—La—Ce catalyst composition (e.g., powder), wherein Ag—La—Ce catalyst composition particles (e.g., powder particles) are compacted together (e.g., in a manner similar to forming pharmaceutical tablets of various compositions).

In an embodiment, a method for producing olefins can comprise allowing at least a portion of the reactant mixture to contact at least a portion of the Ag—La—Ce catalyst composition and react via an OCM reaction to form a product mixture comprising olefins.

In an embodiment, the product mixture formed in the presence of the Ag—La—Ce catalyst composition can comprise $C_{2+}$ hydrocarbons, wherein the $C_{2+}$ hydrocarbons can comprise $C_2$ hydrocarbons and $C_3$ hydrocarbons; wherein the $C_{2+}$ hydrocarbons can further comprise $C_4$ hydrocarbons ($C_4$s), such as for example butane, iso-butane, n-butane, butylene, etc. Reactant conversions (e.g., methane conversion, oxygen conversion, etc.) and selectivities to certain products (e.g., selectivity to $C_{2+}$ hydrocarbons, selectivity to $C_2$ hydrocarbons, selectivity to ethylene, etc.) in the presence of the Ag—La—Ce catalyst composition can be calculated as disclosed in more detail in the Examples section, for example such as described in equations (1)-(3).

In an embodiment, equal to or greater than about 10 mol %, alternatively equal to or greater than about 30 mol %, or alternatively equal to or greater than about 50 mol % of the methane in the reactant mixture can be converted to $C_{2+}$ hydrocarbons in the presence of the Ag—La—Ce catalyst composition. Generally, a selectivity to a certain product refers to the amount of that particular product formed divided by the total amount of products formed, for example in the presence of the Ag—La—Ce catalyst composition.

In an embodiment, the $C_2$ hydrocarbons formed in the presence of the Ag—La—Ce catalyst composition can comprise ethylene ($C_2H_4$) and ethane ($C_2H_6$). In some embodiments, a $C_2H_4$ content of the product mixture formed in the presence of the Ag—La—Ce catalyst composition can be higher than a $C_2H_6$ content of the product mixture. In an embodiment, the $C_2$ hydrocarbons formed in the presence of the Ag—La—Ce catalyst composition can further comprise acetylene ($C_2H_2$).

In an embodiment, equal to or greater than about 40 mol %, alternatively equal to or greater than about 70 mol %, or alternatively equal to or greater than about 90 mol % of selectivity to $C_2$ hydrocarbons can be obtained in the presence of the Ag—La—Ce catalyst composition.

In an embodiment, equal to or greater than about 20 mol %, alternatively equal to or greater than about 50 mol %, or alternatively equal to or greater than about 80 mol % of selectivity to ethylene can be obtained in the presence of the Ag—La—Ce catalyst composition.

In an embodiment, the $C_3$ hydrocarbons formed in the presence of the Ag—La—Ce catalyst composition can comprise propylene ($C_3H_6$) and propane ($C_3H_8$).

In an embodiment, the product mixture formed in the presence of the Ag—La—Ce catalyst composition comprises coupling products, partial oxidation products (e.g., partial conversion products, such as CO, $H_2$, $CO_2$), and unreacted methane; wherein the coupling products can comprise olefins (e.g., alkenes, characterized by a general formula $C_nH_{2n}$) and paraffins (e.g., alkanes, characterized by a general formula $C_nH_{2n+2}$).

In an embodiment, equal to or greater than about 20 mol %, alternatively equal to or greater than about 55 mol %, or alternatively equal to or greater than about 85 mol % of selectivity to olefins can be obtained in the presence of the Ag—La—Ce catalyst composition.

In some aspects, the methane conversion in the presence of a Ag—La—Ce catalyst composition can be from about 10% to about 60%, alternatively from about 12.5% to about 50%, or alternatively from about 15% to about 45%.

In an embodiment, a method for producing olefins in the presence of the Ag—La—Ce catalyst composition can further comprise minimizing deep oxidation of methane to $CO_2$. In an embodiment, the product mixture formed in the presence of the Ag—La—Ce catalyst composition can comprise less than about 15 mol % $CO_2$, alternatively less than about 10 mol % $CO_2$, or alternatively less than about 5 mol % $CO_2$. As will be appreciated by one of skill in the art, and with the help of this disclosure, within certain temperature ranges, the higher the reaction temperature, the higher the selectivity to desired products (e.g., olefins, hydrocarbons, etc.); however, generally, extremely high reaction temperatures (e.g., over about 1,000° C.) can lead to an increase in deep oxidation products (e.g., CO, $CO_2$). Further, as will be appreciated by one of skill in the art, and with the help of this disclosure, the novel Ag—La—Ce catalyst composition as disclosed herein allows for a reduced ignition temperature, thus allowing for a reduced OCM reaction temperature, thereby minimizing deep oxidation reactions.

In an embodiment, a method for producing olefins in the presence of the Ag—La—Ce catalyst composition can comprise recovering at least a portion of the product mixture from the reactor, wherein the product mixture can be collected as an outlet gas mixture from the reactor. In an embodiment, a method for producing olefins in the presence of the Ag—La—Ce catalyst composition can comprise recovering at least a portion of the $C_2$ hydrocarbons from the product mixture. In an embodiment, the product mixture formed in the presence of the Ag—La—Ce catalyst composition can comprise $C_{2+}$ hydrocarbons (including olefins), unreacted methane, and optionally a diluent. The water produced from the OCM reaction conducted in the presence of the Ag—La—Ce catalyst composition and the water used as a diluent (if water diluent is used) can be separated from the product mixture prior to separating any of the other product mixture components. For example, by cooling down the product mixture formed in the presence of the Ag—La—Ce catalyst composition to a temperature where the water condenses (e.g., below 100° C. at ambient pressure), the water can be removed from the product mixture, by using a flash chamber for example.

In an embodiment, at least a portion of the $C_{2+}$ hydrocarbons formed in the presence of the Ag—La—Ce catalyst composition can be separated (e.g., recovered) from the product mixture to yield recovered $C_{2+}$ hydrocarbons. The $C_{2+}$ hydrocarbons formed in the presence of the Ag—La—Ce catalyst composition can be separated from the product mixture by using any suitable separation technique. In an embodiment, at least a portion of the $C_{2+}$ hydrocarbons formed in the presence of the Ag—La—Ce catalyst composition can be separated from the product mixture by distillation (e.g., cryogenic distillation).

In an embodiment, at least a portion of the recovered $C_{2+}$ hydrocarbons formed in the presence of the Ag—La—Ce catalyst composition can be used for ethylene production. In some embodiments, at least a portion of ethylene formed in the presence of the Ag—La—Ce catalyst composition can be separated from the product mixture (e.g., from the $C_{2+}$ hydrocarbons, from the recovered $C_{2+}$ hydrocarbons) to yield recovered ethylene and recovered hydrocarbons, by using any suitable separation technique (e.g., distillation). In other embodiments, at least a portion of the recovered hydrocarbons (e.g., recovered $C_{2+}$ hydrocarbons after olefin separation, such as separation of $C_2H_4$ and $C_3H_6$) from a process conducted in the presence of the Ag—La—Ce catalyst composition can be converted to ethylene, for example by a conventional steam cracking process.

In an embodiment, a method for producing olefins in the presence of the Ag—La—Ce catalyst composition can comprise recovering at least a portion of the olefins from the product mixture. In an embodiment, at least a portion of the olefins formed in the presence of the Ag—La—Ce catalyst composition can be separated from the product mixture by distillation (e.g., cryogenic distillation). As will be appreciated by one of skill in the art, and with the help of this disclosure, the olefins formed in the presence of the Ag—La—Ce catalyst composition are generally individually separated from their paraffin counterparts by distillation (e.g., cryogenic distillation). For example ethylene can be separated from ethane by distillation (e.g., cryogenic distillation). As another example, propylene can be separated from propane by distillation (e.g., cryogenic distillation).

In an embodiment, at least a portion of the unreacted methane can be separated from the product mixture formed in the presence of the Ag—La—Ce catalyst composition to yield recovered methane. Methane can be separated from the product mixture formed in the presence of the Ag—La—Ce catalyst composition by using any suitable separation technique, such as for example distillation (e.g., cryogenic distillation). In an embodiment, at least a portion of the recovered methane can be recycled to the reactant mixture that is contacted with the Ag—La—Ce catalyst composition.

In an embodiment, a Ag—La—Ce catalyst composition can comprise a $La_2O_3$ and $CeO_2$ mixture doped with Ag nanoparticles, wherein the Ag nanoparticles can be characterized by an average size of from about 10 nm to about 20 nm. In such embodiment, the Ag—La—Ce catalyst composition can further comprise $La(OH)_3$.

In an embodiment, a Ag—La—Ce catalyst composition can comprise a $La_2O_3$ and $CeO_2$ mixture doped with Ag microparticles (e.g., Ag powder), wherein the Ag microparticles can be characterized by an average size of from about 0.5 microns to about 1.25 microns. In such embodiment, the Ag—La—Ce catalyst composition can further comprise $La(OH)_3$.

In an embodiment, a Ag—La—Ce catalyst composition can comprise a $La_2O_3$ and $CeO_2$ mixture doped with Ag nanowires, wherein the Ag nanowires can be characterized by an average diameter of from about 25 nm to about 50 nm; and by an average length of from about 2 microns to about 50 microns. In such embodiment, the Ag—La—Ce catalyst composition can further comprise $La(OH)_3$.

In an embodiment, a method of making an OCM catalyst composition (e.g., Ag—La—Ce catalyst composition) can comprise the steps of (a) contacting a La(III) aqueous solution with a Ce(III) aqueous solution to yield a La(III) and Ce(III) aqueous solution; (b) heating under stirring at least a portion of the La(III) and Ce(III) aqueous solution to a temperature of from about 80° C. to about 90° C., and for a time period of from about 1.5 hours to about 2.5 hours, to yield a heated La(III) and Ce(III) aqueous solution; (c) drying at least a portion of the heated La(III) and Ce(III) aqueous solution a temperature of from about 120° C. to about 130° C., and for a time period of from about 10 hours to about 14 hours, to yield a La(III) and Ce(III) mixture, wherein the La(III) and Ce(III) mixture can comprise $La(NO_3)_3$ and $Ce(NO_3)_3$; (d) calcining at least a portion of the La(III) and Ce(III) mixture at a temperature of from about 600° C. to about 650° C., and for a time period of from about 4 hours to about 6 hours, to yield a La(III) and Ce(IV) mixture, wherein the La(III) and Ce(IV) mixture can comprise a $La_2O_3$, $La(OH)_3$ and $CeO_2$ powder; (e) contacting at least a portion of the La(III) and Ce(IV) mixture with a Ag aqueous dispersion to form a Ag, La(III) and Ce(IV) aqueous dispersion; (f) optionally stirring at least a portion of the La(III) and Ce(IV) aqueous dispersion; (g) drying at least a portion of the Ag, La(III) and Ce(IV) aqueous dispersion at a temperature of from about 120° C. to about 130° C., and for a time period of from about 10 hours to about 14 hours, to yield a La(III) and Ce(IV) mixture (e.g., powder) doped with Ag (e.g., OCM catalyst composition); and (h) optionally thermally treating the La(III) and Ce(IV) mixture doped with Ag at a temperature of from about 250° C. to about 500° C., and for a time period of from about 10 hours to about 14 hours, yield a thermally treated OCM catalyst composition. In such embodiment, at least a portion of the La(III) and Ce(IV) mixture doped with Ag can be further formed into pellets and/or tablets.

In an embodiment, a method for producing ethylene can comprise the steps of (a) introducing a reactant mixture to a reactor comprising a Ag—La—Ce catalyst composition, wherein the reactant mixture comprises methane ($CH_4$) and oxygen ($O_2$), wherein the Ag—La—Ce catalyst composition comprises a $La_2O_3$, $La(OH)_3$ and $CeO_2$ mixture doped with Ag nanoparticles; (b) allowing at least a portion of the reactant mixture to contact at least a portion of the Ag—La—Ce catalyst composition and react via an OCM reaction to form a product mixture comprising olefins, wherein the OCM reaction can be characterized by an ignition temperature of from about 200° C. to about 500° C.; (c) recovering at least a portion of the product mixture from the reactor; and (d) recovering at least a portion of ethylene from the product mixture. In such embodiment, the method for producing ethylene can further comprise minimizing deep oxidation of methane to $CO_2$, wherein the product mixture can comprise less than about 15 mol % $CO_2$.

In an embodiment, the Ag—La—Ce catalyst compositions comprising a La(III) and Ce(IV) mixture doped with Ag, and methods of making and using same, as disclosed herein can advantageously display improvements in one or more composition characteristics when compared to an otherwise similar composition without Ag. In an embodiment, the Ag—La—Ce catalyst compositions comprising a La(III) and Ce(IV) mixture doped with Ag as disclosed herein can advantageously allow for using a reduced ignition temperature for an OCM reaction, when compared to an otherwise similar OCM reaction conducted in the presence of an OCM catalyst composition comprising a La(III) and Ce(IV) mixture without the Ag. Without wishing to be limited by theory, nano-size and/or micro-size dispersion of Ag within the Ag—La—Ce catalyst compositions can lower a reaction temperature for OCM when compared to conventional catalysts without nano-size and/or micro-size dispersion of Ag.

In an embodiment, the Ag—La—Ce catalyst compositions comprising a La(III) and Ce(IV) mixture doped with Ag can advantageously be prepared easier than nanofiber catalysts made by electro-spinning methods. Additional advantages of the Ag—La—Ce catalyst compositions comprising a La(III) and Ce(IV) mixture doped with Ag, and methods of making and using same, as disclosed herein can be apparent to one of skill in the art viewing this disclosure.

In an embodiment, an OCM catalyst composition (for example, a base or "parent" OCM catalyst such as a lanthanum-cerium OCM catalyst composition, a $Mn/Na_2WO_4$ metal oxide supported OCM catalyst, or other type of OCM catalyst composition) may be modified by the addition of silver as described herein. In an embodiment, an oxidative coupling of methane (OCM) catalyst composition may comprise silver (Ag), and the Ag and added via any suitable technique such as admixing, bulk mixing, granulation, deposition, sputtering, compounding, extruding, and the like. In an embodiment, an oxidative coupling of methane (OCM) catalyst composition may be doped with silver (Ag). In some embodiments, the added Ag has a predefined particle shape and size that survives incorporation into the OCM catalyst composition. In an embodiment, an oxidative coupling of methane (OCM) catalyst composition may comprise silver (Ag) nanoparticles, Ag microparticles, Ag nanowires, or combinations thereof. The Ag nanoparticles may be characterized by an average size of from about 1 nm to about 500 nm. The Ag microparticles may be characterized by an average size of from about 0.5 microns to about 50 microns. The Ag nanowires are characterized by an average diameter of from about 1 nm to about 500 nm, and by an average length of from about 0.5 microns to about 50 microns. The OCM catalyst composition may comprise from about 0.1 wt. % to about 20 wt. % Ag. The OCM catalyst composition of claim 1 further comprising a support, wherein at least a portion of the OCM catalyst composition contacts, coats, is embedded in, is supported by, and/or is distributed throughout at least a portion of the support. The support may comprise $MgO$, $Al_2O_3$, $SiO_2$, $ZrO_2$, or combinations thereof. The support may be in the form of particles, pellets, monoliths, foams, honeycombs, or combinations thereof, for example pellets comprising a binder or tablets excluding a binder.

In an embodiment, a method of making an oxidative coupling of methane (OCM) catalyst composition comprises contacting the OCM catalyst composition with silver (Ag), doping the OCM catalyst with Ag, or otherwise adding Ag to the OCM catalyst; and optionally thermally treating the OCM catalyst composition. The Ag may comprise Ag nanoparticles, Ag microparticles, Ag nanowires, or combinations thereof. The method may further comprise forming the OCM catalyst composition into pellets by extrusion. The method may further comprise forming the OCM catalyst composition into tablets under pressure. The method may further comprise contacting the OCM catalyst composition with a support. A modified OCM catalyst comprising Ag may be obtained by such methods.

In an embodiment, a method for producing olefins comprises (a) introducing a reactant mixture to a reactor comprising an oxidative coupling of methane (OCM) catalyst composition, wherein the reactant mixture comprises methane ($CH_4$) and oxygen ($O_2$), wherein the OCM catalyst composition is doped with silver (Ag); (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture. The Ag may comprise Ag nanoparticles, Ag microparticles, Ag nanowires, or combinations thereof. The OCM reaction may be characterized by an ignition temperature of from about 200° C. to about 500° C. The OCM reaction may be characterized by an ignition temperature that is decreased by from about 50° C. to about 300° C., when compared to an ignition temperature of an otherwise similar OCM reaction conducted in the presence of an OCM catalyst composition without the Ag. The reactor may comprise a catalyst bed comprising the OCM catalyst composition, wherein the catalyst bed is characterized by a catalyst bed temperature of from about 200° C. to about 1,100° C. The reactor may comprise a catalyst bed comprising the OCM catalyst composition, wherein the catalyst bed is characterized by a catalyst bed temperature that is decreased by from about 50° C. to about 300° C., when compared to a catalyst bed temperature of an otherwise similar catalyst bed comprising an OCM catalyst composition without the Ag. The reactor may comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, or combinations thereof. The reactant mixture may further comprise a diluent. The diluent may comprise water, nitrogen, inert gases, or combinations thereof. Equal to or greater than about 10 mol % of the methane in the reactant mixture may be converted to $C_{2+}$ hydrocarbons. Equal to or greater than about 20 mol % of selectivity to olefins may be obtained. Equal to or greater than about 40 mol % of selectivity to $C_2$ hydrocarbons may be obtained. Equal to or greater than about 20 mol % of selectivity to ethylene may be obtained. The product mixture may comprise less than about 15 mol % carbon dioxide ($CO_2$). The method may further comprise minimizing deep oxidation of methane to carbon dioxide ($CO_2$).

Ag Promoted $Mn$—$Na_2WO_4/SiO_2$ Catalyst

In some aspects, the OCM catalyst composition can be produced by doping $Mn/Na_2WO_4$ metal oxide supported catalyst compositions with silver to produce silver doped $Mn/Na_2WO_4$ metal oxide supported catalyst compositions. As shown in nonlimiting embodiments in the Examples, such silver doped catalysts have higher methane conversion and light olefin ($C_2$-$C_4$) selectivity when compared with otherwise similar $Mn/Na_2WO_4$ catalysts that have not been doped with silver. Further, in some aspects, silver can be present in the silver doped $Mn/Na_2WO_4$ metal oxide supported catalyst compositions in an amount effective to maximize the conversion and selectivity parameters of the catalysts doped with silver of the current disclosure. For example, silver doped $Mn/Na_2WO_4$ metal oxide supported catalyst compositions can comprise Ag in amounts ranging from 0.1 wt. % to 10 wt. % silver (based on the total weight of the silver doped $Mn/Na_2WO_4$ metal oxide supported catalyst compositions), alternatively 0.1 wt. % to 5 wt. % silver, or alternatively from 0.2 wt. % to 3.0 wt. % silver, thereby allowing for OCM reaction temperatures to be reduced to 600° C. to 775° C., alternatively 650° C. to 775° C., or alternatively 675° C. to 750° C. As will be appreciated by one of skill in the art, and with the help of this disclosure, a reduced OCM reaction temperature can in turn allow for improved catalyst stability and selectivity, while lowering the production of undesired oxidation products. Still further, in some aspects of the current disclosure, the silver doped $Mn/Na_2WO_4$ metal oxide supported catalyst compositions of the present disclosure can have a $C_{2+}$ hydrocarbons selectivity that is greater than a theoretical selectivity limit for $C_{2+}$ hydrocarbons for the OCM reaction at a given set of reaction conditions (e.g., under a $CH_4$ to $O_2$ ratio of 7.4, a reaction temperature of 725° C., and 18% $CH_4$ conversion). The silver doped $Mn/Na_2WO_4$ metal oxide supported catalyst compositions of the present disclosure have increased stability, longer life spans, and increased efficiency in producing light olefins from methane during an OCM reaction, when compared with otherwise similar $Mn/Na_2WO_4$ metal oxide supported catalyst compositions that have not been doped with silver.

In a particular aspect of the current disclosure, there is disclosed a supported catalyst (e.g., supported catalyst composition) capable of catalyzing an OCM reaction (e.g., a supported OCM catalyst, a supported OCM catalyst composition), wherein the supported catalyst includes a silver (Ag) doped $Mn/Na_2WO_4$ and a metal oxide support. In such aspect, the supported OCM catalyst composition can surprisingly display a greater methane conversion and $C_{2+}$ hydrocarbon selectivity as compared to an otherwise similar $Mn/Na_2WO_4$ metal oxide supported catalyst composition (e.g., the same $Mn/Na_2WO_4$ metal oxide supported catalyst composition) that has not been doped with silver. The silver doped $Mn/Na_2WO_4$ metal oxide supported catalyst composition can have a selectivity for $C_{2+}$ hydrocarbons that is greater than the theoretical selectivity limit for $C_{2+}$ hydrocarbons selectivity for the oxidative coupling of methane reaction at a lowered or reduced reaction temperature, such as an OCM reaction temperature of (e.g., lowered to) from about 600° C. to about 775° C., alternatively from about 650° C. to about 775° C., or alternatively from about 675° C. to about 750° C. Such lowered OCM reaction temperature can be at least 25° C. lower than the reaction temperature needed for an otherwise similar $Mn/Na_2WO_4$ metal oxide supported catalyst composition that has not been doped with silver (e.g., undoped $Mn/Na_2WO_4$ metal oxide supported catalyst composition). Further, such a lowered temperature can prolong a catalyst's life (e.g., a commercial catalyst's life), (for example, about two months or longer), which can result in economic savings for a commercial operation as the equipment can require less maintenance and less reaction down-time may be experienced (e.g., the reaction would not need to be stopped to change the catalyst). In some aspects, the silver doped $Mn/Na_2WO_4$ metal oxide supported catalyst's life can be greater than the life of an otherwise similar $Mn/Na_2WO_4$ metal oxide supported catalyst that has not been doped with silver. The silver doped $Mn/Na_2WO_4$ metal oxide supported catalyst composition of the current disclosure can be supported on a metal oxide support that can comprise silicon dioxide, lanthanum oxide, aluminum oxide, or combinations thereof. In a preferred aspect, the metal oxide support can be silicon dioxide.

In an aspect, the OCM catalyst composition can comprise a metal oxide supported catalyst composition including or including essentially silver, manganese, sodium, tungsten, oxygen, and silicon, wherein silver can be present in the metal oxide supported catalyst composition in an amount of from about 0.1 wt. % to about 10 wt. % silver, alternatively from about 0.1 wt. % to about 5 wt. % silver, or alternatively from about 0.2 wt. % to about 3 wt. % of silver, based on the total weight of the metal oxide supported catalyst composition. The amount of manganese in the metal oxide supported catalyst composition can be from about 0.1 wt. % to about 10 wt. % manganese, based on the total weight of the metal oxide supported catalyst composition; and the amount of $Na_2WO_4$ in the metal oxide supported catalyst composition can be from about 0.1 wt. % to about 15 wt. % $Na_2WO_4$, based on the total weight of the metal oxide supported catalyst composition. In one instance, the silver doped $Mn/Na_2WO_4$ metal oxide supported catalyst is not a nanowire or a nanoparticle. The $Mn/Na_2WO_4$ metal oxide supported catalyst, in one aspect, is not present in a nanowire substrate or a nanoparticle substrate. The silver doped $Mn/Na_2WO_4$ metal oxide supported catalyst composition of the current disclosure can be in powdered or particulate form. As will be appreciated by one of skill in the art, and with the help of this disclosure, while in some aspects the $Mn/Na_2WO_4$ metal oxide supported catalyst composition can exclude a nanowire substrate or a nanoparticle substrate, the silver used for doping can be present in the silver doped $Mn/Na_2WO_4$ metal oxide supported catalyst composition as a Ag nanowire, Ag nanoparticle, Ag microparticle, or combinations thereof.

In an aspect, a silver doped $Mn—Na_2WO_4/SiO_2$ supported composition can lower the operating temperature of the OCM reaction, thereby permitting improved catalyst stability and selectivity and lowering the production of undesired oxidation products.

In an aspect, a method of producing $C_{2+}$ hydrocarbons from an OCM reaction can comprise contacting a reactant feed of a methane containing gas and an oxygen containing gas with the silver doped $Mn/Na_2WO_4$ metal oxide supported catalyst composition to produce a product stream comprising $C_{2+}$ hydrocarbons. In such aspect, the method can provide for a selectivity of $C_{2+}$ hydrocarbons that is at least 60% to 90% at a reaction temperature of from about 650° C. to about 750° C. The method thereby allows the OCM reaction to be performed at a temperature of from about 600° C. to about 775° C., alternatively from about 650° C. to about 775° C., or alternatively from about 675° C. to about 750° C. In some aspects, the methane containing gas can be natural gas.

In an aspect of the current disclosure, a system for producing $C_{2+}$ hydrocarbons can comprise an inlet for a reactant feed containing methane and oxygen; a reaction zone that can be configured to be in fluid communication with the inlet, wherein the reaction zone contains the silver doped $Mn/Na_2WO_4$ metal oxide supported catalyst composition; and an outlet configured to be in fluid communication with the reaction zone and configured to remove a first product stream including $C_{2+}$ hydrocarbons from the reaction zone. In some aspects, the reaction zone of the disclosed system can further include the reactant feed and the first product stream. The temperature of the reactant feed at the inlet or just prior to or during contact with the silver doped $Mn/Na_2WO_4$ metal oxide supported catalyst composition can be from about 600° C. to about 775° C., alternatively from about 650° C. to about 775° C., or alternatively from about 675° C. to about 750° C. The reaction zone of the system disclosed herein can be a continuous flow reactor selected from the group consisting of a fixed-bed reactor, a fluidized reactor, and a moving bed reactor.

In some aspects, the supported OCM catalysts disclosed herein can comprise a catalytic material and a support (e.g., an underlying support); wherein the catalytic material can include manganese, sodium, tungsten, and oxygen. Nonlimiting examples of catalytic materials suitable for use in the present disclosure in the supported OCM catalysts include $Mn/Na_2WO_4$, $Na/Mn/O$, $Na_2WO_4$, $Mn_2O_3/Na_2WO_4$, $Mn_3O_4/Na_2WO_4$, $MnWO_4/Na_2WO_4$, $MnWO_4/Na_2WO_4$, $Mn/WO_4$, $Na_2WO_4/Mn$, and the like, or combinations thereof. In a preferred aspect, the catalytic material can be $Mn/Na_2WO_4$, for example in silver doped $Mn/Na_2WO_4$ metal oxide supported catalyst compositions.

The support material or a carrier for metal oxide supported catalyst compositions can be porous and have a high surface area. In some embodiments, the support for metal oxide supported catalyst compositions is active (i.e., has catalytic activity). In other aspects, the support for metal oxide supported catalyst compositions is inactive (i.e., non-catalytic, does not have catalytic activity). The support for metal oxide supported catalyst compositions can be an inorganic oxide. In some embodiments, the support for metal oxide supported catalyst compositions comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), calcium oxide (CaO), strontium oxide (SrO), zirconium oxide ($ZrO_2$), zinc oxide (ZnO), lithium aluminum oxide ($LiAlO_2$), magnesium aluminum oxide ($MgAlO_4$), manganese oxides (MnO, $MnO_2$, $Mn_3O_4$), lanthanum oxide ($La_2O_3$), activated carbon, silica gel, zeolites, activated clays, silicon carbide (SiC), diatomaceous earth, magnesia, aluminosilicates, calcium aluminate, and the like, or combinations thereof. In some aspects, the support for metal oxide supported catalyst compositions is MgO, $Al_2O_3$, $La_2O_3$, $SiO_2$, and the like, or combinations thereof. In some embodiments, the support for metal oxide supported catalyst compositions comprises $SiO_2$. In still other embodiments, the support material for metal oxide supported catalyst compositions can include a carbonate (e.g., $MgCO_3$, $CaCO_3$, $SrCO_3$, $BaCO_3$, $Y_2(CO_3)_3$, $La_2(CO_3)_3$, or combination thereof).

All of the materials used to make the supported OCM catalysts disclosed herein (e.g., silver doped metal oxide supported catalyst compositions) can be purchased or made by processes known to those of ordinary skill in the art (e.g., precipitation/co-precipitation, sol-gel, templates/surface derivatized metal oxides synthesis, solid-state synthesis of mixed metal oxides, microemulsion techniques, solvothermal techniques, sonochemical techniques, combustion synthesis, etc.).

The amount of catalytic material on the support material in the metal oxide supported catalyst compositions depends, inter alia, on the catalytic activity of the catalyst. In some embodiments, the amount of catalyst (e.g., catalytic material) present on the support in the metal oxide supported catalyst compositions ranges from 1 to 100 parts by weight of catalyst per 100 parts by weight of support, or alternatively from 10 to 50 parts by weight of catalyst per 100 parts by weight of support. In other embodiments, the amount of catalyst present on the support in the metal oxide supported catalyst compositions ranges from 100 to 200 parts of catalyst per 100 parts by weight of support, alternatively from 200 to 500 parts of catalyst per 100 parts by weight of support, or alternatively from 500 to 1,000 parts of catalyst per 100 parts by weight of support material.

The supported OCM catalysts disclosed herein (e.g., silver doped metal oxide supported catalyst compositions) can comprise a dopant or a doping agent or be referred to as being "doped" with metal elements, semi-metal elements, non-metal elements, or combinations thereof. In a particular aspect of the current disclosure, the dopant can be or include metallic silver or silver in the form of a salt (e.g., silver salt), for example silver acetate, silver acetylide, silver arsenate, silver azide, silver behenate, silver bromate, silver bromide, silver carbonate, silver chlorate, silver chloride, silver chromate, silver cyanate, silver cyanide, silver dichromate, silver fulminate, silver hexafluorophosphate, silver iodate, silver iodide, silver molybdate, silver nitrate, silver nitride, silver nitrite, silver oxalate, silver oxide, silver perchlorate, silver permanganate, silver perrhenate, silver phosphate, silver proteinate, silver selenite, silver subfluoride, silver sulfadiazine, silver sulfate, silver sulfide, silver sulfite, silver telluride, silver tetrafluoroborate, silver thiocyanate, silver trifluoromethanesulfonate, silver fluoride, silver selenide, silver oxide, or combinations thereof. In some aspects, silver nitrate ($AgNO_3$) is used as the dopant in the silver doped metal oxide supported catalyst compositions.

The dopant comprising metallic silver and/or a silver salt can be included in any OCM catalyst composition disclosed herein, whether the OCM catalyst composition is a supported OCM catalyst composition or an unsupported OCM catalyst composition.

In an aspect, the supported OCM catalyst composition (e.g., silver doped metal oxide supported catalyst composition) includes essentially silver, manganese, sodium, tungsten, oxygen, and silicon. In an aspect, the supported OCM catalyst composition comprises Ag—Mn—$Na_2WO_4$ supported on silica (Ag—Mn—$Na_2WO_4/SiO_2$).

The dopant can be combined with the catalyst (e.g., catalytic material, supported catalytic material, etc.) by processes known to those of skill in the art (e.g., precipitation/co-precipitation, impregnation, sol-gel, templates/surface derivatized metal oxides synthesis, solid-state synthesis of mixed metal oxides, microemulsion techniques, solvothermal, sonochemical, combustion synthesis, etc.). The amount of dopant added to the catalyst (e.g., catalytic material, supported catalytic material, etc.) can range from about 0.01 wt./wt. % to about 50 wt./wt. %, with all ranges in between, for example from about 0.1 wt./wt. % to about 20 wt./wt. %, or alternatively from about 1 wt./wt. % to about 10 wt./wt. %, based on the total weight of the catalyst. In a preferred aspect, the amount of dopant added to the catalyst ranges from about 1 wt./wt. % to about 5 wt./wt. %, alternatively about 1 wt./wt. %, alternatively about 2 wt./wt. %, alternatively about 3 wt./wt. %, alternatively about 4 wt./wt. %, or alternatively about 5 wt./wt. %, based on the total weight of the catalyst.

The support material can be blended with the catalytic material and dopant to make a catalytic precursor material. Supported OCM catalysts may be prepared using generally known catalyst preparation techniques. In some embodiments, impregnation aids may be used during preparation of the supported OCM catalyst. Examples of impregnation aids include a citric acid component, ethylenediaminetetraacetic acid (EDTA), ammonia, or mixtures thereof. In some aspects, the catalytic material, dopant and support may be mixed with any suitable mixing equipment to form a doped catalytic material/support mixture. In an embodiment, the catalyst is made by step wise addition of metal precursors to a support. By way of example, an aqueous solution of $Mn(NO_3)_2$ can be added in a controlled manner (e.g., dropwise) onto a silicon dioxide $SiO_2$ material (e.g., silica gel) to form a $Mn(NO_3)_2/SiO_2$ mixture. To the $Mn(NO_3)_2/SiO_2$ mixture, an aqueous solution of $AgNO_3$ can be added in a dropwise manner to obtain a $Mn(NO_3)_2/AgNO_3/SiO_2$ mixture; and then, an aqueous $Na_2WO_4$ solution can be added in a controlled manner or rate (e.g., dropwise) to the $Mn(NO_3)_2/AgNO_3/SiO_2$ mixture (e.g., doped catalytic material/ support mixture). The doped catalytic material/support mixture may be mixed during the additions of reagents using any suitable mixing equipment. Examples of suitable mixing equipment include tumblers, stationary shells or troughs, Muller mixers (for example, batch type or continuous type), impact mixers, and any other generally known mixer, or generally known device, that will suitably provide the doped catalytic material/support mixture. In some embodiments, the materials used for preparing the supported OCM catalyst can be mixed until the doped catalytic material is substantially homogeneously dispersed in the support, e.g., for an amount of time effective to substantially homogeneously disperse the doped catalytic material in the support. In some embodiments, the doped catalytic material/support mixture is heat treated at temperatures from about 150° C. to about 800° C., alternatively from about 200° C. to about 740° C., or alternatively from about 300° C. to about 730° C. to remove volatile materials. In some embodiments, the doped catalytic material/support mixture may be heat treated in the presence of hot air and/or oxygen rich air at a temperature in a range between about 200° C. and about 1,000° C., or alternatively between about 300° C. and about 800° C., for about 4 to about 10 hours, or alternatively for about 7 hours, to calcine the catalyst (e.g., remove volatile matter such that at least a portion of the catalytic material is converted to a corresponding metal oxide) to produce a calcined catalyst (e.g., calcined supported catalyst, calcined supported OCM catalyst, etc.). In another embodiment, an aqueous $AgNO_3$ solution can be added in a controlled manner to a $Mn$—$Na_2WO_4/SiO_2$ calcined catalyst with agitation, and the resulting mixture can be stirred until the silver reagent is thoroughly mixed with the $Mn$—$Na_2WO_4/SiO_2$ calcined catalyst, to produce the silver doped $Mn$—$Na_2WO_4/SiO_2$ catalyst. The silver doped $Mn$—$Na_2WO_4/SiO_2$ catalyst can be dried at 120° C. to 150° C. for a desired amount of time (e.g., 1, 2, 3, 4, 5, 6, or more hours).

Additional catalysts can be used in combination with the OCM catalyst of the current disclosure (e.g., a first catalyst). The additional catalysts (e.g., a second catalyst, third catalyst, fourth catalyst, etc.) can be positioned up stream or downstream or mixed with the OCM catalyst of the current disclosure (e.g., a first catalyst). The additional catalysts can be supported, bulk metal catalysts, unsupported catalysts, or combinations thereof. The support of the additional catalysts (e.g., additional catalyst support) can be catalytically active, catalytically inactive, or combinations thereof. The additional catalyst support can include MgO, $Al_2O_3$, $SiO_2$, and the like, or combinations thereof. One or more of the additional catalysts can include one or more metals (e.g., catalytic metals) or metal compounds thereof. Nonlimiting examples of catalytic metals suitable for use in the present disclosure include Li, Na, Ca, Cs, Mg, La, Ce, W, Mn, Ru, Rh, Ni, Pt, and the like, or combinations thereof.

Nonlimiting examples of additional catalysts suitable for use in the present disclosure include La on a MgO support; Na, Mn, and $La_2O_3$ on an aluminum support; Na and Mn oxides on a silicon dioxide support; $Na_2WO_4$ and Mn on a silicon dioxide support; and the like; or combinations thereof. Nonlimiting examples of additional catalysts that promote OCM to produce ethylene include $Li_2O$, $Na_2O$, $Cs_2O$, MgO, $WO_3$, $Mn_3O_4$, and the like, or combinations thereof. In some aspects, the second catalyst (e.g., additional catalyst) has a $C_{2+}$ selectivity that is greater than a $C_{2+}$ selectivity of the OCM catalyst as disclosed herein (e.g., a first catalyst, OCM supported catalyst, OCM unsupported catalyst, etc.). In other aspects, the second catalyst (e.g., additional catalyst) has a $C_{2+}$ selectivity that is lower than a $C_{2+}$ selectivity of the OCM catalyst as disclosed herein (e.g., a first catalyst, OCM supported catalyst, OCM unsupported catalyst, etc.).

The reactant mixture that can be used for conducting an OCM reaction as disclosed herein in the presence of a silver doped metal oxide supported catalyst composition can be a gaseous mixture that includes, but is not limited to, a hydrocarbon or mixtures of hydrocarbons and oxygen (e.g., oxygen containing gas); wherein the hydrocarbon or mixtures of hydrocarbons can include natural gas, liquefied petroleum gas containing $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), oxygenated hydrocarbons, biodiesel, alcohols, dimethyl ether, and the like, or combinations thereof. In a preferred aspect, the hydrocarbon is a mixture of hydrocarbons that is predominately methane (e.g., natural gas). The oxygen containing gas (e.g., oxidant) used or conducting an OCM reaction as disclosed herein in the presence of a silver doped metal oxide supported catalyst composition can be air, oxygen enriched air, oxygen gas, and the like, or combinations thereof, and can be obtained from various sources. The reactant mixture that is contacted with the silver doped metal oxide supported catalyst composition may further contain other gases, provided that these do not negatively affect the reaction. Nonlimiting examples of such other gases that can be present in the reactant mixture include carbon dioxide, nitrogen, hydrogen, and the like, or combinations thereof. The hydrogen may be from various sources, including streams coming from other chemical processes, such as ethane cracking, methanol synthesis, conversion of methane to aromatics, and the like, or combinations thereof. Carbon dioxide may be from natural gas, from a waste stream, from a recycle gas stream (e.g., a recycle stream from a plant on the same site, such as for example from an ammonia synthesis plant), recovered carbon dioxide (e.g., carbon dioxide recovered from a gas stream), and the like, or combinations thereof.

The OCM reaction can be conducted in the presence of a silver doped metal oxide supported catalyst composition in a continuous flow reactor. Reaction processing conditions in the continuous flow reactor comprising an OCM catalyst as disclosed herein can be varied to achieve a desired result (e.g., a $C_{2+}$ hydrocarbons product).

In an embodiment, the reactant mixture that is contacted with the silver doped metal oxide supported catalyst composition can be characterized by a methane to oxygen molar ratio of from about 1:1 to about 20:1, alternatively from about 1:1 to about 16:1, alternatively from about 2:1 to about 15:1, alternatively from about 2.5:1 to about 10:1, or alternatively from about 3:1 to about 9:1.

In an aspect, a process for producing $C_{2+}$ hydrocarbons in the presence of a silver doped metal oxide supported catalyst composition can include contacting a feed stream of hydrocarbon and oxidant with the silver doped metal oxide supported catalyst composition as disclosed herein under established desired or optimum OCM conditions (e.g., a methane to oxygen ratio of 7.4, and a reaction temperature of 725° C.) to afford a methane conversion of greater than 13.4% and a $C_{2+}$ selectivity greater than 75.5%.

In an aspect, the methane conversion in the presence of a silver doped metal oxide supported catalyst composition is greater than about 14%, alternatively greater than about 15%, alternatively greater than about 16%, or alternatively greater than about 17%. In an aspect, the $C_{2+}$ selectivity is greater than about 76%, or alternatively greater than about 77%. Methane conversion and $C_{2+}$ selectivity can be calculated as disclosed in more detail in the Examples section, for example such as described in equations (1)-(3).

In some aspects, the methane conversion in the presence of a silver doped metal oxide supported catalyst composition can be from about 10% to about 60%, alternatively from about 12.5% to about 50%, or alternatively from about 15% to about 45%.

In an aspect, the OCM catalyst comprising a silver doped metal oxide supported catalyst composition can be used in continuous flow reactors to produce $C_{2+}$ hydrocarbons from methane (e.g., natural gas). Generally, the $C_{2+}$ hydrocarbons are obtained from the OCM reaction conducted in the presence of a silver doped metal oxide supported catalyst composition. Nonlimiting examples of configurations of catalytic material (e.g., OCM catalyst, OCM catalyst composition, etc.) in a continuous flow reactor are provided herein. The continuous flow reactor can be a fixed bed reactor, a stacked bed reactor, a fluidized bed reactor, an ebullating bed reactor, or combinations thereof. In an aspect, the continuous flow reactor is a fixed bed reactor. The catalytic material can be arranged in the continuous flow reactor in layers (e.g., catalytic beds) or mixed with the reactant stream (e.g., ebullating bed).

In some embodiments, a volume of catalyst in a contacting zone of the continuous flow reactor (e.g., a zone, volume or space inside the reactor where the reactant mixture contacts the OCM catalyst) can be in a range from about 10 vol. % to about 60 vol. %, alternatively from about 20 vol. % to about 50 vol. %, or alternatively from about 30 vol. % to about 40 vol. %, based on the total volume of reactant mixture in the contacting zone. Processing conditions in the continuous flow reactor may include, but are not limited to, temperature, pressure, oxidant source flow (e.g., air or oxygen), hydrocarbon gas flow (e.g., methane or natural gas), ratio of reactants, or combinations thereof. Process conditions can be controlled to produce $C_{2+}$ hydrocarbons with specific properties (e.g., percent ethylene, percent butene, percent butane, etc.). The average temperature in the continuous flow reactor can range from 600° C., 625° C., 650° C., 655° C., 660° C., 665° C., 670° C., 675° C., 680° C., 685° C., 690° C., 695° C., 700° C., 705° C., 710° C., 715° C., 720° C., 725° C., 730° C., 735° C., 740° C., 745° C., 750° C., 755° C., 760° C., 765° C., 770° C., to 775° C., or any value or range there between. In some aspects, a pressure in the continuous flow reactor can be about 0.1 MPa. The GHSV of the reactant feed ranges from about 500 $h^{-1}$ to about 50,000 $h^{-1}$ or more. In some embodiments, the GHSV is as high as can be obtained under the reaction conditions. In some aspects, the reactant mixture can have a molar ratio of methane to oxygen from about 0.3 to about 20, alternatively from about 0.5 to about 15, alternatively from about 1 to about 10, or alternatively from about 5 to about 7.5, or any range there between. The molar ratio of methane to oxygen can be 0.3, 0.5, 1, 1.5, 2, 2.5, 3, 3.5, 4, 4.5, 5, 5.5, 6, 6.5, 7, 7.5, 8, 8.5, 9, 9.5, 10, 15, or 20, or any value there between. Severity of the process conditions may be manipulated by changing the hydrocarbon source, oxygen source, pressure, flow rates, the temperature of the process, the catalyst type, catalyst to feed ratio, and the like, or combinations thereof. In a preferred embodiment, the average temperature ranges from about 650° C. to about 775° C., or alternatively from about 675° C. to about 750° C. or any range there between at about 1 bara, and/or a GHSV from about 500 $h^{-1}$ to about 50,000 $h^{-1}$ or more.

In some aspects, the reactor comprising the silver doped metal oxide supported catalyst composition can be characterized by a GHSV of from about 500 $h^{-1}$ to about 100,000 $h^{-1}$, alternatively from about 500 $h^{-1}$ to about 50,000 $h^{-1}$, alternatively from about 1,000 $h^{-1}$ to about 40,000 $h^{-1}$, or alternatively from about 1,500 $h^{-1}$ to about 25,000 $h^{-1}$.

Referring to FIG. 1, a schematic of system 100 for the production of $C_{2+}$ hydrocarbons is depicted. System 100 may include a continuous flow reactor 102 and a catalytic material (e.g., OCM catalyst, OCM catalyst composition, etc.) 104. In a preferred embodiment, catalytic material 104 can be an OCM catalyst composition as disclosed herein, such as the Ag doped Mn—$Na_2WO_4/SiO_2$ catalyst and/or the Ag—La—Ce catalyst. A reactant stream that includes methane can enter the continuous flow reactor 102 via the feed inlet 106. An oxygen containing gas (oxidant) is provided in via oxidant source inlet 108. In some aspects, the methane and the oxygen containing gas are fed to the reactor via one inlet. In other aspects, the methane and the oxygen containing gas are fed to the reactor via separate or different inlets (e.g., 106, 108). Reactants can be provided to the continuous flow reactor 102 such that the reactants mix in the reactor to form a reactant mixture prior to contacting the catalytic material 104. In some embodiments, the catalytic material and the reactant feed can be heated to approximately the same temperature. In some instances, the catalytic material 104 may be layered in the continuous flow reactor 102. Contact of the reactant mixture with the catalytic material 104 can produce a product stream, such as for example $C_{2+}$ hydrocarbons, and can generate heat (i.e., an exotherm or rise in temperature is observed). After contacting the OCM catalyst, the reaction conditions can be maintained downstream of the catalytic material at temperatures sufficient to promote continuation of the process (e.g., OCM reactions). The product stream can exit continuous flow reactor 102 via a product outlet 110.

The resulting $C_{2+}$ hydrocarbons produced from the processes and/or systems of the current disclosure are separated using gas/liquid separation techniques, for example, distillation, absorption, membrane technology to produce a gaseous stream that includes carbon monoxide, carbon dioxide, hydrogen, $C_{2+}$ hydrocarbons product, and a water stream. The $C_{2+}$ hydrocarbons are separated from the hydrogen and carbon monoxide and/or carbon dioxide, if present, using gas/gas separation techniques, for example a hydrogen selective membrane, a carbon monoxide selective membrane, cryogenic distillation, or combinations thereof to produce $C_{2+}$ hydrocarbons, carbon monoxide, carbon dioxide, hydrogen, or mixtures thereof. The separated products or mixture of products can be used in additional downstream reaction schemes to create additional products, or for energy production. Examples of other products can include chemical products such as methanol production products, olefin synthesis (e.g., via Fischer-Tropsch reaction) products, aromatics production products, carbonylation of methanol products, carbonylation of olefins products, products of reduction of iron oxide in steel production, etc. The method of producing $C_{2+}$ hydrocarbons from an OCM reaction can further include isolating and/or storing the produced gaseous mixture and/or the separated products.

In an embodiment, the OCM catalyst compositions comprising one or more oxides doped with Ag, and methods of making and using same, as disclosed herein can advantageously display improvements in one or more composition characteristics when compared to an otherwise similar composition without Ag. In an embodiment, the OCM catalyst compositions comprising one or more oxides doped with Ag as disclosed herein can advantageously allow for using a reduced ignition temperature for an OCM reaction, when compared to an otherwise similar OCM reaction conducted in the presence of an OCM catalyst composition comprising one or more oxides without the Ag. In an embodiment, the OCM catalyst compositions comprising one or more oxides doped with Ag as disclosed herein can advantageously allow for an overall reduced temperature of an OCM reaction (e.g., a temperature needed to achieve 100% oxygen conversion), when compared to a temperature of an otherwise similar OCM reaction conducted in the presence of an OCM catalyst composition comprising one or more oxides without the Ag. Without wishing to be limited by theory, nano-size and/or micro-size dispersion of Ag within the OCM catalyst compositions can lower a reaction temperature for OCM when compared to conventional catalysts without nano-size and/or micro-size dispersion of Ag.

In an embodiment, the OCM catalyst compositions comprising one or more oxides doped with Ag can advantageously allow for lowered reaction temperatures, wherein the catalyst OCM catalyst compositions comprising one or more oxides doped with Ag can advantageously yield better selectivity, and wherein the catalyst OCM catalyst compositions comprising one or more oxides doped with Ag can advantageously have better stability.

In an embodiment, the OCM catalyst compositions comprising one or more oxides doped with Ag can advantageously be prepared easier than nanofiber catalysts made by electro-spinning methods or other methods. Additional advantages of the OCM catalyst compositions comprising one or more oxides doped with Ag, and methods of making and using same, as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Ag—La—Ce Catalyst

Example 1

OCM catalyst compositions were prepared as follows. A La(III) and Ce(IV) mixture catalyst (catalyst #1) was prepared as follows. 12.03 grams of $La(NO_3)_3 \cdot 6H_2O$ was dissolved in 20 ml of water to yield a La(III) aqueous solution. 1.20 grams of $Ce(NO_3)_3 \cdot 6H_2O$ was dissolved in 5 ml of water to yield a Ce(III) aqueous solution. The two aqueous solutions were mixed and then heated at 85° C. for 2 hours under agitation/stirring. The obtained mixture was then dried overnight at 125° C. to yield a dried powder, which was then calcined at 625° C. for 5 hours to yield catalyst #1 in the form of a powder.

OCM catalyst compositions (e.g., La(III) and Ce(IV) mixture doped with Ag) were prepared from catalyst #1 as follows. Ag nanoparticles with an average size of 15 nm were dispersed in water at a concentration of 5.0% to yield a Ag aqueous dispersion. 2.7 grams of the Ag aqueous dispersion was then added to catalyst #1, to get a catalyst with a Ag content of 2.7 wt. %. The obtained mixture was then dried overnight at 125° C. to yield catalyst #2 comprising $La_2O_3$ and $CeO_2$ mixture doped with Ag nanoparticles in the form of a powder.

Another catalyst composition was prepared by doping a $SiO_2$ support with Ag to produce catalyst #3 ($Ag/SiO_2$). Silica gel (Davisil® Grade 646) was used after drying overnight. 5.0 g of the silica gel was used. Ag nanoparticles with an average size of 15 nm were dispersed in water at a concentration of 5.0% to yield a Ag aqueous dispersion. 3.0 g of the Ag particle solution was added onto the silica gel. The obtained mixture was then dried overnight at 125° C. to yield catalyst #3.

Catalyst #4 was prepared by thermally treating catalyst #2 at 250° C. for 6 hours. Catalyst #5 was prepared by thermally treating catalyst #2 at 500° C. for 6 hours.

Example 2

Oxidative coupling of methane (OCM) reactions were conducted by using catalysts prepared as described in Example 1 as follows. A mixture of methane and oxygen along with an internal standard, an inert gas (neon) were fed to a quartz reactor with an internal diameter (I.D.) of 4 mm heated by traditional clamshell furnace. A catalyst (e.g., catalyst bed) loading was 20 mg, and total flow rate of reactants was 160 cc/min. The reactor was first heated to a desired temperature under an inert gas flow and then a desired gas mixture was fed to the reactor. All OCM reactions were conducted at a methane to oxygen molar ratio of 4.

Methane conversion was calculated according to equation (1). Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. For example, the methane conversion can be calculated by using equation (1):

$$CH_4 \text{ conversion} = \frac{C_{CH_4}^{in} - C_{CH_4}^{out}}{C_{CH_4}^{in}} \times 100\% \quad (1)$$

wherein $C_{CH_4}^{in}$=number of moles of C from $CH_4$ that entered the reactor as part of the reactant mixture; and $C_{CH_4}^{out}$=number of moles of C from $CH_4$ that was recovered from the reactor as part of the product mixture. Methane conversion of novel catalyst compositions (e.g., catalysts #2) were compared with the methane conversion for the un-doped catalyst #1, and for the catalyst #3 comprising a support only doped with Ag, and the data is displayed in FIG. 2A. It can be seen that the ignition temperature of catalyst #2 was lowered to 300° C. from 480° C. for un-doped catalyst #1. Catalyst #3 showed no OCM catalytic activity. The results in FIG. 2A indicate that doping metal oxides with Ag increases catalyst activity significantly, and as a result the ignition temperature is lowered.

Figure 2A:
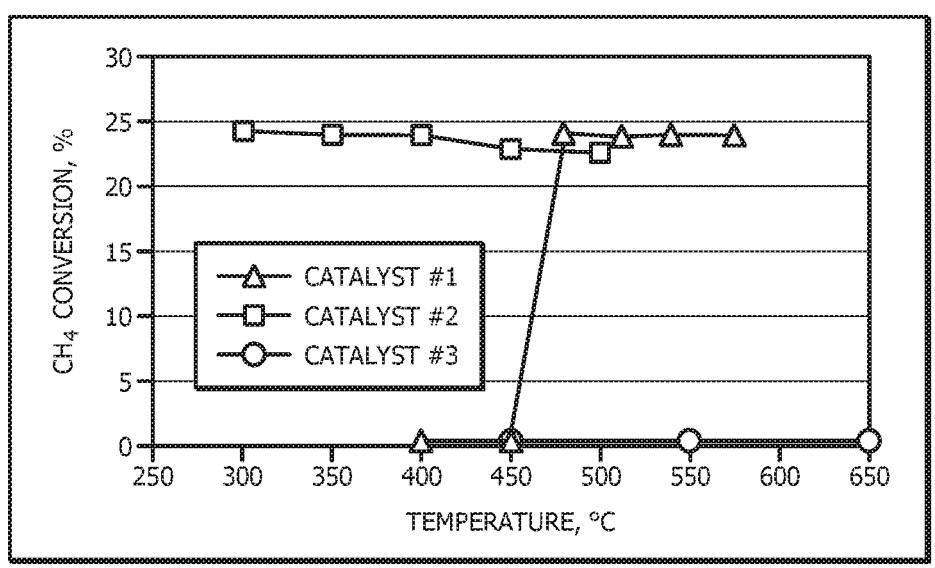
FIG. 2A displays a graph of methane conversion in an OCM reaction as a function of temperature for various catalysts.
Figure 2B:
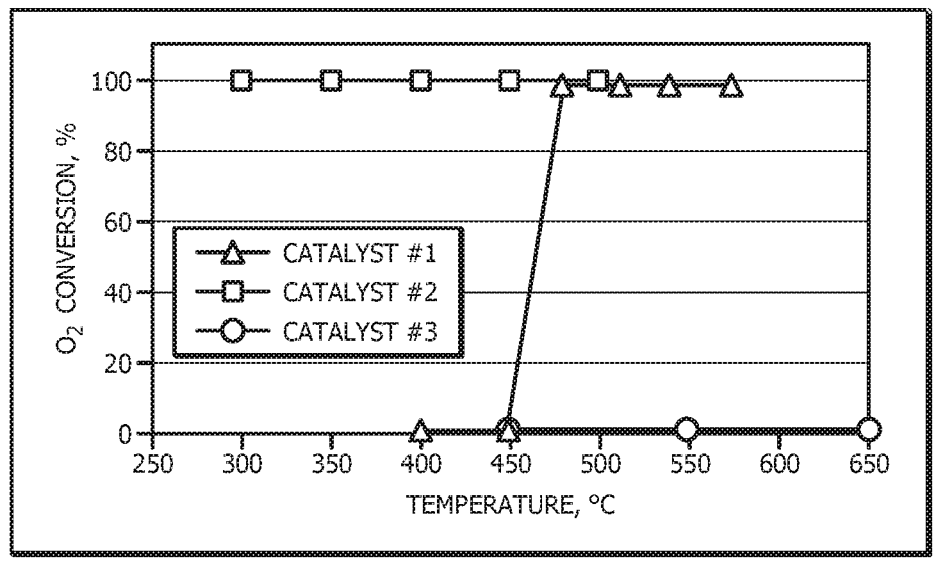
FIG. 2B displays a graph of oxygen conversion in an OCM reaction as a function of temperature for various catalysts.

FIG. 2B displays oxygen conversions for the novel catalyst compositions (e.g., catalyst #2) as compared with the un-doped catalyst #1, and the catalyst #3 comprising a support only doped with Ag. For example, the oxygen conversion can be calculated by using equation (2):

$$O_2 \text{ conversion} = \frac{O_2^{in} - O_2^{out}}{O_2^{in}} \times 100\% \quad (2)$$

wherein $O_2^{in}$=number of moles of $O_2$ that entered the reactor as part of the reactant mixture; and $O_2^{out}$=number of moles of $O_2$ that was recovered from the reactor as part of the product mixture. For catalyst #2, at 300° C. ignition temperature, 100% oxygen conversion was obtained. For catalyst #3, there was no OCM catalytic activity. When comparing un-doped catalyst #1 and Ag doped catalyst #2, it can be observed that catalyst #2 achieves 100% $O_2$ conversion at much lower temperatures than un-doped catalyst #1.

Figure 2C:
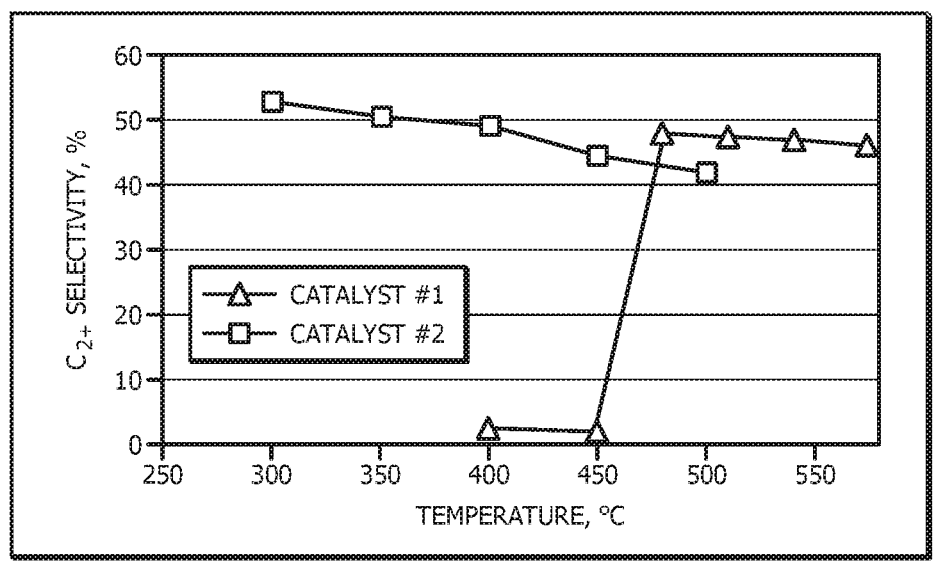
FIG. 2C displays a graph of $C_{2+}$ selectivity in an OCM reaction as a function of temperature for various catalysts.

FIG. 2C displays $C_{2+}$ selectivity values for the novel catalyst compositions (e.g., catalysts #2) as compared with the un-doped catalyst #1. Generally, a selectivity to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a $C_x$ selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4s}$, $C_{CO2}$, $C_{CO}$, etc.). $C_{C2H4}$=number of moles of C from $CH_4$ that were converted into $C_2H_4$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4s}$=number of moles of C from $CH_4$ that were converted into $C_4$ hydrocarbons ($C_4$s); $C_{CO2}$=number of moles of C from $CH_4$ that were converted into $CO_2$; $C_{CO}$=number of moles of C from $CH_4$ that were converted into CO; etc.

A $C_{2+}$ selectivity (e.g., selectivity to $C_{2+}$ hydrocarbons) refers to how much $C_2H_4$, $C_3H_6$, $C_2H_2$, $C_2H_6$, $C_3H_8$, and $C_4$s were formed divided by the total products formed, including $C_2H_4$, $C_3H_6$, $C_2H_2$, $C_2H_6$, $C_3H_8$, $C_4$s, $CO_2$ and CO. For example, the $C_{2+}$ selectivity can be calculated by using equation (3):

$$C_{2+} \text{ selectivity} = \frac{2C_{C_2H_4} + 2C_{C_2H_6} + 2C_{C_2H_2} + 3C_{C_3H_6} + 3C_{C_3H_8} + 4C_{C_4s}}{2C_{C_2H_4} + 2C_{C_2H_6} + 2C_{C_2H_2} + 3C_{C_3H_6} + 3C_{C_3H_8} + 4C_{C_4s} + C_{CO_2} + C_{CO}} \times 100\% \quad (3)$$

As will be appreciated by one of skill in the art, if a specific product and/or hydrocarbon product is not produced in a certain OCM reaction/process, then the corresponding $C_{Cx}$ is 0, and the term is simply removed from selectivity calculations.

It can be seen from FIG. 2C that $C_{2+}$ selectivity for the novel catalyst composition catalyst #2 is higher when compared with the $C_{2+}$ selectivity for the un-doped catalyst #1 at a much lower ignition temperature. For an OCM reaction, selectivity should be lower at lower temperatures, but catalyst #2 shows higher selectivity than catalyst #1, which indicates that Ag promotion improves catalyst selectivity.

Further, from FIGS. 2A, 2B, and 2C, it can be seen that the best performing catalyst (catalyst #2) was obtained by doping metal oxides with Ag. Catalyst #3 (Ag only, supported on $SiO_2$) shows almost no methane and oxygen conversions across a wide temperature range. Catalyst #1 showed ignition at 480° C., wherein 99.6% oxygen conversion and 24.4% methane conversion were obtained. For catalyst #2, Ag content was the same as for catalyst #3. Catalyst #2 showed ignition at 300° C. (which is 180° C. lower than the ignition temperature for un-promoted catalyst #1), wherein 100.0% oxygen conversion and 24.6% methane conversion were obtained. In can be seen clearly that Ag promotion increases catalyst activity significantly. Due to almost no activity for catalyst #3 at 300° C., it can be concluded that the activity increase of the metal oxide doped with Ag catalyst #2 is not coming from an increase in methane activation. Therefore, it can be predicted that the increase in activity is due to the Ag promotion effect on the re-oxidation step of the reduced metal oxides. Without wishing to be limited by theory, with an increase in a catalyst re-oxidation step, which is believed to be the rate determining step for the OCM reaction, the total reaction rate can be increased in the presence of catalyst #2, such that the ignition temperature is reduced. Further, without wishing to be limited by theory, catalyst #2 shows higher selectivity than catalyst #1, owing to Ag increasing the rate of the re-oxidation step, triggering an increased rate of methane activation and an increased rate of methane radical formation. Further, without wishing to be limited by theory, due to a coupling step to form $C_{2+}$ hydrocarbons being second order with respect to a methane radical concentration, an increase in methane radical formation will increase the $C_{2+}$ selectivity. As a result, with Ag promotion on metal oxides, both catalyst activity and selectivity are improved.

Example 3

OCM reactions were conducted by using catalysts prepared as described in Example 1 as follows. A mixture of methane and oxygen along with an internal standard, an inert gas (neon) were fed to a quartz reactor with an internal diameter (I.D.) of 4 mm heated by traditional clamshell furnace. A catalyst (e.g., catalyst bed) loading was 20 mg, and total flow rates of reactants was 160 cc/min. The reactor was first heated to a desired temperature under an inert gas flow and then a desired gas mixture was fed to the reactor. All OCM reactions were conducted at a methane to oxygen molar ratio of 4.

Methane conversion was calculated according to equation (1). Methane conversion for various catalyst compositions (e.g., catalysts #2, #4, and #5) were compared with the methane conversion for the un-doped catalyst #1, and the data are displayed in FIG. 3. It can be seen that the ignition temperature of catalyst #2 was lowered to 300° C. from 480° C. for un-doped catalyst #1. Catalyst #4 ignited at 350° C., which was also significantly lower than 480° C. for un-doped catalyst #1. The results in FIG. 3 indicate that doping with nano Ag increases catalyst activity significantly, and as a result the ignition temperature is lowered.

Figure 4:
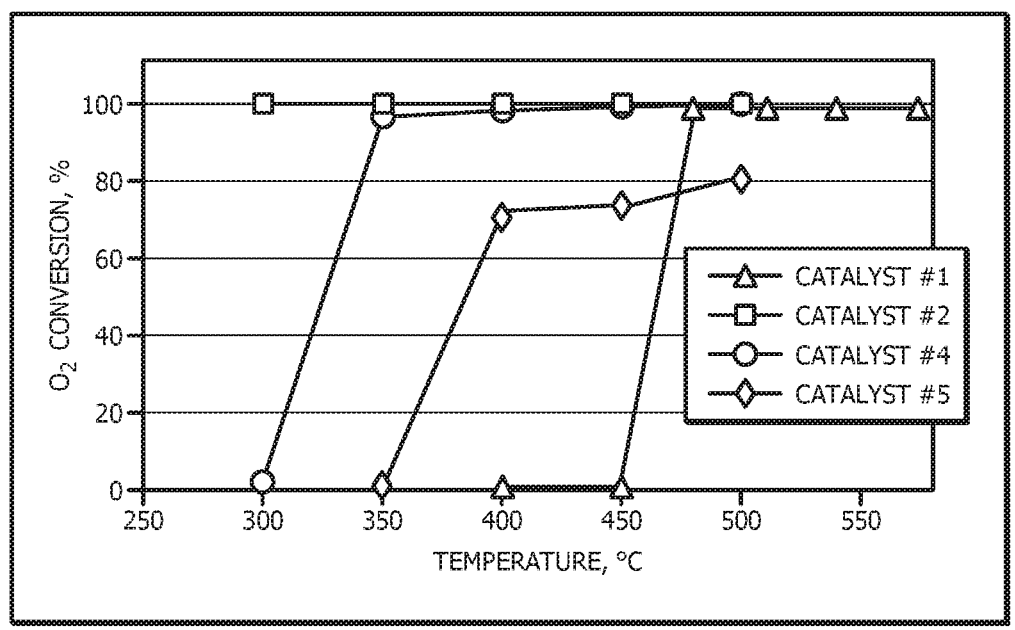
FIG. 4 displays another graph of oxygen conversion in an OCM reaction as a function of temperature for various catalysts.

FIG. 4 displays oxygen conversions for the novel catalyst compositions (e.g., catalysts #2, #4, and #5) as compared with the un-doped catalyst #1. For example, the oxygen conversion can be calculated by using equation (2). For catalyst #2, at 300° C. ignition temperature, 100% oxygen conversion was obtained. For catalyst #4, at ignition, close to 100% oxygen conversion was also obtained. When comparing un-doped catalyst #1, catalyst #2 and catalyst #4, it can be observed that catalyst #2 and catalyst #4 achieve 100% $O_2$ conversion at much lower temperatures than un-doped catalyst #1.

Figure 5:
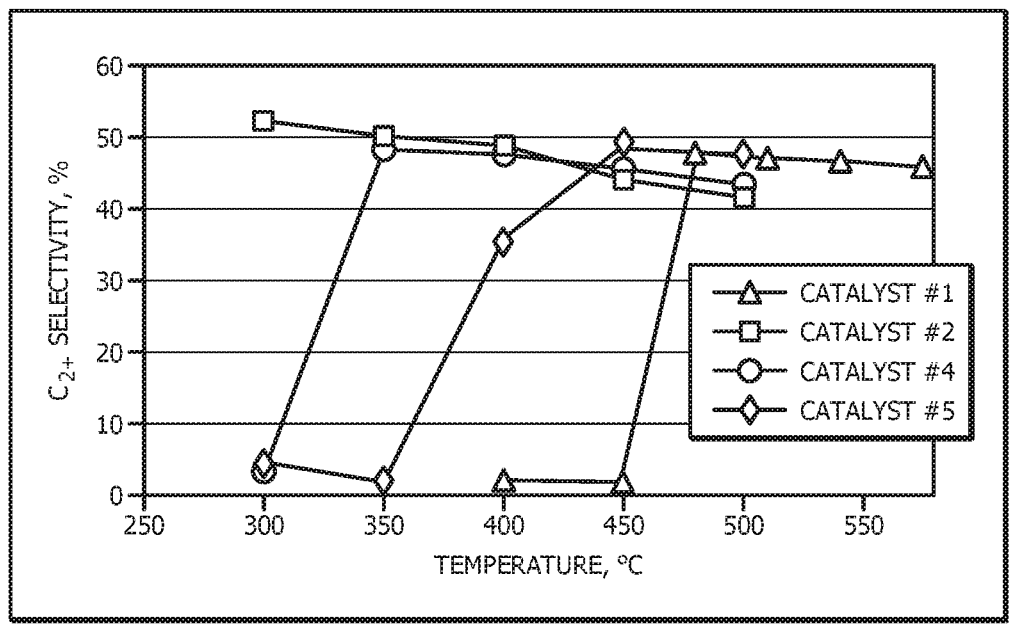
FIG. 5 displays another graph of $C_{2+}$ selectivity in an OCM reaction as a function of temperature for various catalysts.

FIG. 5 displays $C_{2+}$ selectivity values for the novel catalyst compositions (e.g., catalysts #2, #4, and #5) as compared with the un-doped catalyst #1, wherein the $C_{2+}$ selectivity values were calculated according to equation (3).

It can be seen from FIG. 5 that $C_{2+}$ selectivity for the novel catalyst composition catalyst #2 is higher when compared with the $C_{2+}$ selectivity for the un-doped catalyst #1 at a much lower ignition temperature. For an OCM reaction, selectivity should be lower at lower temperatures, but catalyst #2 shows higher selectivity than catalyst #1, which indicates that Ag promotion improves catalyst selectivity.

Figure 3:
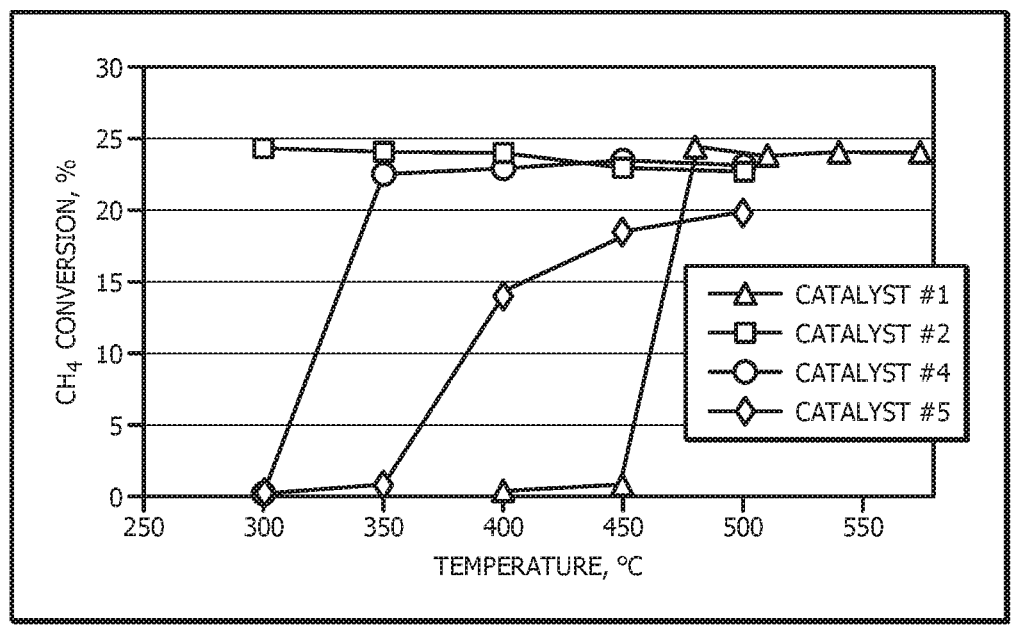
FIG. 3 displays another graph of methane conversion in an OCM reaction as a function of temperature for various catalysts.

Further, from FIGS. 3, 4, and 5, it can be seen that the best performing catalyst (catalyst #2) was obtained without thermally treating the OCM catalyst composition at temperatures above about 125° C. Without wishing to be limited by theory, the Ag particles could melt or partially melt and/or soften, and perhaps combine together, while thermally treating the catalyst at temperatures above 100° C., thereby lowering the overall performance of the catalyst. Further, without wishing to be limited by theory, while the catalysts are exposed to high temperatures during the OCM reaction, a gaseous environment to which the catalyst is exposed during thermally treating the catalyst is different than a gaseous environment to which the catalyst is exposed during an OCM reaction, and as such an effect of high temperatures on catalyst performance could be different in different gaseous environments.

Ag Promoted Mn—$Na_2WO_4$/$SiO_2$ Catalyst

Example 4

OCM catalyst compositions were prepared as follows. A 1.0% Ag—Mn—$Na_2WO_4$/$SiO_2$ catalyst (catalyst #6) was prepared as follows. Silica gel (18.6 g, Davisil® Grade 646) was used after drying overnight. $Mn(NO_3)_2 \cdot 4H_2O$ (1.73 g) was dissolved in deionized water (18.6 mL), and then added dropwise onto the silica gel and the material obtained was dried at 125° C. overnight. $AgNO_3$ (0.32 g) was dissolved in deionized water (18.6 mL), and the solution obtained was added dropwise onto the dried manganese silica gel and the material obtained was dried at 125° C. overnight. $Na_2WO_4 \cdot 4H_2O$ (1.13 g) was dissolved in deionized water (18.6 mL), and the solution obtained was added onto the dried manganese silica material above. The resultant material obtained was dried at 125° C. overnight and calcined at 800° C. for 6 hours under airflow to produce catalyst #6.

A Mn—$Na_2WO_4$/$SiO_2$ catalyst (catalyst #7) was prepared as follows. Silica gel (18.6 g, Davisil® Grade 646) was used after drying overnight. $Mn(NO_3)_2 \cdot 4H_2O$ (1.73 g) was dissolved in deionized water (18.6 mL), and then added dropwise onto the silica gel. The resulting manganese impregnated silica material was dried overnight. $Na_2WO_4 \cdot 4H_2O$ (1.13 g) was dissolved in deionized water (18.6 mL), and the solution obtained was added onto the dried manganese silica material above. The resulting material obtained was dried overnight at 125° C., and then calcined at 800° C. for 6 hours under airflow to obtain the Mn—$Na_2WO_4$/$SiO_2$ catalyst.

Example 5

OCM reactions were conducted by using catalysts prepared as described in Examples 1 and 4 (catalyst #3, #6, and #7) as follows. A mixture of methane and oxygen along with an internal standard, an inert gas (neon) were fed to a quartz reactor with an internal diameter (I.D.) of 4 mm heated by traditional clamshell furnace. A catalyst (e.g., catalyst bed) loading was 100 mg, and total flow rate of reactants was 33.3 cc/min. The reactor was first heated to a desired temperature under an inert gas flow and then a desired gas mixture was fed to the reactor. All OCM reactions were conducted at a methane to oxygen molar ratio of 7.4. Methane conversion, oxygen conversion and $C_{2+}$ selectivity were calculated as described in Example 2.

Figure 6A:
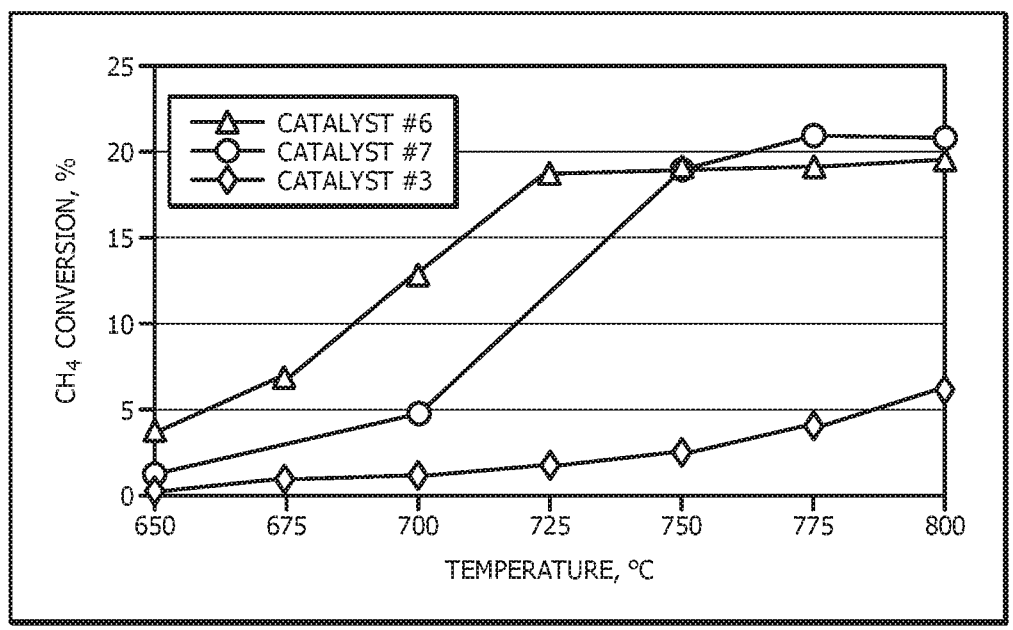
FIG. 6A displays yet another graph of methane conversion in an OCM reaction as a function of temperature for various catalysts.
Figure 6B:
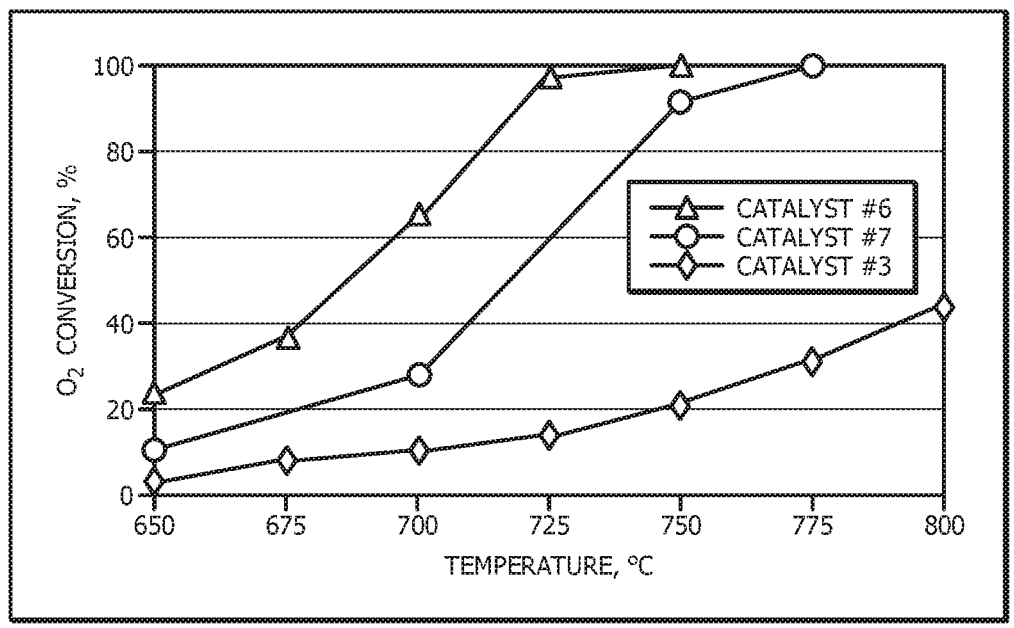
FIG. 6B displays yet another graph of oxygen conversion in an OCM reaction as a function of temperature for various catalysts.
Figure 6C:
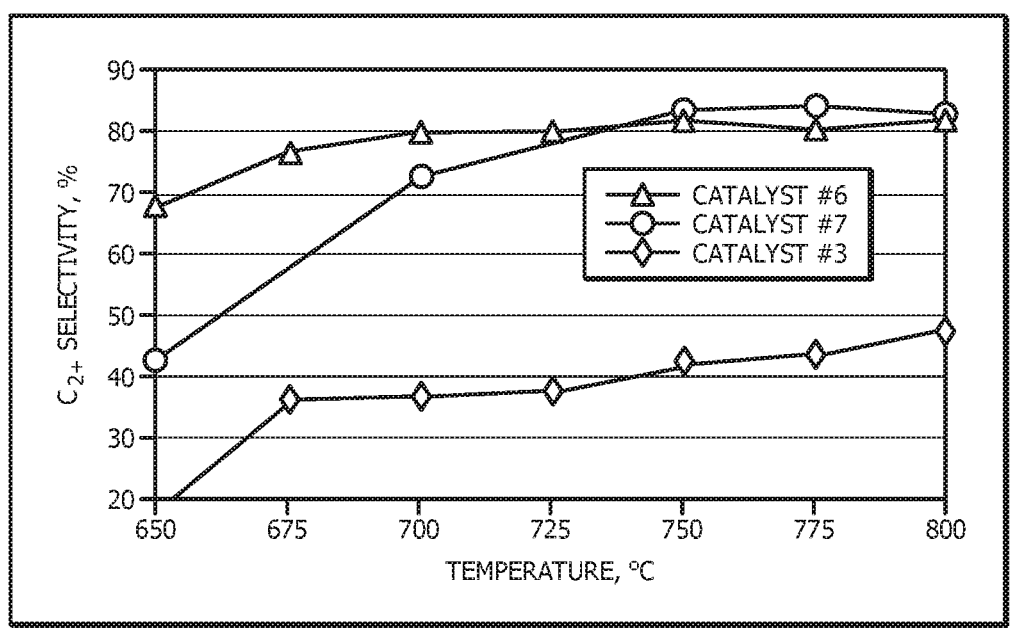
FIG. 6C displays yet another graph of $C_{2+}$ selectivity in an OCM reaction as a function of temperature for various catalysts.

From FIGS. 6A, 6B, and 6C, it can be seen that the best performing catalyst (catalyst #6) was obtained by doping metal oxides with Ag. Catalyst #3 (Ag only, supported on $SiO_2$) showed very low methane and oxygen conversions across a wide temperature range. The un-doped catalyst #7 showed much higher conversions when compared to catalyst #3. For catalyst #6, Ag content was the same as for catalyst #3. Catalyst #6 showed much higher conversions when compared to catalyst #7. For example, as it can be seen from FIG. 6A, at 700° C., methane conversion is 4.8% for catalyst #7; 1.0% for catalyst #3; and 12.8% for catalyst #6. This increase in methane conversion for catalyst #6 is much higher than the simple sum of methane conversions for catalysts #3 and #7. Similarly to the conclusions regarding catalyst #2, and without wishing to be limited by theory, due to the low activity of catalyst #3, it can be concluded that the catalytic activity increase for catalyst #6 is not coming from an increase in methane activation, but rather from an increase in the rate of the catalyst re-oxidation step due to the Ag promotion effect. Further, without wishing to be limited by theory, with an increase in the rate of the catalyst re-oxidation step, which is believed to be the rate determining step for the OCM reaction, the total reaction rate can be increased in the presence of catalyst #6.

FIG. 6C displays the $C_{2+}$ selectivities for catalysts #3, #6, and #7. Catalyst #6 displays a higher selectivity when compared to the undoped catalyst #7, which is consistent with the results observed for the doped catalyst #2 versus the undoped catalyst #1 displayed in FIG. 2C. As a result, it can be concluded that silver doping of metal oxides leads to both improved selectivity and improved catalytic activity.

Example 6

Preparation of Comparative Catalyst Mn—$Na_2WO_4$/$SiO_2$

Silica gel (18.6, Davisil® Grade 646, W. R. Grace and Company, USA) was used after drying overnight. $Mn(NO_3)_2 \cdot 4H_2O$ (1.73 g) was dissolved in deionized water (18.6 mL), and then added dropwise onto the silica gel. The resulting manganese impregnated silica material was dried overnight. $Na_2WO_4 \cdot 4H_2O$ (1.13 g) was dissolved in deionized water (18.6 mL), and the solution obtained was added onto the dried manganese silica material above. The resulting material obtained was dried overnight at 125° C., and then calcined at 800° C. for 6 hours under airflow to obtain the Mn—$Na_2WO_4$/$SiO_2$ catalyst.

Example 7

Preparation of 1.0% Ag—Mn—$Na_2WO_4$/$SiO_2$

Silica gel (18.6, Davisil® Grade 646) was used after drying overnight. $Mn(NO_3)_2 \cdot 4H_2O$ (1.73 g) was dissolved in deionized water (18.6 mL), and then added dropwise onto the silica gel, and the material obtained was dried at 125° C. overnight. $AgNO_3$ (0.32 g) was dissolved in deionized water (18.6 mL), the solution obtained was added dropwise onto the dried manganese silica gel, and the material obtained was dried at 125° C. overnight. $Na_2WO_4 \cdot 4H_2O$ (1.13 g) was dissolved in deionized water (18.6 mL), and the solution obtained was added onto the dried manganese silica material above. The resultant material obtained was dried at 125° C. overnight and calcined at 800° C. for 6 hours under airflow.

Example 8

Preparation of 5.0% Ag—Mn—Na$_2$WO$_4$/SiO$_2$

Silica gel (18.6, Davisil® Grade 646) was used after drying overnight. Mn(NO$_3$)$_2$.4H$_2$O (1.73 g) was dissolved in deionized water (18.6 mL), and then added dropwise onto the silica gel, and the material obtained was dried at 125° C. overnight. AgNO$_3$ (1.6 g) was dissolved in deionized water (18.6 mL), the solution obtained was added dropwise onto the dried manganese silica gel and the material obtained was dried at 125° C. overnight. Na$_2$WO$_4$.4H$_2$O (1.13 g) was dissolved in deionized water (18.6 mL), and the solution obtained was added onto the dried manganese silica material above. The resultant material obtained was dried at 125° C. overnight and calcined at 800° C. for 6 hours under airflow.

Example 9

Preparation of 1.0% Ag—Mn—Na$_2$WO$_4$/SiO$_2$

AgNO$_3$ (0.32 g) was dissolved in deionized water (18.6 mL), and the solution obtained was added dropwise onto the calcined catalyst (20 g) from Example 6. The material obtained was dried overnight at 125° C.

Example 10

Preparation of 1.0% Ag—Mn—Na$_2$WO$_4$/SiO$_2$

AgNO$_3$ (0.32 g) was dissolved in deionized water (18.6 mL), and the solution obtained was added dropwise onto the calcined catalyst (20 g) from Example 6. The material obtained was dried overnight at 125° C., and then calcined at 300° C. for 5 hours under airflow.

Example 11

Preparation of 1.0% Ag—Mn—Na$_2$WO$_4$/SiO$_2$

AgNO$_3$ (0.32 g) was dissolved in deionized water (18.6 mL), and the solution obtained was added dropwise onto the calcined catalyst (20 g) from Example 6. The material obtained was dried overnight at 125° C., and then calcined at 500° C. for 5 hours under airflow.

Example 12

Comparison of Methane Conversion Under Different Reaction Temperatures

The catalytic performances on the catalysts prepared as described in Examples 6-11 were compared. A fixed bed catalyst reactor was filled with 100 mg of the catalytic materials of Example 7-11 (Ag—Mn—Na$_2$WO$_4$/SiO$_2$) or the comparative catalyst (Mn—Na$_2$WO$_4$/SiO$_2$) of Example 6. The reactor was heated to the required temperature, and a mixture of methane and oxygen at a fixed CH$_4$:O$_2$ ratio of 7.4 was fed to the reactor at a total flow rate of 33.3 sccm.

Figure 7:
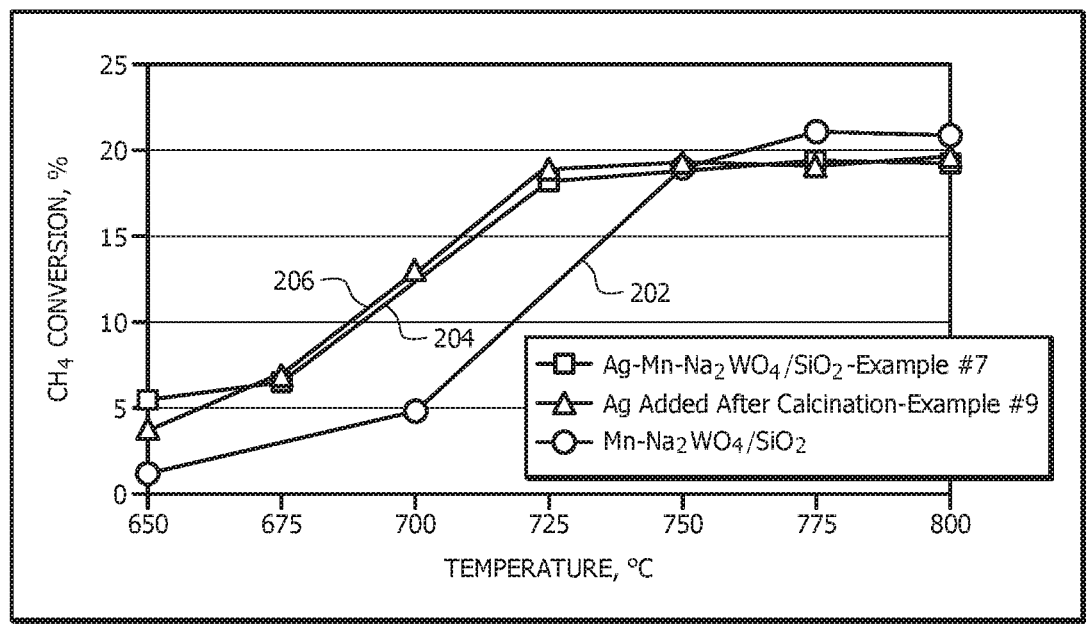
FIG. 7 displays still yet another graph of methane conversion in an OCM reaction as a function of temperature for various catalysts.

Methane conversion was calculated on the basis of the difference of inlet and outlet concentrations of methane, as described in Example 2. Percent methane conversion for comparative sample (undoped) Mn—Na$_2$WO$_4$/SiO$_2$ and silver doped Mn—Na$_2$WO$_4$/SiO$_2$ catalysts of the present disclosure obtained from Examples 7 and 9 are shown in FIG. 7. Data line 202 is percent methane conversion using undoped Mn—Na$_2$WO$_4$/SiO$_2$. Data line 204 is percent methane conversion using Mn—Na$_2$WO$_4$/SiO$_2$ doped with 1 wt. % silver impregnated onto silica support before calcination (Example 7). Data line 206 is percent methane conversion using Mn—Na$_2$WO$_4$/SiO$_2$ doped with 1 wt. % silver impregnated onto calcined Mn—Na$_2$WO$_4$/SiO$_2$ catalyst (Example 9). The silver doped catalyst made by different methods gave the same conversion under a lower temperature, indicating a higher activity in comparison to undoped comparative catalyst. To conclude, the use of a silver doped catalyst allows the reaction to be operated under a lower temperature, which benefits the catalyst stability.

Example 13

Comparison of C$_{2+}$ Selectivity Under Different Reaction Temperatures

A fixed bed catalyst reactor was filled with a 100 mg of catalytic materials of the current disclosure (Examples 7 and 9) or the comparative catalyst (Mn—Na$_2$WO$_4$/SiO$_2$). The reactor was heated to the required temperature, and a mixture of methane and oxygen at a fixed CH$_4$:O$_2$ ratio of 7.4 was fed to the reactor at a flow rate of 33.3 sccm.

Figure 8:
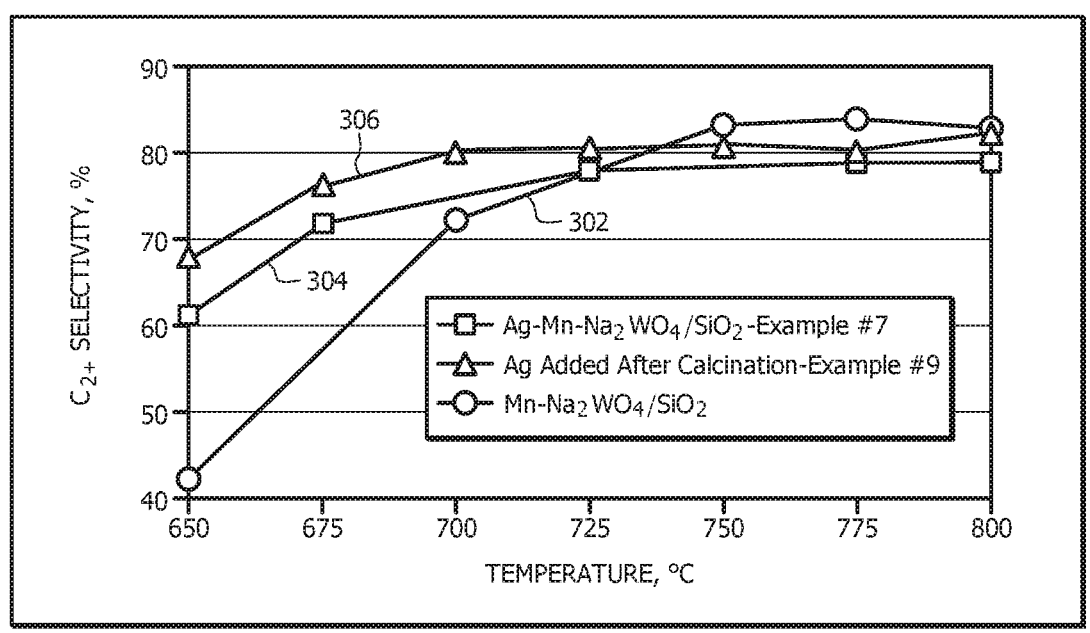
FIG. 8 displays still yet another graph of $C_{2+}$ selectivity in an OCM reaction as a function of temperature for various catalysts.

The C$_{2+}$ selectivities obtained at different reaction temperatures are shown in FIG. 8. Data line 302 is the comparative sample Mn—Na$_2$WO$_4$/SiO$_2$ of Example 6, data line 304 is the catalyst of the current disclosure from Example 7, and data line 306 is the catalyst of the current disclosure from Example 9. The C$_{2+}$ selectivity was calculated on the basis of concentrations of C$_{2+}$ products in comparison all the converted amount of methane, as described in Example 2. At lower temperature, however, the C$_{2+}$ selectivity obtained with the silver promoted catalyst was higher than the C$_{2+}$ selectivity obtained with the comparative catalyst. At higher reaction temperatures, the selectivities obtained with these three catalysts were almost the same. Therefore, silver promoted catalysts offer higher selectivity over a broaden temperature range than unpromoted catalysts. These results provide significant advantages, for example, in a commercial reactor where the temperature profile across axial and radial directions in the catalyst bed can vary as much as 200° C., for example as outlined in Lee et al., Fuel, 106 (2013) 851, which is incorporated by reference herein in its entirety. Therefore, the final selectivity obtained through the commercial reactor is the sum of selectivity contribution from different temperatures. With the selectivities shown in FIG. 8, it can be predicted that the final selectivity of a commercial reactor with a Ag doped catalyst will be higher than that with undoped comparative catalyst.

Table 1 lists the catalysts made with different Ag contents, the percent methane conversion and the percent C$_{2+}$ selectivity under the same testing conditions as in FIG. 7 (Examples 12 and 13). Surprisingly, increasing the silver content to 5.0% in the catalyst did not affect the catalyst performance

TABLE 1

| Catalyst Example | Ag content (%) | CH$_4$ conversion (%) | C$_{2+}$ selectivity (%) |
|---|---|---|---|
| 7 | 1.0 | 18.1 | 78.0 |
| 8 | 5.0 | 13.7 | 78.3 |

Table 2 lists the catalysts prepared (e.g., Examples 9-11), the different heat treatment temperatures, the percent methane conversion, and the percent C$_{2+}$ selectivity obtained under the same testing conditions as in Examples 12 and 13. From the results, it was concluded that the second heat treatment temperature has minimal impact on the performance of the silver doped catalyst.

TABLE 2

| Catalyst Example | Calcination temperatures (° C.) | $CH_4$ conversion (%) | $C_{2+}$ selectivity (%) |
|---|---|---|---|
| 9 | 125 | 18.7 | 80.2 |
| 10 | 300 | 18.8 | 80.5 |
| 11 | 500 | 18.8 | 80.4 |

The theoretical limit of $C_{2+}$ selectivity ($S_{lim}$) has been established for oxidative coupling of methane reactions, for example as outlined in Sinev et al., in "Kinetics of oxidative coupling of methane: Bridging the gap between comprehension and description", *J. Natural Gas Chemistry*, 2009, Vol. 18, p. 273; and Labinger, in "Oxidative Coupling Of Methane: An Inherent Limit to Selectivity?," *Catalysis Letters*, 1988, Vol. 1, pg. 371; each of which is incorporated by reference herein in its entirety. A comparison of the $C_{2+}$ selectivity of the silver promoted catalyst of the current embodiments and the $S_{lim}$ is shown in Table 3. At a methane to oxygen ratio of 7.4, a reaction temperature of 725° C., and 18% methane conversion, the selectivity limit ($S_{lim}$) was 75.5%. The selectivity obtained with the Ag promoted catalyst of the current disclosure showed a higher selectivity than the limit. The comparative (undoped) catalyst can only achieve 13.4% methane conversion, and if the conversion was increased to 18% by changing the residence time, the selectivity of the undoped catalyst would be lower and would be predicted to be lower than $S_{lim}$.

TABLE 3

| | $C_{2+}$ selectivity (%) |
|---|---|
| $S_{lim}$ | 75.5 |
| Example 7 catalyst | 78.0 |
| Example 9 catalyst | 80.2 |

Overall, the silver doped catalyst of the present disclosure showed higher activity (e.g., higher $C_{2+}$ selectivity), which can allow for a reactor to be operated under lower temperature conditions, thereby increasing catalyst stability. The silver doped catalyst also showed higher selectivity under low a reaction temperature and is predicted to achieve a higher selectivity and longer catalyst life in a commercial reactor, when compared to conventional (undoped) catalysts. The selectivity obtained using the silver doped catalysts at 725° C. was found to be higher than the known limit of $C_{2+}$ selectivity based on published data.

Without wishing to be limited by theory, and based on the above examples, the promotion effect of Ag on OCM catalysts is to improve (e.g., increase) the rate of the re-oxidation step of the catalyst, which is believed to be the rate determining step for the OCM reaction for all OCM catalysts. Consequently, Ag can promote any OCM catalysts with the same effects as demonstrated in Examples 1-13, i.e., Ag can improve activity and selectivity for any OCM catalysts.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

Additional Disclosure

Aspects Group A

A first aspect, which is an oxidative coupling of methane (OCM) catalyst composition doped with silver (Ag).

A second aspect, which is the OCM catalyst composition of the first aspect, wherein the wherein the OCM catalyst composition comprises one or more oxides doped with Ag; wherein the one or more oxides comprises a single metal oxide, mixtures of single metal oxides, a mixed metal oxide, mixtures of mixed metal oxides, or combinations thereof; and wherein the one or more oxides is not $La_2O_3$ alone.

A third aspect, which is the OCM catalyst composition of the second aspect, wherein the single metal oxide comprises one metal cation selected from the group consisting of alkali metal cations, alkaline earth metal cations, rare earth element cations, and cations of elements that can form oxides with redox properties.

A fourth aspect, which is the OCM catalyst composition of any one of the first through the third aspects, wherein the mixed metal oxide comprises two or more different metal cations, wherein each metal cation can be independently selected from the group consisting of alkali metal cations, alkaline earth metal cations, rare earth element cations, and cations of elements that can form oxides with redox properties.

A fifth aspect, which is the OCM catalyst composition of any one of the first through the fourth aspects, wherein the one or more oxides comprises alkali metal oxides, alkaline earth metal oxides, rare earth element oxides, oxides of elements that can form oxides with redox properties, or combinations thereof.

A sixth aspect, which is the OCM catalyst composition of the fifth aspect, wherein the alkali metal oxides comprise cations of lithium (Li), sodium (Na), potassium (K), rubidium (Rb), cesium (Cs), or combinations thereof.

A seventh aspect, which is the OCM catalyst composition of any one of the first through the sixth aspects, wherein the alkaline earth metal oxides comprise cations of magnesium (Mg), calcium (Ca), strontium (Sr), barium (Ba), or combinations thereof.

An eighth aspect, which is the OCM catalyst composition of any one of the first through the seventh aspects, wherein the rare earth metal oxides comprise cations of lanthanum (La), cerium (Ce), praseodymium (Pr), neodymium (Nd), samarium (Sm), europium (Eu), dysprosium (Dy), holmium (Ho), erbium (Er), ytterbium (Yb), or combinations thereof.

A ninth aspect, which is the OCM catalyst composition of any one of the first through the eighth aspects, wherein the oxides of elements that can form oxides with redox properties comprise cations of manganese (Mn), tungsten (W), vanadium (V), tin (Sn), antimony (Sb), phosphorus (P), arsenic (As), chromium (Cr), bismuth (Bi), gallium (Ga), rhenium (Re), lead (Pb), iron (Fe), cobalt (Co), nickel (Ni), copper (Cu), niobium (Nb), molybdenum (Mo), or combinations thereof.

A tenth aspect, which is the OCM catalyst composition of any one of the first through the ninth aspects comprising from about 0.1 wt. % to about 20 wt. % Ag.

An eleventh aspect, which is the OCM catalyst composition of any one of the first through the tenth aspects, wherein the Ag comprises Ag nanoparticles, Ag microparticles, Ag nanowires, or combinations thereof; wherein the Ag nanoparticles are characterized by an average size of from about 1 nm to about 500 nm; wherein the Ag microparticles are characterized by an average size of from about 0.5 microns to about 50 microns; and wherein the Ag nanowires are characterized by an average diameter of from about 1 nm to about 500 nm, and by an average length of from about 0.5 microns to about 50 microns.

A twelfth aspect, which is the OCM catalyst composition of any one of the first through the eleventh aspects further comprising a support, wherein at least a portion of the OCM catalyst composition contacts, coats, is embedded in, is supported by, and/or is distributed throughout at least a portion of the support; wherein the support comprises MgO, $Al_2O_3$, $SiO_2$, $ZrO_2$, or combinations thereof; and wherein the support is in the form of particles, pellets, monoliths, foams, honeycombs, or combinations thereof.

A thirteenth aspect, which is the OCM catalyst composition of any one of the first through the twelfth aspects, wherein the one or more oxides comprises $CeO_2$, $La_2O_3$—$CeO_2$, Ca/$CeO_2$, Mn/$Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, MnO—$W_2O_3$, MnO—$W_2O_3$—$Na_2O$, MnO—$W_2O_3$—$Li_2O$, SrO/$La_2O_3$, $Ce_2O_3$, La/MgO, $La_2O_3$—$CeO_2$—$Na_2O$, $La_2O_3$—$CeO_2$—CaO, $Na_2O$—MnO—$WO_3$—$La_2O_3$, $La_2O_3$—$CeO_2$—MnO—$WO_3$—SrO, Na—Mn—$La_2O_3$/$Al_2O_3$, Na—Mn—O/$SiO_2$, $Na_2WO_4$—Mn/$SiO_2$, $Na_2WO_4$—Mn—O/$SiO_2$, Na/Mn/O, $Na_2WO_4$, $Mn_2O_3$/$Na_2WO_4$, $Mn_3O_4$/$Na_2WO_4$, $MnWO_4$/$Na_2WO_4$, $MnWO_4$/$Na_2WO_4$, Mn/$WO_4$, $Na_2WO_4$/Mn, Sr/Mn—$Na_2WO_4$, or combinations thereof.

A fourteenth aspect, which is an oxidative coupling of methane (OCM) catalyst composition comprising a lanthanum (III) and cerium (IV) mixture doped with silver (Ag).

A fifteenth aspect, which is the OCM catalyst composition of the fourteenth aspect, wherein lanthanum (III) comprises $La_2O_3$, and optionally La(OH)$_3$.

A sixteenth aspect, which is the OCM catalyst composition of any one of the fourteenth and the fifteenth aspects, wherein cerium (IV) comprises $CeO_2$.

A seventeenth aspect, which is the OCM catalyst composition of any one of the fourteenth through the sixteenth aspects, wherein the Ag comprises Ag nanoparticles, Ag microparticles, Ag nanowires, or combinations thereof.

An eighteenth aspect, which is the OCM catalyst composition of any one of the fourteenth through the seventeenth aspects comprising (i) from about 0.1 wt. % to about 20 wt. % Ag; (ii) from about 45.0 wt. % to about 99.0 wt. % lanthanum (III); and (iii) from about 0.9 wt. % to about 50.0 wt. % cerium (IV).

A nineteenth aspect, which is a supported oxidative coupling of methane (OCM) catalyst capable of catalyzing an OCM reaction, the supported OCM catalyst comprising silver (Ag) doped Mn/$Na_2WO_4$ and a metal oxide support, wherein the supported OCM catalyst has greater $CH_4$ conversion and $C_{2+}$ hydrocarbon selectivity as compared to the $CH_4$ conversion and $C_{2+}$ hydrocarbon selectivity, respectively, of an otherwise similar Mn/$Na_2WO_4$ metal oxide supported OCM catalyst that has not been doped with Ag.

A twentieth aspect, which is the supported OCM catalyst of the nineteenth aspect, wherein the supported OCM catalyst's selectivity for $C_{2+}$ hydrocarbons is greater than a theoretical selectivity limit for $C_{2+}$ hydrocarbons for the oxidative coupling of methane reaction; and wherein the supported OCM catalyst's life is greater than the life of an otherwise similar Mn/$Na_2WO_4$ metal oxide supported OCM catalyst that has not been doped with Ag.

Aspects Group B

A first aspect, which is an oxidative coupling of methane (OCM) catalyst composition comprising one or more oxides doped with silver (Ag); wherein the one or more oxides comprises a single metal oxide, mixtures of single metal oxides, a mixed metal oxide, mixtures of mixed metal oxides, or combinations thereof; and wherein the one or more oxides is not $La_2O_3$ alone.

A second aspect, which is the OCM catalyst composition of the first aspect, wherein the single metal oxide comprises one metal cation selected from the group consisting of alkali metal cations, alkaline earth metal cations, rare earth element cations, and cations of elements that can form oxides with redox properties.

A third aspect, which is the OCM catalyst composition of any one of the first and the second aspects, wherein the mixed metal oxide comprises two or more different metal cations, wherein each metal cation can be independently selected from the group consisting of alkali metal cations, alkaline earth metal cations, rare earth element cations, and cations of elements that can form oxides with redox properties.

A fourth aspect, which is the OCM catalyst composition of any one of the first through the third aspects, wherein the one or more oxides comprises alkali metal oxides, alkaline earth metal oxides, rare earth element oxides, oxides of elements that can form oxides with redox properties, or combinations thereof.

A fifth aspect, which is the OCM catalyst composition of the fourth aspect, wherein the alkali metal oxides comprise cations of lithium (Li), sodium (Na), potassium (K), rubidium (Rb), cesium (Cs), or combinations thereof.

A sixth aspect, which is the OCM catalyst composition of any one of the first through the fifth aspects, wherein the alkaline earth metal oxides comprise cations of magnesium (Mg), calcium (Ca), strontium (Sr), barium (Ba), or combinations thereof.

A seventh aspect, which is the OCM catalyst composition of any one of the first through the sixth aspects, wherein the rare earth metal oxides comprise cations of lanthanum (La), cerium (Ce), praseodymium (Pr), neodymium (Nd), samarium (Sm), europium (Eu), dysprosium (Dy), holmium (Ho), erbium (Er), ytterbium (Yb), or combinations thereof.

An eighth aspect, which is the OCM catalyst composition any one of the first through the seventh aspects, wherein the oxides of elements that can form oxides with redox properties comprise cations of manganese (Mn), tungsten (W), vanadium (V), tin (Sn), antimony (Sb), phosphorus (P), arsenic (As), chromium (Cr), bismuth (Bi), gallium (Ga), rhenium (Re), lead (Pb), iron (Fe), cobalt (Co), nickel (Ni), copper (Cu), niobium (Nb), molybdenum (Mo), or combinations thereof.

A ninth aspect, which is the OCM catalyst composition of any one of the first through the eighth aspects comprising from about 0.1 wt. % to about 20 wt. % Ag.

A tenth aspect, which is the OCM catalyst composition of any one of the first through the ninth aspects, wherein the Ag comprises Ag nanoparticles, Ag microparticles, Ag nanowires, or combinations thereof; wherein the Ag nanoparticles are characterized by an average size of from about 1 nm to about 500 nm; wherein the Ag microparticles are characterized by an average size of from about 0.5 microns to about 50 microns; and wherein the Ag nanowires are characterized by an average diameter of from about 1 nm to about 500 nm, and by an average length of from about 0.5 microns to about 50 microns.

An eleventh aspect, which is the OCM catalyst composition of any one of the first through the tenth aspects further comprising a support, wherein at least a portion of the OCM catalyst composition contacts, coats, is embedded in, is supported by, and/or is distributed throughout at least a portion of the support; wherein the support comprises MgO, $Al_2O_3$, $SiO_2$, $ZrO_2$, or combinations thereof; and wherein the support is in the form of particles, pellets, monoliths, foams, honeycombs, or combinations thereof.

A twelfth aspect, which is the OCM catalyst composition of any one of the first through the eleventh aspects comprising from about 45.0 wt. % to about 99.0 wt. % lanthanum (III), and from about 0.9 wt. % to about 50.0 wt. % cerium (IV); wherein lanthanum (III) comprises $La_2O_3$ and optionally $La(OH)_3$; and wherein cerium (IV) comprises $CeO_2$.

A thirteenth aspect, which is the OCM catalyst composition of the eleventh aspect comprising a silver (Ag) doped $Mn/Na_2WO_4$ and a metal oxide support, wherein the catalyst has greater methane ($CH_4$) conversion and $C_{2+}$ hydrocarbon selectivity as compared to the same $Mn/Na_2WO_4$ metal oxide supported catalyst that has not been doped with Ag.

A fourteenth aspect, which is the OCM catalyst composition of any one of the first through the thirteenth aspects comprising a supported catalyst capable of catalyzing an oxidative couple of methane reaction, wherein the one or more oxides doped with silver (Ag) are supported on a metal oxide support, wherein the catalyst has greater methane ($CH_4$) conversion and $C_{2+}$ hydrocarbon selectivity as compared to the same supported catalyst that has not been doped with Ag.

A fifteenth aspect, which is the OCM catalyst composition of any one of the first through the fourteenth aspects, wherein the one or more oxides comprises $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, MnO—$W_2O_3$, MnO—$W_2O_3$—$Na_2O$, MnO—$W_2O_3$—$Li_2O$, $SrO/La_2O_3$, $Ce_2O_3$, La/MgO, $La_2O_3$—$CeO_2$—$Na_2O$, $La_2O_3$—$CeO_2$—CaO, $Na_2O$—MnO—$WO_3$—$La_2O_3$, $La_2O_3$—$CeO_2$—MnO—$WO_3$—SrO, Na—Mn—$La_2O_3/Al_2O_3$, Na—Mn—$O/SiO_2$, $Na_2WO_4$—$Mn/SiO_2$, $Na_2WO_4$—Mn—$O/SiO_2$, Na/Mn/O, $Na_2WO_4$, $Mn_2O_3/Na_2WO_4$, $Mn_3O_4/Na_2WO_4$, $MnWO_4/Na_2WO_4$, $MnWO_4/Na_2WO_4$, $Mn/WO_4$, $Na_2WO_4/Mn$, $Sr/Mn$—$Na_2WO_4$, or combinations thereof.

A sixteenth aspect, which is a method of making an oxidative coupling of methane (OCM) catalyst composition comprising (a) calcining one or more oxides and/or oxide precursors to form one or more calcined oxides, wherein the one or more oxides comprises a single metal oxide, mixtures of single metal oxides, a mixed metal oxide, mixtures of mixed metal oxides, or combinations thereof, wherein the one or more oxides is not $La_2O_3$ alone, and wherein the oxide precursors comprise oxides, nitrates, carbonates, hydroxides, or combinations thereof; (b) doping the one or more calcined oxides with silver (Ag) to form the OCM catalyst composition; and (c) optionally thermally treating the OCM catalyst composition.

A seventeenth aspect, which is the method of the sixteenth aspect, wherein (i) the one or more calcined oxides are doped with silver in the presence of a support; and/or (ii) the OCM catalyst composition is further contacted with a support.

An eighteenth aspect, which is a method for producing olefins comprising (a) introducing a reactant mixture to a reactor comprising an oxidative coupling of methane (OCM) catalyst composition, wherein the reactant mixture comprises methane ($CH_4$) and oxygen ($O_2$), wherein the OCM catalyst composition comprises one or more oxides doped with silver (Ag); wherein the one or more oxides comprises a single metal oxide, mixtures of single metal oxides, a mixed metal oxide, mixtures of mixed metal oxides, or combinations thereof; (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture.

A nineteenth aspect, which is the method of the eighteenth aspect, wherein the OCM reaction is characterized by (i) an ignition temperature that is decreased by from about 50° C. to about 500° C., when compared to an ignition temperature of an otherwise similar OCM reaction conducted in the presence of an OCM catalyst composition comprising one or more oxides without the Ag; and/or (ii) a reaction temperature needed to achieve a 100% oxygen conversion that is decreased by from about 20° C. to about 500° C., when compared to a reaction temperature needed to achieve a 100% oxygen conversion of an otherwise similar OCM reaction conducted in the presence of an OCM catalyst composition comprising one or more oxides without the Ag.

A twentieth aspect, which is a method of producing $C_{2+}$ hydrocarbons from an oxidative coupling of methane (OCM) reaction, the method comprising contacting a reactant feed that includes a methane containing gas and an oxygen containing gas with an OCM catalyst composition to produce a product stream comprising $C_{2+}$ hydrocarbons; wherein the OCM catalyst composition comprises one or more oxides doped with silver (Ag); wherein the one or more oxides comprises a single metal oxide, mixtures of single metal oxides, a mixed metal oxide, mixtures of mixed metal oxides, or combinations thereof; and wherein a selectivity to $C_{2+}$ hydrocarbons is from about 60% to about 90% at a reaction temperature of from about 200° C. to about 900° C.

A twenty-first aspect, which is a system for producing $C_{2+}$ hydrocarbons, the system comprising (a) an inlet for a reactant feed comprising methane and oxygen; (b) a reaction zone that is configured to be in fluid communication with the inlet, wherein the reaction zone comprises an oxidative coupling of methane (OCM) catalyst composition; wherein the OCM catalyst composition comprises one or more oxides doped with silver (Ag); wherein the one or more oxides comprises a single metal oxide, mixtures of single metal oxides, a mixed metal oxide, mixtures of mixed metal oxides, or combinations thereof; wherein the reaction zone comprises the reactant feed and a product stream; and wherein a temperature of the reactant feed at the inlet, just prior to the inlet, during contact with the OCM catalyst composition, or combinations thereof is from about 200° C. to about 800° C.; and (c) an outlet configured to be in fluid communication with the reaction zone and configured to remove the product stream comprising $C_{2+}$ hydrocarbons from the reaction zone.

Aspects Group C

A first aspect, which is an oxidative coupling of methane (OCM) catalyst composition comprising a lanthanum (III) and cerium (IV) mixture doped with silver (Ag).

A second aspect, which is the OCM catalyst composition of the first aspect, wherein lanthanum (III) comprises $La_2O_3$.

A third aspect, which is the composition of any one of the first and the second aspects, wherein lanthanum (III) further comprises $La(OH)_3$.

A fourth aspect, which is the OCM catalyst composition of any one of the first through the third aspects, wherein cerium (IV) comprises $CeO_2$.

A fifth aspect, which is the OCM catalyst composition of any one of the first through the fourth aspects, wherein the Ag comprises Ag nanoparticles, Ag microparticles, Ag nanowires, or combinations thereof.

A sixth aspect, which is the OCM catalyst composition of the fifth aspect, wherein the Ag nanoparticles are characterized by an average size of from about 1 nm to about 500 nm.

A seventh aspect, which is the OCM catalyst composition of the fifth aspect, wherein the Ag microparticles are characterized by an average size of from about 0.5 microns to about 50 microns.

An eighth aspect, which is the OCM catalyst composition of the fifth aspect, wherein the Ag nanowires are characterized by an average diameter of from about 1 nm to about 500 nm, and by an average length of from about 0.5 microns to about 50 microns.

A ninth aspect, which is the OCM catalyst composition of any one of the first through the eighth aspects comprising from about 0.1 wt. % to about 20 wt. % Ag.

A tenth aspect, which is the OCM catalyst composition of any one of the first through the ninth aspects comprising from about 45.0 wt. % to about 99.0 wt. % lanthanum (III).

An eleventh aspect, which is the composition of any one of the first through the tenth aspects comprising from about 0.9 wt. % to about 50.0 wt. % cerium (IV).

A twelfth aspect, which is the composition of any one of the first through the eleventh aspects further comprising a support, wherein at least a portion of the OCM catalyst composition contacts, coats, is embedded in, is supported by, and/or is distributed throughout at least a portion of the support.

A thirteenth aspect, which is the composition of the twelfth aspect, wherein the support comprises MgO, $Al_2O_3$, $SiO_2$, $ZrO_2$, or combinations thereof.

A fourteenth aspect, which is the composition of any one of the first through the thirteenth aspects, wherein the support is in the form of particles, pellets, monoliths, foams, honeycombs, or combinations thereof.

A fifteenth aspect, which is the composition of any one of the first through the fourteenth aspects formed into pellets and/or tablets.

A sixteenth aspect, which is the composition of the fifteenth aspect, wherein the pellets comprise a binder.

A seventeenth aspect, which is the composition of the fifteenth aspect, wherein the tablets exclude a binder.

An eighteenth aspect, which is a method of making an oxidative coupling of methane (OCM) catalyst composition comprising (a) forming a lanthanum (III) and cerium (III) mixture; (b) calcining the lanthanum (III) and cerium (III) mixture to form a lanthanum (III) and cerium (IV) mixture; (c) doping the lanthanum (III) and cerium (IV) mixture with silver (Ag) to form the OCM catalyst composition; and (d) optionally thermally treating the OCM catalyst composition.

A nineteenth aspect, which is the method of the eighteenth aspect further comprising forming the OCM catalyst composition into pellets by extrusion.

A twentieth aspect, which is the method of the eighteenth aspect further comprising forming the OCM catalyst composition into tablets under pressure.

A twenty-first aspect, which is the method of the eighteenth aspect, wherein (i) the lanthanum (III) and cerium (III) mixture is formed in the presence of a support; and/or (ii) the lanthanum (III) and cerium (IV) mixture is doped with Ag in the presence of a support.

A twenty-second aspect, which is the method of the eighteenth aspect further comprising contacting the OCM catalyst composition with a support.

A twenty-third aspect, which is the method of any one of the eighteenth through the twenty-second aspects, wherein the Ag comprises Ag nanoparticles, Ag microparticles, Ag nanowires, or combinations thereof.

A twenty-fourth aspect, which is an OCM catalyst produced by the method of the eighteenth aspect.

A twenty-fifth aspect, which is a method for producing olefins comprising (a) introducing a reactant mixture to a reactor comprising an oxidative coupling of methane (OCM) catalyst composition, wherein the reactant mixture comprises methane ($CH_4$) and oxygen ($O_2$), wherein the OCM catalyst composition comprises a lanthanum (III) and cerium (IV) mixture doped with silver (Ag); (b) allowing at least a portion of the reactant mixture to contact at least a portion of the OCM catalyst composition and react via an OCM reaction to form a product mixture comprising olefins; (c) recovering at least a portion of the product mixture from the reactor; and (d) recovering at least a portion of the olefins from the product mixture.

A twenty-sixth aspect, which is the method the twenty-fifth aspect, wherein the OCM reaction is characterized by an ignition temperature of from about 200° C. to about 500° C.

A twenty-seventh aspect, which is the method of any one of the twenty-fifth and the twenty-sixth aspects, wherein the OCM reaction is characterized by an ignition temperature that is decreased by from about 50° C. to about 300° C., when compared to an ignition temperature of an otherwise similar OCM reaction conducted in the presence of an OCM catalyst composition comprising a lanthanum (III) and cerium (IV) mixture without the Ag.

A twenty-eighth aspect, which is the method of any one of the twenty-fifth through the twenty-seventh aspects, wherein the reactor comprises a catalyst bed comprising the OCM catalyst composition, wherein the catalyst bed is characterized by a catalyst bed temperature of from about 200° C. to about 1,100° C.

A twenty-ninth aspect, which is the method of any one of the twenty-fifth through the twenty-eighth aspects, wherein the reactor comprises a catalyst bed comprising the OCM catalyst composition, wherein the catalyst bed is characterized by a catalyst bed temperature that is decreased by from about 50° C. to about 300° C., when compared to a catalyst bed temperature of an otherwise similar catalyst bed comprising an OCM catalyst composition comprising a lanthanum (III) and cerium (IV) mixture without the Ag.

A thirtieth aspect, which is the method of any one of the twenty-fifth through the twenty-ninth aspects, wherein the reactor comprises an adiabatic reactor, an autothermal reactor, an isothermal reactor, a tubular reactor, a cooled tubular reactor, a continuous flow reactor, a fixed bed reactor, a fluidized bed reactor, a moving bed reactor, or combinations thereof.

A thirty-first aspect, which is the method any one of the twenty-fifth through the thirtieth aspects, wherein the reactant mixture further comprises a diluent.

A thirty-second aspect, which is the method of the thirty-first aspect, wherein the diluent comprises water, nitrogen, inert gases, or combinations thereof.

A thirty-third aspect, which is the method of any one of the twenty-fifth through the thirty-second aspects, wherein equal to or greater than about 10 mol % of the methane in the reactant mixture is converted to $C_{2+}$ hydrocarbons.

A thirty-fourth aspect, which is the method of any one of the twenty-fifth through the thirty-third aspects, wherein equal to or greater than about 20 mol % of selectivity to olefins is obtained.

A thirty-fifth aspect, which is the method of any one of the twenty-fifth through the thirty-fourth aspects, wherein equal to or greater than about 40 mol % of selectivity to $C_2$ hydrocarbons is obtained.

A thirty-sixth aspect, which is the method of any one of the twenty-fifth through the thirty-fifth aspects, wherein equal to or greater than about 20 mol % of selectivity to ethylene is obtained.

A thirty-seventh aspect, which is the method of any one of the twenty-fifth through the thirty-sixth aspects, wherein the product mixture comprises less than about 15 mol % carbon dioxide ($CO_2$).

A thirty-eighth aspect, which is the method of any one of the twenty-fifth through the thirty-seventh aspects further comprising minimizing deep oxidation of methane to carbon dioxide ($CO_2$).

A thirty-ninth aspect, which is the method of any one of the twenty-fifth through the thirty-eighth aspects, wherein the Ag comprises Ag nanoparticles, Ag microparticles, Ag nanowires, or combinations thereof.

A fortieth aspect, which is an oxidative coupling of methane (OCM) catalyst composition doped with silver (Ag).

A forty-first aspect, which is the OCM catalyst composition of the fortieth aspect, wherein the Ag comprises Ag nanoparticles, Ag microparticles, Ag nanowires, or combinations thereof.

A forty-second aspect, which is the OCM catalyst composition of the forty-first aspect, wherein the Ag nanoparticles are characterized by an average size of from about 1 nm to about 500 nm.

A forty-third aspect, which is the OCM catalyst composition of the forty-first aspect, wherein the Ag microparticles are characterized by an average size of from about 0.5 microns to about 50 microns.

A forty-fourth aspect, which is the OCM catalyst composition of the forty-first aspect, wherein the Ag nanowires are characterized by an average diameter of from about 1 nm to about 500 nm, and by an average length of from about 0.5 microns to about 50 microns.

A forty-fifth aspect, which is the OCM catalyst composition of any one of the forty-first through the forty-fourth aspects comprising from about 0.1 wt. % to about 20 wt. % Ag.

A forty-sixth aspect, which is the OCM catalyst composition of any one of the forty-first through the forty-fifth aspects further comprising a support, wherein at least a portion of the OCM catalyst composition contacts, coats, is embedded in, is supported by, and/or is distributed throughout at least a portion of the support.

A forty-seventh aspect, which is the OCM catalyst composition of the forty-sixth aspect, wherein the support comprises MgO, $Al_2O_3$, $SiO_2$, $ZrO_2$, or combinations thereof.

A forty-eighth aspect, which is the OCM catalyst composition of any one of the forty-sixth through the forty-seventh aspects, wherein the support is in the form of particles, pellets, monoliths, foams, honeycombs, or combinations thereof.

A forty-ninth aspect, which is the OCM catalyst composition of any one of the forty-first through the forty-eighth aspects formed into pellets and/or tablets.

A fiftieth aspect, which is the OCM catalyst composition of the forty-ninth aspect, wherein the pellets comprise a binder.

A fifty-first aspect, which is the OCM catalyst composition of the forty-ninth aspect, wherein the tablets exclude a binder.

A fifty-second aspect, which is an oxidative coupling of methane (OCM) catalyst composition comprising silver (Ag).

A fifty-third aspect, which is an oxidative coupling of methane (OCM) catalyst composition comprising silver (Ag) nanoparticles, Ag microparticles, Ag nanowires, or combinations thereof.

A fifty-fourth aspect, which is a method of making an oxidative coupling of methane (OCM) catalyst composition comprising doping the OCM catalyst composition with silver (Ag); and optionally thermally treating the OCM catalyst composition.

A fifty-fifth aspect, which is the method of the fifty-fourth aspect further comprising forming the OCM catalyst composition into pellets by extrusion.

A fifty-sixth aspect, which is the method of any one of the fifty-fourth through the fifty-fifth aspects further comprising forming the OCM catalyst composition into tablets under pressure.

A fifty-seventh aspect, which is the method of the fifty-fourth aspect further comprising contacting the OCM catalyst composition with a support.

A fifty-eighth aspect, which is the method of any one of the fifty-fourth through the fifty-seventh aspects, wherein the Ag comprises Ag nanoparticles, Ag microparticles, Ag nanowires, or combinations thereof.

A fifty-ninth aspect, which is an OCM catalyst produced by the method of any one of the fifty-fourth through the fifty-eighth aspects.

A sixtieth aspect, which is a method of making an oxidative coupling of methane (OCM) catalyst composition comprising adding silver (Ag) to the OCM catalyst composition; and optionally thermally treating the OCM catalyst composition.

A sixty-first aspect, which is a method for producing olefins comprising:

(a) introducing a reactant mixture to a reactor comprising an oxidative coupling of methane (OCM) catalyst composition, wherein the reactant mixture comprises methane ($CH_4$) and oxygen ($O_2$), wherein the OCM catalyst composition is doped with silver (Ag);

(b) allowing at least a portion of the reactant mixture to contact at least a portion of the OCM catalyst composition and react via an OCM reaction to form a product mixture comprising olefins;

(c) recovering at least a portion of the product mixture from the reactor; and (d) recovering at least a portion of the olefins from the product mixture.

A sixty-second aspect, which is the method of the sixty-first aspect, wherein the OCM reaction is characterized by an ignition temperature of from about 200° C. to about 500° C.

A sixty-third aspect, which is the method of any one of the sixty-first through the sixty-second aspects, wherein the OCM reaction is characterized by an ignition temperature that is decreased by from about 50° C. to about 300° C., when compared to an ignition temperature of an otherwise similar OCM reaction conducted in the presence of an OCM catalyst composition without the Ag.

A sixty-fourth aspect, which is the method of any one of the sixty-first through the sixty-third aspects, wherein the reactor comprises a catalyst bed comprising the OCM catalyst composition, wherein the catalyst bed is characterized by a catalyst bed temperature of from about 200° C. to about 1,100° C.

A sixty-fifth aspect, which is the method of any one of the sixty-first through the sixty-fourth aspects, wherein the reactor comprises a catalyst bed comprising the OCM catalyst composition, wherein the catalyst bed is characterized by a catalyst bed temperature that is decreased by from about 50° C. to about 300° C., when compared to a catalyst bed temperature of an otherwise similar catalyst bed comprising an OCM catalyst composition without the Ag.

A sixty-sixth aspect, which is the method of any one of the sixty-first through the sixty-fifth aspects, wherein the reactor comprises an adiabatic reactor, an autothermal reactor, an isothermal reactor, a tubular reactor, a cooled tubular reactor, a continuous flow reactor, a fixed bed reactor, a fluidized bed reactor, a moving bed reactor, or combinations thereof.

A sixty-seventh aspect, which is the method of any one of the sixty-first through the sixty-sixth aspects, wherein the reactant mixture further comprises a diluent.

A sixty-eighth aspect, which is the method of the sixty-seventh aspect, wherein the diluent comprises water, nitrogen, inert gases, or combinations thereof.

A sixty-ninth aspect, which is the method of any one of the sixty-first through the sixty-eighth aspects, wherein equal to or greater than about 10 mol % of the methane in the reactant mixture is converted to $C_{2+}$ hydrocarbons.

A seventieth aspect, which is the method of any one of the sixty-first through the sixty-ninth aspects, wherein equal to or greater than about 20 mol % of selectivity to olefins is obtained.

A seventy-first aspect, which is the method of any one of the sixty-first through the seventieth aspects, wherein equal to or greater than about 40 mol % of selectivity to $C_2$ hydrocarbons is obtained.

A seventy-second aspect, which is the method of any one of the sixty-first through the seventy-first aspects, wherein equal to or greater than about 20 mol % of selectivity to ethylene is obtained.

A seventy-third aspect, which is the method of any one of the sixty-first through the seventy-second aspects, wherein the product mixture comprises less than about 15 mol % carbon dioxide ($CO_2$).

A seventy-fourth aspect, which is the method of any one of the sixty-first through the seventy-third aspects further comprising minimizing deep oxidation of methane to carbon dioxide ($CO_2$).

A seventy-fifth aspect, which is the method of any one of the sixty-first through the seventy-fourth aspects, wherein the Ag comprises Ag nanoparticles, Ag microparticles, Ag nanowires, or combinations thereof.

Aspects Group D

A first aspect, which is a supported catalyst capable of catalyzing an oxidative couple of methane reaction, the supported catalyst comprising silver (Ag) doped $Mn/Na_2WO_4$ and a metal oxide support, wherein the catalyst has greater $CH_4$ conversion and $C_{2+}$ hydrocarbon selectivity as compared to the same $Mn/Na_2WO_4$ metal oxide supported catalyst that has not been doped with Ag.

A second aspect, which is the supported catalyst of the first aspect, wherein the catalyst's selectivity for $C_{2+}$ hydrocarbons is greater than the theoretical selectivity limit for $C_{2+}$ hydrocarbons for the oxidative coupling of methane reaction.

A third aspect, which is the supported catalyst of the second aspect, wherein the catalyst's life is greater than the same $Mn/Na_2WO_4$ metal oxide supported catalyst that has not been doped with Ag.

A fourth aspect, which is the supported catalyst of any one of the first through the third aspects, wherein the metal oxide support is silicon dioxide, lanthanum oxide, or aluminum oxide, or a combination thereof.

A fifth aspect, which is the supported catalyst of the fourth aspect, wherein the support is silicon dioxide.

A sixth aspect, which is the supported catalyst of the fifth aspect, wherein the catalyst consists essentially of, or consists of, silver, manganese, sodium, tungsten, oxygen, and silicon.

A seventh aspect, which is the supported catalyst of any one of the first through the sixth aspects, wherein the catalyst comprises 0.1 wt. % to 10 wt. % of Ag, alternatively 0.1 wt. % to 5 wt. % of Ag, or alternatively from 0.2% to 3.0% of Ag.

An eighth aspect, which is the supported catalyst of the seventh aspect, wherein the catalyst comprises 0.1 wt. % to 10 wt. % of manganese and 0.1 wt. % to 15 wt. % of $Na_2WO_4$.

A ninth aspect, which is the supported catalyst of any one of the first through the eighth aspects, wherein the catalyst is not a nanowire or present in a nanowire substrate.

A tenth aspect, which is the supported catalyst of any one of the first through the ninth aspects, wherein the catalyst is in powdered or particulate form.

An eleventh aspect, which is a method of producing $C_{2+}$ hydrocarbons from an oxidative coupling of methane reaction, the method comprising contacting a reactant feed that includes a methane containing gas and an oxygen containing gas with the catalyst of any one of the first through the tenth aspects to produce a product stream comprising $C_{2+}$ hydrocarbons.

A twelfth aspect, which is the method of the eleventh aspect, wherein the selectivity of $C_{2+}$ hydrocarbons is at least 60% to 90% at a reaction temperature of about 650° C. to about 750° C.

A thirteenth aspect, which is the method of any one of the eleventh and the twelfth aspects, wherein the reaction temperature is 600° C. to 775° C., alternatively 650° C. to 775° C., or alternatively 675° C. to 750° C.

A fourteenth aspect, which is the method of any one of the eleventh through the thirteenth aspects, wherein the methane containing gas is natural gas.

A fifteenth aspect, which is a system for producing $C_{2+}$ hydrocarbons, the system comprising an inlet for a reactant feed comprising methane and oxygen; a reaction zone that is configured to be in fluid communication with the inlet, wherein the reaction zone comprises the catalyst of any one of the first through the tenth aspects; and an outlet configured to be in fluid communication with the reaction zone and configured to remove a first product stream comprising $C_{2+}$ hydrocarbons from the reaction zone.

A sixteenth aspect, which is the system of the fifteenth aspect, wherein the reaction zone further comprises the reactant feed and the first product stream.

A seventeenth aspect, which is the system of the sixteenth aspect, wherein the temperature of the reactant feed at the inlet or just prior to or during contact with the catalyst is 600° C. to 775° C., alternatively 650° C. to 775° C., or alternatively 675° C. to 750° C.

An eighteenth aspect, which is the system of any one of the fifteenth through the seventeenth aspects, wherein the reaction zone is a continuous flow reactor selected from a fixed-bed reactor, a fluidized reactor, or a moving bed reactor.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. An oxidative coupling of methane (OCM) catalyst composition comprising a La—Ce oxide doped with silver (Ag), wherein the Ag comprises Ag nanoparticles, Ag microparticles, Ag nanowires, or combinations thereof; wherein at least a portion of the Ag nanoparticles, Ag microparticles, Ag nanowires, or combinations thereof are retained onto the La—Ce oxide; wherein the Ag nanoparticles are characterized by an average size of from about 1 nm to about 500 nm; wherein the Ag microparticles are characterized by an average size of from about 0.5 microns to about 50 microns; wherein the Ag nanowires are characterized by an average diameter of from about 1 nm to about 500 nm, and by an average length of from about 0.5 microns to about 50 microns; wherein the La—Ce oxide comprises a single metal oxide of lanthanum (III) and a single metal oxide of cerium (IV); and wherein the OCM catalyst composition is characterized by a lanthanum (III) amount of from about 85.0 wt. % to about 95.0 wt. % and by a Ag amount of from about 1.0 wt. % to about 5.0 wt. %, based on the total weight of the OCM catalyst composition.

2. The OCM catalyst composition of claim 1 further comprising one or more additional oxides, wherein the one or more additional oxides comprises a single metal oxide, mixtures of single metal oxides, a mixed metal oxide, mixtures of mixed metal oxides, or combinations thereof.

3. The OCM catalyst composition of claim 2, wherein the one or more additional oxides comprises (i) a single metal oxide having one metal cation selected from the group consisting of alkali metal cations, alkaline earth metal cations, rare earth element cations other than lanthanum (III) or cerium (IV), and cations of elements that can form oxides with redox properties; or (ii) a mixture of single metal oxides.

4. The OCM catalyst composition of claim 2, wherein the one or more additional oxides comprises (a) a mixed metal oxide having two or more different metal cations, wherein each metal cation can be independently selected from the group consisting of alkali metal cations, alkaline earth metal cations, rare earth element cations, and cations of elements that can form oxides with redox properties; or (b) a mixture of mixed metal oxides.

5. The OCM catalyst composition of claim 2, wherein the one or more additional oxides comprises alkali metal oxides, alkaline earth metal oxides, oxides of elements that can form oxides with redox properties, rare earth element oxides other than $La_2O_3$ and/or $CeO_2$, or combinations thereof.

6. The OCM catalyst composition of claim 5, wherein the alkali metal oxides comprise cations of lithium (Li), sodium (Na), potassium (K), rubidium (Rb), cesium (Cs), or combinations thereof.

7. The OCM catalyst composition of claim 5, wherein the alkaline earth metal oxides comprise cations of magnesium (Mg), calcium (Ca), strontium (Sr), barium (Ba), or combinations thereof.

8. The OCM catalyst composition of claim 5, wherein the rare earth element oxides other than $La_2O_3$ and/or $CeO_2$ further comprise cations of lanthanum (La), cerium (Ce), praseodymium (Pr), neodymium (Nd), samarium (Sm), europium (Eu), dysprosium (Dy), holmium (Ho), erbium (Er), ytterbium (Yb), or combinations thereof.

9. The OCM catalyst composition of claim 5, wherein the oxides of elements that can form oxides with redox properties comprise cations of manganese (Mn), tungsten (W), vanadium (V), tin (Sn), antimony (Sb), phosphorus (P), arsenic (As), chromium (Cr), bismuth (Bi), gallium (Ga), rhenium (Re), lead (Pb), iron (Fe), cobalt (Co), nickel (Ni), copper (Cu), niobium (Nb), molybdenum (Mo), or combinations thereof.

10. The OCM catalyst composition of claim 1 further comprising a support, wherein at least a portion of the OCM catalyst composition contacts, coats, is embedded in, is supported by, and/or is distributed throughout at least a portion of the support; wherein the support comprises MgO, $Al_2O_3$, $SiO_2$, $ZrO_2$, or combinations thereof; and wherein the support is in the form of particles, pellets, monoliths, foams, honeycombs, or combinations thereof.

11. The OCM catalyst composition of claim 2, wherein the one or more additional oxides comprises $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, MnO—$W_2O_3$, MnO—$W_2O_3$—$Na_2O$, MnO—$W_2O_3$—$Li_2O$, SrO/$La_2O_3$, $Ce_2O_3$, La/MgO, $La_2O_3$—$CeO_2$—$Na_2O$, $La_2O_3$—$CeO_2$—CaO, $Na_2O$—MnO—$WO_3$—$La_2O_3$, $La_2O_3$—$CeO_2$—MnO—$WO_3$—SrO, Na—Mn—$La_2O_3$/$Al_2O_3$, Na—Mn—O/$SiO_2$, $Na_2WO_4$—Mn/$SiO_2$, $Na_2WO_4$—Mn—O/$SiO_2$, Na/Mn/O, $Na_2WO_4$, $Mn_2O_3$/$Na_2WO_4$, $Mn_3O_4$/$Na_2WO_4$, $MnWO_4$/$Na_2WO_4$, $MnWO_4$/$Na_2WO_4$, Mn/$WO_4$, $Na_2WO_4$/Mn, Sr/Mn—$Na_2WO_4$, or combinations thereof.

12. An oxidative coupling of methane (OCM) catalyst composition comprising a lanthanum (III) and cerium (IV) mixture doped with silver (Ag); wherein the lanthanum (III) and cerium (IV) mixture comprises two or more oxides; wherein the Ag comprises Ag nanoparticles, Ag microparticles, Ag nanowires, or combinations thereof; wherein at least a portion of the Ag nanoparticles, Ag microparticles, Ag nanowires, or combinations thereof are retained onto the two or more oxides; wherein the Ag nanoparticles are characterized by an average size of from about 1 nm to about 500 nm; wherein the Ag microparticles are characterized by an average size of from about 0.5 microns to about 50 microns; wherein the Ag nanowires are characterized by an average diameter of from about 1 nm to about 500 nm, and by an average length of from about 0.5 microns to about 50 microns; and wherein the OCM catalyst composition is characterized by a lanthanum (III) amount of from about 75.0 wt. % to about 98.0 wt. % and by a Ag amount of from about 0.5 wt. % to about 10.0 wt. %, based on the total weight of the OCM catalyst composition.

13. The OCM catalyst composition of claim 12, wherein lanthanum (III) comprises $La_2O_3$, and optionally $La(OH)_3$; and wherein cerium (IV) comprises $CeO_2$.

14. The OCM catalyst composition of claim 12 comprising (i) from about 1 wt. % to about 5 wt. % Ag; (ii) from about 85.0 wt. % to about 95.0 wt. % lanthanum (III); and (iii) from about 4.0 wt. % to about 10.0 wt. % cerium (IV).

15. A supported oxidative coupling of methane (OCM) catalyst capable of catalyzing an OCM reaction, the supported OCM catalyst comprising silver (Ag) doped Mn/$Na_2WO_4$ and a metal oxide support, wherein the supported OCM catalyst has greater $CH_4$ conversion and $C_{2+}$ hydrocarbon selectivity as compared to the $CH_4$ conversion and $C_{2+}$ hydrocarbon selectivity, respectively, of an otherwise similar Mn/$Na_2WO_4$ metal oxide supported OCM catalyst that has not been doped with Ag.

16. The supported OCM catalyst of claim 15, wherein the supported OCM catalyst's selectivity for $C_{2+}$ hydrocarbons is greater than a theoretical selectivity limit for $C_{2+}$ hydrocarbons for the oxidative coupling of methane reaction; and wherein the supported OCM catalyst's life is greater than the life of an otherwise similar Mn/$Na_2WO_4$ metal oxide supported OCM catalyst that has not been doped with Ag.

17. The OCM catalyst composition of claim 1, wherein at least a portion of an outer surface of the Ag nanoparticles, Ag microparticles, Ag nanowires, or combinations thereof is unobstructed by the one or more oxides from contact with methane.

18. The OCM catalyst composition of claim 1, wherein the Ag comprises Ag nanoparticles, and wherein the Ag nanoparticles are characterized by an average size of from about 2.5 nm to about 100 nm.

19. The OCM catalyst composition of claim 1, wherein the Ag comprises Ag nanoparticles, and wherein the Ag nanoparticles are characterized by an average size of from about 10 nm to about 20 nm.

20. The OCM catalyst composition of claim 1, wherein the Ag comprises Ag nanowires, wherein the Ag nanowires are characterized by an average diameter of from about 25 nm to about 50 nm; and by an average length of from about 5 microns to about 10 microns.

21. The OCM catalyst composition of claim 1, wherein the Ag comprises Ag microparticles, wherein the Ag microparticles are characterized by an average size of from about 5 microns to about 10 microns.

* * * * *